United States Patent
Meijers et al.

(10) Patent No.: US 10,813,944 B2
(45) Date of Patent: Oct. 27, 2020

(54) CYCLODEXTRINS AS PROCOAGULANTS

(71) Applicants: STICHTING SANQUIN BLOEDVOORZIENING, Amsterdam (NL); OKKLO LIFE SCIENCES B.V., Nijmegen (NL)

(72) Inventors: Josephus Cornelis Maria Meijers, Amsterdam (NL); Kamran Bakhtiari, Amsterdam (NL); Stephan Leonard Maria Peters, Nijmegen (NL); Daniel Philipp Zollinger, Nijmegen (NL)

(73) Assignee: ALVERON PHARMA B.V., Nijmegen (NL)

( * ) Notice: Subject to any disclaimer, the term of this patent is extended or adjusted under 35 U.S.C. 154(b) by 40 days.

(21) Appl. No.: 16/097,301

(22) PCT Filed: May 1, 2017

(86) PCT No.: PCT/NL2017/050275
§ 371 (c)(1),
(2) Date: Oct. 29, 2018

(87) PCT Pub. No.: WO2017/188820
PCT Pub. Date: Nov. 2, 2017

(65) Prior Publication Data
US 2019/0381091 A1    Dec. 19, 2019

(30) Foreign Application Priority Data

Apr. 29, 2016 (EP) .................................. 16167738

(51) Int. Cl.
| | | |
|---|---|---|
| *A61K 31/724* | (2006.01) | |
| *A61K 47/26* | (2006.01) | |
| *A61P 7/04* | (2006.01) | |
| *A61K 9/00* | (2006.01) | |
| *A61K 9/06* | (2006.01) | |
| *A61K 38/37* | (2006.01) | |
| *A61K 38/48* | (2006.01) | |
| *C08B 37/16* | (2006.01) | |

(52) U.S. Cl.
CPC .......... *A61K 31/724* (2013.01); *A61K 9/0014* (2013.01); *A61K 9/06* (2013.01); *A61K 38/37* (2013.01); *A61K 38/4846* (2013.01); *A61K 47/26* (2013.01); *A61P 7/04* (2018.01); *C08B 37/0012* (2013.01); *C12Y 304/21022* (2013.01)

(58) Field of Classification Search
None
See application file for complete search history.

(56) References Cited

U.S. PATENT DOCUMENTS

| | | | | |
|---|---|---|---|---|
| 6,670,340 | B1 * | 12/2003 | Zhang ................. | C08B 37/0012 514/58 |
| 2004/0048830 | A1 * | 3/2004 | Zhang ..................... | A61P 25/18 514/58 |
| 2013/0244979 | A1 * | 9/2013 | Qi ........................... | A61P 21/00 514/58 |

FOREIGN PATENT DOCUMENTS

| | | |
|---|---|---|
| JP | 2000229882 A | 8/2000 |
| WO | 0140316 A1 | 6/2001 |
| WO | 2013116366 A1 | 8/2013 |

OTHER PUBLICATIONS

Nag et al., "Sugammadex: A revolutionary drug in neuromuscular pharmacology" Anesth Essays Res vol. 7 No. 3 pp. 302-306 (Year: 2013).*
Raft et al., "Biological evaluation of the effect of sugammadex on hemostasis and bleeding", Korean Journal of Anesthesiology, 2015, vol. 68, No. 1, pp. 17-21.
Adam et al., "Cyclodextrin-Derived Host Molecules as Reversal Agents for the Neuromuscular Blocker Rocuroniurn Bromide: Synthesis and Structure-Activity Relationships", J. Med. Chem., 2002, vol. 45, No. 9, pp. 1806-1816.
International Search Report and Written Opinion for Corresponding International Application No. PCT/NL2017/050275 (dated Aug. 2, 2017) (11 Pages).

* cited by examiner

*Primary Examiner* — Eric Olson
(74) *Attorney, Agent, or Firm* — Lucas & Mercanti, LLP

(57) ABSTRACT

The invention relates to substituted cyclodextrins and pharmaceutically acceptable salts thereof, pharmaceutical compositions, kits of parts and their use as procoagulants. The invention further relates to methods of reversing an anticoagulant effect of an anticoagulant in a subject, methods for reducing or preventing bleeding in a subject and methods for the treatment or prevention of a blood coagulation disorder.

18 Claims, 32 Drawing Sheets

(a) Chemical Structure n = 1 (α-CD), 2 (β-CD), 3 (γ-CD)

(b) 3D Structure

Primary Face

Secondary Face

A

B

C

D

CYCLODEXTRINS AS PROCOAGULANTS

CROSS-REFERENCE TO RELATED APPLICATIONS

This application is a 371 of PCT/NL2017/050275, filed May 1, 2017 which claims the benefit of European Patent Application No. 16167738.0, filed Apr. 29, 2016.

FIELD OF THE INVENTION

The invention relates to the field of medicine, in particular to substituted cyclodextrins and their use as procoagulants.

BACKGROUND OF THE INVENTION

Thromboembolic disorders such as myocardial infarction, stroke, and venous thromboembolism are the most common causes of mortality and morbidity in Western societies. These thromboembolic events can be triggered by excessive activation of coagulation, and thrombin plays a major role in these processes. The most widely used agents for antithrombotic therapy are heparins (including low molecular weight heparins, LMWH) and oral indirect thrombin inhibitors such as vitamin K antagonists (VKA) (warfarin, acenocoumarol and phenprocoumon). However, because of the need for frequent monitoring and the desire for safer anticoagulants, several novel non-vitamin K-dependent oral anticoagulants (NOACs) have been developed. These newer agents include the factor Xa inhibitors (such as rivaroxaban, apixaban, edoxaban), along with the direct thrombin inhibitors (dabigatran). Unlike the vitamin K antagonists, these new anticoagulants do not require routine (INR) monitoring and possess favourable pharmacological properties. NOACs act rapidly, and have a stable and predictable dose-related anticoagulant effect with few clinically relevant drug-drug interactions. Despite these improvements in treatment, anticoagulation therapy in general is associated with an increased risk of bleeding.

The traditional anticoagulants, unfractionated heparin (UFH) and the vitamin K antagonists (VKA), have antidotes to reverse their intended therapeutic effect. Protamine sulfate largely reverses the antithrombotic effect of UHF, but not without some potential serious side effects. Vitamin K reverses the impaired coagulation induced by the VKAs by re-establishing synthesis of the reduced vitamin K-dependent coagulation factors, but not without the drawback of requiring 12-24 h to achieve significant levels of these factors to improve coagulation. LMWHs and fondaparinux, both further refinements on the heparin molecule, have a more limited ability of reversal by protamine sulfate. Fondaparinux has only anti-Xa activity and is not reversed by protamine sulphate, which is also the case for danaparoid. In addition, also argatroban and bivalirudin (intravenous anticoagulants) have no reversal agent, but they have a very short half-life of 30-50 min, their indications are limited and their use is usually for relatively short durations.

The more recent non-vitamin K-dependent oral anticoagulants are small molecules that bind directly to their intended target, either activated factor II (IIa or thrombin) or activated factor X (Xa) and antagonize their activity. These drugs are intended for long-term, outpatient use for many of the same indications as the VKAs. Consequently, not only are there millions of users for these drugs, but for many indications they are taken over a significant portion of one's lifetime. This results in many patient-years where individuals are at risk for bleeding, either spontaneously or following trauma or surgical procedures. Only for one anti-IIa inhibitor (dabigatran) a selective antidote is currently available. For the other NOACs (rivaroxaban, edoxaban and apixaban) antidotes have not yet been developed. There is general consensus that the lack of a reversal agent for the NOACs is a major barrier to their more widespread use, and even with their short half-life, being able to rapidly reverse anticoagulation in the face of major or life threatening bleeding would certainly be beneficial. Reversal might also be valuable in the setting of overdose or in preparation for emergency surgery or interventions. For elective interventions, a reversal agent might also allow for shorter intervals when a patient is sub-therapeutic in preparation for the intervention.

Consequently, there remains a need for safe, immediately effective, and easy to administer antidotes for patients taking anticoagulants in the settings of major bleeding, need for emergency surgery, and accidental overdose. A general antidote that may be used in emergency situations regardless of which type of anticoagulant therapy has been used, would in particular have advantages over more selective antidotes since, especially in emergency situations, the exact type of anticoagulant therapy is often unknown. A preferred general antidote may find additional use as a procoagulant in the treatment of bleeding disorders.

SUMMARY OF THE INVENTION

It is an object of the present invention to provide cyclodextrins that have a procoagulant effect. Preferably the cyclodextrins have such procoagulant effect both in the presence and absence of anticoagulants. It is a further object of the present invention to provide methods for reversing an anticoagulant effect of an anticoagulant and/or for reducing or preventing bleeding in a subject and/or for treating or preventing blood coagulation disorders.

The invention therefore provides a substituted cyclodextrin according to formula I, comprising at least one substituent —S—($C_n$alkylene)-R, wherein n is 3-7, and R is selected from the group consisting of —COOH, —OH, and —COO(1-4C)alkyl, or a pharmaceutically acceptable salt thereof.

Formula (I)

In a preferred substituted cyclodextrin according to the invention, p+q is 6, 7 or 8, whereby p is 5 and q is 1, or p is 6 and q is 1, or p is 7 and q is 1, or p is 0 and q is 6, or p is 0 and q is 7, or p is 0 and q is 8.

In preferred substituted cyclodextrin according to the invention, S—($C_n$alkylene)-R is —S—$(CH_2)_m$—R, wherein m is an integer from 3 to 7. In a preferred substituted cyclodextrin according to the invention, R is—selected from the group consisting of —COOH and —OH.

In a most preferred substituted cyclodextrin according to the invention, p is 0, q is 8, m is 5, and H is COOH.

The invention further provides a pharmaceutical composition comprising a substituted cyclodextrin according to the invention, and at least one pharmaceutically acceptable auxiliary.

In a further aspect, the invention provides a kit of parts comprising:
    substituted cyclodextrin according to the invention, or a pharmaceutically acceptable salt thereof, and
    a recombinant or isolated coagulation factor.

In a further aspect, the invention provides a substituted cyclodextrin according to the invention, or a pharmaceutically acceptable salt thereof for use as a procoagulant.

In a further aspect, the invention provides a substituted cyclodextrin according to the invention, or a pharmaceutically acceptable salt thereof for use in a method for reversing an anticoagulant effect of an anticoagulant in a subject.

In a further aspect, the invention provides a method for reversing an anticoagulant effect of an anticoagulant in a subject in need thereof, the method comprising administering to the subject, which subject has been administered said anticoagulant, a therapeutically effective amount of a substituted cyclodextrin according to the invention, or a pharmaceutically acceptable salt thereof.

In a further aspect, the invention provides a substituted cyclodextrin according to the invention, or a pharmaceutically acceptable salt thereof for the preparation of a medicament for reversing an anticoagulant effect of an anticoagulant in a subject.

In a further aspect, the invention provides a substituted cyclodextrin according to the invention, or a pharmaceutically acceptable salt thereof for use in a method for reducing or preventing bleeding in a subject.

Also provided is a method for inducing or stimulating coagulation in a subject in need thereof comprising administering to the subject a therapeutically effective amount of a substituted cyclodextrin according to the invention, or a pharmaceutically acceptable salt thereof.

In a further aspect, the invention provides a method for reducing or preventing bleeding in a subject in need thereof, the method comprising administering to the subject a therapeutically effective amount of a substituted cyclodextrin according to the invention, or a pharmaceutically acceptable salt thereof.

In a further aspect, the invention provides a substituted cyclodextrin according to the invention, or a pharmaceutically acceptable salt thereof for the preparation of a medicament for reducing or preventing bleeding in a subject.

In a further aspect, the invention provides a substituted cyclodextrin according to the invention, or a pharmaceutically acceptable salt thereof for use in a method for the treatment or prevention of a blood coagulation disorder.

In a further aspect, the invention provides a method for the treatment or prevention of a blood coagulation disorder, comprising administering to a subject in need thereof a therapeutically effective amount of a substituted cyclodextrin according to the invention, or a pharmaceutically acceptable salt thereof.

In a further aspect, the invention provides a substituted cyclodextrin according to the invention, or a pharmaceutically acceptable salt thereof for the preparation of a medicament for the treatment or prevention of a blood coagulation disorder.

DETAILED DESCRIPTION

The present inventors have identified a set of cyclodextrins having one or more specific substituents that have a procoagulant effect both in vitro and in vivo. Such procoagulant effect of cyclodextrins was previously unknown. The effect of the cyclodextrins on several parameters of thrombin generation were inter alia determined. Thrombin generation is one of the final stages in the blood coagulation process and therefore a particularly important parameter when assessing the effect of a compound on the coagulation process. The procoagulant activity of the cyclodextrins is evidenced by a reduction in the lag time for thrombin generation, an increase in the peak thrombin level, a reduction in the time to peak thrombin level or a combination thereof in the presence of the cyclodextrins of the invention. In addition, procoagulant activity of the cyclodextrins was demonstrated in vivo as evidenced by stimulation of blood clot formation. As is shown in the Examples, the cyclodextrins described herein are capable of at least partly reversing the anticoagulant effect of a wide array of anticoagulant agents. It has further been shown that specific cyclodextrins described herein exert a procoagulant effect in normal pooled plasma, i.e. they influence normal blood coagulation in the absence of anticoagulants or deficiency of a coagulation factor. Moreover, the cyclodextrins described herein have a procoagulant effect in plasma deficient in a blood coagulation factor.

The use of cyclodextrins as described herein as procoagulants has many advantages over the use of known procoagulants. For instance, the cyclodextrins have the advantage that they can be used to reverse the anticoagulant effect of a wide variety of anticoagulants. The anticoagulant activity of direct acting oral anticoagulants such as factor Xa inhibitors (e.g. rivaroxaban, apixaban, edoxaban), and direct thrombin inhibitors (e.g. dabigatran), of pentasaccharides such as fondaparinux, of low molecular weight heparins such as nadroparin and tinzaparin, of unfractionated heparin and of vitamin K antagonists is reversed by the cyclodextrins described herein. Contrary, many of the currently known procoagulants are specific for one anticoagulant or one class of anticoagulants. Consequently, the cyclodextrins of the present invention can be used to reverse an anticoagulant effect without the need to identify the specific anticoagulant first since, in emergency situations, this is often unknown. A general procoagulant that may be used regardless of which type of anticoagulant therapy has been used, is preferred over more selective antidotes in emergency situations.

In addition, the cyclodextrins of the present invention are able to reverse the anticoagulant of compounds such as argatroban, bivalirudin, rivaroxaban, edoxaban and apixaban for which currently no reversal agents are available.

Further, the cyclodextrins of the present invention in principle exert their procoagulant activity rapidly after administration, e.g. within minutes, unlike many known specific procoagulant such as vitamin K, which is able to reverse the anticoagulant effect of vitamin K antagonists only after 12-24 h. However, the half-life of cyclodextrins is dependent on their hydrophilicity. Hence, the half-life of the cyclodextrins of the invention can be influenced, typically by the introduction of groups that are more hydrophilic or the introduction of additional hydrophilic groups. This results in an increase in the half-life of the cyclodextrins. This way, the cyclodextrins can be modified to have the optimal half-life for a desired application.

In addition to the above, cyclodextrins have been widely used in food products and pharmaceutical compositions. They are associated with little side-effects. For instance, cyclodextrins are less immunogenic when administered to humans as compared to proteinaceous procoagulants, such as recombinant coagulation factors that are currently used to treat patients suffering from a deficiency in such coagulation factor.

Accordingly the invention provides a substituted cyclodextrin comprising at least one substituent —S—($C_n$alkylene)-R, wherein n is 1 or an integer from 3 to 10 and H is selected from the group consisting of —COOH, —OH, and —COO(1-4C)alkyl, or a pharmaceutically acceptable salt thereof. Preferably n is an integer from 3 to 7.

The invention further provides a substituted cyclodextrin comprising at least one substituent —S—($C_n$alkylene)-R, wherein n is 1 or an integer from 3 to 10, preferably 3-7, and R is selected from the group consisting of —COOH, —OH, and —COO(1-4C)alkyl, or a pharmaceutically acceptable salt thereof for use as a procoagulant.

A substituted cyclodextrin comprising at least one substituent —S—($C_n$alkylene)-R, wherein n is 1 or an integer from 3 to 10, preferably 3-7, and R is selected from the group consisting of —COOH, —OH, and —COO(1-4C) alkyl is herein also referred to as "a substituted cyclodextrin according to the invention".

Cyclodextrins are a family of cyclic oligosaccharides. Cyclodextrins are composed of 6 or more α-D-glucopyranoside units linked 1→4 (see FIG. 1a). Cyclodextrins containing 6, 7 and 8 sugar units are referred to as alpha-cyclodextrins (α-CD), beta-cyclodextrins (β-CD) and gamma-cyclodextrins (γ-CD), respectively. Cyclodextrins contain a somewhat lipophilic central cavity and a hydrophilic outer surface. They are used in food, pharmaceutical and chemical industries and for drug delivery. One or more of the —OH groups can be substituted to provide a wide variety of cyclodextrin derivatives or substituted cyclodextrins.

As used herein, the term "cyclodextrin" refers to a cyclic oligosaccharide moiety composed of 6 or more -D-glucopyranoside units linked through α-(1,4) glucosidic bonds. The term "substituted cyclodextrin" as used herein refers to a cyclodextrin moiety which is substituted with at least one substituent —S—($C_n$alkylene)-R group, wherein n and R are as defined herein. Such substituted cyclodextrin is also referred to as a cyclodextrin derivative. Preferably, one or more —OH groups located on the primary face of the cyclodextrin moiety (see FIG. 1b) is replaced with an —O—S—($C_n$alkylene)-R group, wherein n and R are as defined herein. Said cyclodextrin moiety does not contain any further substituents.

A substituted cyclodextrin according to the invention or for use according to the invention preferably comprises 6-10 glucopyranoside units, more preferably 6-8 units. Hence, a substituted cyclodextrin preferably comprises α-cyclodextrin, β-cyclodextrin, γ-cyclodextrin or mixtures thereof. Further preferred is a mixture of one or more substituted α-cyclodextrins, one ore more substituted β-cyclodextrins and/or one or more substituted γ-cyclodextrins. Hence, a substituted cyclodextrin more preferably comprises α-cyclodextrin, β-cyclodextrin, γ-cyclodextrin or mixtures thereof.

The substituted cyclodextrin is preferably substantially free of an inclusion complex compound, i.e. a compound that forms a complex with the cyclodextrin and is located inside lipophilic central cavity of the cyclodextrin.

A substituted cyclodextrin according to the invention or for use according to the invention comprises at least one substituent —S—($C_n$alkylene)-R, wherein n is 1 or an integer from 3 to 10 and R is selected from the group consisting of —COOH, —OH, and —COO(1-4C)alkyl. Preferably n is an integer from 3 to 7. Substitutions are preferably made through substitution of the primary hydroxyl groups located on the primary face of the glucopyranose units (see FIG. 1b).

A substituted cyclodextrin according to the invention or for use according to the invention preferably has the formula (I):

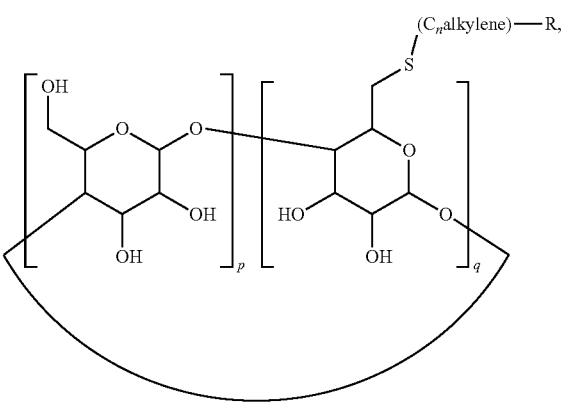

Formula (I)

wherein n is 1 or an integer from 3 to 10, preferably n is an integer from 3 to 7, p is an integer from 0 to 7 and q is an integer from 1 to 8 with the proviso that p+q is 6, 7 or 8. Preferably, p+q is 7 or 8.

As used herein, the term "—$C_n$alkylene-" refers to a branched or unbranched saturated alkylene group having n carbon atoms. For instance, $C_n$alkylene wherein n is 4 can be the following: —$(CH_2)_4$—, —$C(CH_3)_2$—$CH_2$—, —$CHCH_3$—$(CH_2)_2$—. In substituent —S—($C_n$alkylene)-R, n is preferably an integer from 3 to 10, more preferably from 3 to 9, more preferably from 3 to 8, more preferably from 3 to 7, or from 3 to 5. In a particularly preferred substituted cyclodextrin, n is an integer from 3 to 7. Said substituent —S—($C_n$alkylene)-R preferably is —S—$(CH_2)_m$—R, wherein m is 1 or an integer from 3 to 10, and the —$(CH_2)_m$— moiety is optionally substituted with 1 to 3 $CH_3$ groups, with the proviso that the total number of carbon atoms does not exceed 10. In a further preferred embodiment, m is an integer from 3 to 10, more preferably from 3 to 9, more preferably from 3 to 8, more preferably from 3 to 7, more preferably from 3 to 5, and the —$(CH_2)_m$— moiety is optionally substituted with 1 to 3 $CH_3$ groups, with the proviso that the total number of carbon atoms does not exceed 10. The total number of carbon atoms preferably does not exceed 8, more preferably 7, more preferably 6, more preferably 5. In a particularly preferred embodiment, the —$(CH_2)_m$— moiety is unsubstituted.

Therefore, a substituted cyclodextrin according to the invention or for use according to the invention preferably has the formula (II):

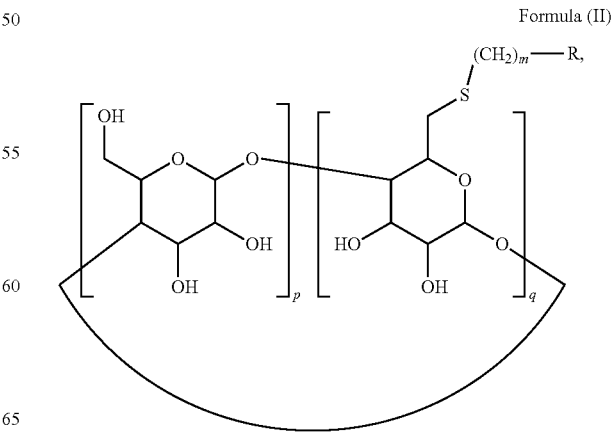

Formula (II)

wherein m is 1 or an integer from 3 to 10, preferably m is an integer from 3 to 7, the —(CH$_2$)$_m$— moiety is optionally substituted with 1 to 3 CH$_3$ groups with the proviso that the total number of carbon atoms does not exceed 10, p is an integer from 0 to 7 and q is an integer from 1 to 8 with the proviso that p+q is 6, 7 or 8. Preferably, p+q is 7 or 8. In a particularly preferred embodiment, the —(CH$_2$)$_m$— moiety is unsubstituted and m is an integer from 3 to 7, more preferably from 3 to 5.

A substituted cyclodextrin according to the invention or for use according to the invention comprises at least one substituent —S—(C$_n$alkylene)-R. In a preferred embodiment, a substituted α-cyclodextrin comprises 1 to 6 of such substituents, a substituted β-cyclodextrin comprises 1 to 7 of such substituents and/or a substituted γ-cyclodextrin comprises 1 to 8 of such substituents. In a particularly preferred embodiment, a substituted cyclodextrin according to the invention or for use according to the invention, preferably α-cyclodextrin, β-cyclodextrin and/or γ-cyclodextrin, is a mono-substituted or per-substituted cyclodextrin.

As used herein, the term "mono-substituted cyclodextrin" refers to a cyclodextrin comprising one substituent —S—(C$_n$alkylene)-R or —S—(CH$_2$)$_m$—R as defined herein. In a mono-substituted α-cyclodextrin according to formula (I) or formula (II), p is 5 and q is 1. In a mono-substituted κ-cyclodextrin according to formula (I) or formula (II), p is 6 and q is 1. In a mono-substituted γ-cyclodextrin according to formula (I) or formula (II), p is 7 and q is 1.

As used herein the term "per-substituted cyclodextrin" refers to a cyclodextrin wherein all primary OH-groups are substituted with a substituent —S—(C$_n$alkylene)-R or —S—(CH$_2$)$_m$—R as defined herein. Hence, a per-substituted α-cyclodextrin contains 6 substituents —S—(C$_n$alkylene)-R or —S—(CH$_2$)$_m$—R as defined herein, a per-substituted β-cyclodextrin contains 7 substituents —S—(C$_n$alkylene)-R or —S—(CH$_2$)$_m$—R as defined herein and a per-substituted γ-cyclodextrin contains 8 substituents —S—(C$_n$alkylene)-R or —S—(CH$_2$)$_m$—R as defined herein. In a per-substituted α-cyclodextrin according to formula (I) or formula (II), p is 0 and q is 6. In a per-substituted β-cyclodextrin according to formula (I) or formula (II), p is 0 and q is 7. In a per-substituted γ-cyclodextrin according to formula (I) or formula (II), p is 0 and q is 8.

Hence, in formula (I) and formula (II), preferably p+q is either 7, whereby p is 0 and q is 7, or p is 6 and q is 1; or p+q is 8, whereby p is 0 and q is 8, or p is 7 and q is 1.

In substituent —S—(C$_n$alkylene)-R and in substituent —S—(CH$_2$)$_m$—R, wherein n and m are as defined herein, R is selected from the group consisting of COOH, —OH, and —COO(1-4C)alkyl. Most preferably, R is selected from the group consisting of COOH and OH.

Particularly preferred substituted cyclodextrins according to the invention or for use according to the invention are cyclodextrins of formula (I) wherein:
p is an integer from 0 to 7 and q is an integer from 1 to 8 with the proviso that p+q is 7 or 8;
n is 1 or an integer from 3 to 10, preferably n is an integer from 3 to 7, more preferably from 3 to 5; and
R is selected from the group consisting of —COOH, —OH, and —COO(1-4C)alkyl, more preferably from the group consisting of —COOH and —OH,
or a pharmaceutically acceptable salt thereof.

Further preferred substituted cyclodextrins according to the invention or for use according to the invention are cyclodextrins of formula (I) wherein:
p+q is either 7, whereby p is 0 and q is 7, or p is 6 and q is 1; or p+q is 8, whereby p is 0 and q is 8, or p is 7 and q is 1;
n is 1 or an integer from 3 to 10, preferably n is an integer from 3 to 7, more preferably from 3 to 5; and
R is selected from the group consisting of —COOH, —OH, and —COO(1-4C)alkyl, more preferably from the group consisting of —COOH and —OH,
or a pharmaceutically acceptable salt thereof.

Further preferred substituted cyclodextrins according to the invention or for use according to the invention are cyclodextrins of formula (II) wherein:
p+q is either 7, whereby p is 0 and q is 7; or p is 6 and q is 1; or p+q is 8, whereby p is 0 and q is 8, or p is 7 and q is 1;
m is an integer from 3 to 7, preferably from 3 to 5;
the —(CH$_2$)$_m$— moiety is optionally substituted with 1 to 3 CH$_3$ groups, preferably wherein the —(CH$_2$)$_m$— moiety is unsubstituted; and
R is selected from the group consisting of —COOH, —OH, and —COO(1-4C)alkyl more preferably from the group consisting of —COOH and —OH,
or a pharmaceutically acceptable salt thereof.

Further preferred substituted cyclodextrins according to the invention or for use according to the invention are cyclodextrins of formula (II) wherein:
p+q is either 7, whereby p is 0 and q is 7, or p is 6 and q is 1; or p+q is 8, whereby p is 0 and q is 8, or p is 7 and q is 1;
m is an integer from 3 to 7, preferably from 3 to 5;
the —(CH$_2$)$_m$— moiety is unsubstituted; and
R is selected from the group consisting of —COOH and —OH,
or a pharmaceutically acceptable salt thereof.

Further preferred substituted cyclodextrins according to the invention or for use according to the invention are cyclodextrins of formula (II) wherein:
p+q is 7, whereby p is 0 and q is 7;
the —(CH$_2$)$_m$— moiety is unsubstituted;
m is 3 or 4, preferably 3; and
R is selected from the group consisting of —COOH and —OH, preferably R is COOH,
or a pharmaceutically acceptable salt thereof.

Further preferred substituted cyclodextrins according to the invention or for use according to the invention are cyclodextrins of formula (II) wherein:
p+q is 7, whereby p is 6 and q is 1;
the —(CH$_2$)$_m$— moiety is unsubstituted;
m is an integer from 3 to 7, preferably an integer from 3 to 5, more preferably an integer from 3 to 5, more preferably m is 5; and
R is selected from the group consisting of —COOH and —OH, preferably R is COOH,
or a pharmaceutically acceptable salt thereof.

Further preferred substituted cyclodextrins according to the invention or for use according to the invention are cyclodextrins of formula (II) wherein:
p+q is 8, whereby p is 0 and q is 8;
the —(CH$_2$)$_m$— moiety is unsubstituted;
m is an integer from 3 to 7, preferably from 3 to 5, more preferably 3 or 5; and
R is selected from the group consisting of —COOH and —OH, preferably R is COOH,
or a pharmaceutically acceptable salt or ester thereof.

Further preferred substituted cyclodextrins according to the invention or for use according to the invention are cyclodextrins of formula (II) wherein:

p+q is 8, whereby p is 7 and q is 1;
the —(CH$_2$)$_m$— moiety is unsubstituted;
m is an integer from 3 to 7, preferably from 3 to 5, more preferably 3 or 5; and
R is selected from the group consisting of —COOH and —OH, preferably R is COOH,
or a pharmaceutically acceptable salt or ester thereof.

Particularly preferred substituted cyclodextrins according to the invention and/or used in accordance with the inventions are cyclodextrins of formula (II) wherein:
p is 0, q is 7, m is 3 and R is COOH;
p is 7, q is 1, m is 3 and R is COOH;
p is 0, q is 8, m is 3 and R is COOH;
p is 6, q is 1, m is 5 and R is COOH;
p is 0, q is 7, m is 5 and R is COOH;
p is 7, q is 1, m is 5 and R is COOH;
p is 0, q is 8, m is 5 and R is COOH;
p is 0, q is 8, m is 3 and R is OH;
p is 0, q is 8, m is 4 and R is COOH;
p is 0, q is 8, m is 6 and R is COOH;
p is 0, q is 8, m is 4 and R is OH;
p is 0, q is 7, m is 4 and R is COOH;
p is 0, q is 7, m is 6 and R is COOH;
p is 0, q is 7, m is 7 and R is COOH;
p is 0, q is 7, m is 3 and R is OH;
p is 5, q is 1, m is 6 and R is COOH;
p is 0, q is 6, m is 5 and R is COOH;
p is 6, q is 1, m is 6 and R is COOH;
p is 6, q is 1, m is 4 and R is OH;
p is 7, q is 1, m is 6 and R is COOH; or
p is 7, q is 1, m is 4 and R is OH, or pharmaceutically acceptable salts or esters of any of these substituted cyclodextrins. In a preferred embodiment, said substituted cyclodextrin is not 6-Per-deoxy-6-per-(5-carboxypentyl)thio-γ-cyclodextrin sodium salt, 6-Per-deoxy-G-per-3-carboxypropyl)thio-γ-cyclodextrin sodium salt or 6-Per-deoxy-6-per-(3-carboxypropyl)thio-β-cyclodextrin sodium salt. In another further preferred embodiment said pharmaceutically acceptable salt is not a sodium salt.

More preferably, a substituted cyclodextrin according to the invention or for use according to the invention is a cyclodextrins of formula (II) wherein:
p is 0, q is 8, m is 5 and R is COOH,
p is 0, q is 8, m is 4 and R is COOH,
p is 0, q is 8, m is 6 and R is COOH,
p is 0, q is 8, m is 4 and R is OH,
p is 0, q is 8, m is 3 and R is COOH
p is 0, q is 7, m is 7 and R is COOH,
p is 0, q is 7, m is 3 and R is OH,
p is 0, q is 6, m is 6 and R is COOH,
p is 6, q is 1, m is 6 and R is COOH,
p is 6, q is 1 m is 4 and R is OH, or
p is 7, q is 1, m is 4 and R is OH,
or a pharmaceutically acceptable salt or ester of any of these substituted cyclodextrins. In a preferred embodiment, said substituted cyclodextrin is not 6-Per-deoxy-6-per-(5-carboxypentyl)thio-γ-cyclodextrin sodium salt or 6-Per-deoxy-6-per-3-carboxypropyl)thio-γ-cyclodextrin sodium salt. In another further preferred embodiment said pharmaceutically acceptable salt is not a sodium salt.

In a further preferred embodiment, a substituted cyclodextrin according to the invention or for use according to the invention is a cyclodextrin wherein:
p is 0, q is 8, m is 5 and R is COOH,
p is 0, q is 6, m is 5 and R is COOH,
p is 6, q is 1, m is 6 and R is COOH,
p is 7, q is 1, m is 3 and R is COOH,
p is 6, q is 1, m is 6 and R is COOH,
p is 6, q is 1, m is 4 and R is OH, or
p is 7, q is 1, m is 4 and R is OH,
or a pharmaceutically acceptable salt or ester of any of these substituted cyclodextrins. In a preferred embodiment, said substituted cyclodextrin is not 6-Per-deoxy-6-per-(5-carboxypentyl)thio-γ-cyclodextrin sodium salt or 6-Per-deoxy-6-per-3-carboxypropyl)thio-γ-cyclodextrin sodium salt. In another further preferred embodiment said pharmaceutically acceptable salt is not a sodium salt.

In another further preferred embodiment, a substituted cyclodextrin according to the invention or for use according to the invention is a cyclodextrin wherein:
p is 0, q is 6, m is 5 and R is COOH,
p is 6, q is 1, m is 6 and R is COOH,
p is 7, q is 1, m is 3 and R is COOH,
p is 6, q is 1, m is 6 and R is COOH,
p is 6, q is 1, m is 4 and R is OH, or
p is 7, q is 1, m is 4 and R is OH,
or a pharmaceutically acceptable salt or ester of any of these substituted cyclodextrins.

A particularly preferred substituted cyclodextrin according to the invention or for use according to the invention is a cyclodextrin of formula (II) wherein p is 0, q is 8, m is 5 and R is COOH or an ester thereof, preferably a cyclodextrin wherein of formula (II) p is 0, q is 8, m is 5 and R is COOH. Another particularly preferred cyclodextrin according to the invention or for use according to the invention is a cyclodextrin of formula (II), wherein p is 0, q is 6, m is 5 and R is COOH or a pharmaceutically acceptable salt or ester thereof, preferably a cyclodextrin of formula (II) wherein p is 0, q is 6, m is 5 and R is COOH.

Salts of substituted cyclodextrins according to the invention are also provided. Such salts can be used as procoagulants in the methods and uses of the invention. Such salts include, but are not limited to, acid addition salts and base addition salts. The term "pharmaceutically acceptable salt" as used herein refers to those salts retain the pharmacological activity of the substituted cyclodextrins and that are, within the scope of sound medical judgment, suitable for use in humans or animals without undue toxicity, irritation, allergic response, and the like, and are commensurate with a reasonable benefit/risk ratio. Pharmaceutically acceptable salts are well-known in the art. They can be prepared in situ when isolating and purifying the substituted cyclodextrins of the invention, or separately by reacting them with pharmaceutically acceptable non-toxic bases or acids, including inorganic or organic bases and inorganic or organic acids, for instance by reacting the free acid or free base forms of the product with one or more equivalents of the appropriate acid or base in a solvent or medium in which the salt is insoluble, or in a solvent such as water or an organic solvent which is then removed in vacuo or by freeze-drying, or by exchanging the cations of an existing salt for another cation on a suitable ion exchange resin. Examples of pharmaceutically acceptable acids and bases include organic and inorganic acids such as acetic acid, propionic acid, lactic acid, glycolic acid, oxalic acid, pyruvic acid, succinic acid, maleic acid, malonic acid, trifluoroacetic acid, cinnamic acid, sulfuric acid, hydrochloric acid, hydrobromic acid, nitric acid, perchloric acid and phosphoric acid, and bases such as ethylamine, methylamine, dimethylamine, triethylamine, isopropylamine, diisopropylamine, and other mono-, di- and trialkylamines, and arylamines, and sodium salts, potassium salts and lithium salts.

Esters of substituted cyclodextrins according to the invention are also provided. Such esters can be used as procoagulants in the methods and uses of the invention. Compounds containing an ester group or bond are a well known as prodrugs for a compound containing a carboxylic acid. Such esters are activated by an esterase in vivo after administration to a patient. Such ester is preferably a cyclodextrin as defined herein wherein R is —COO(1-4C)alkyl, preferably —COO(1-2C)alkyl.

Also provided is a pharmaceutical composition comprising a substituted cyclodextrin according to the invention or pharmaceutically acceptable salt or ester thereof and at least one pharmaceutically acceptable auxiliary. Examples of a pharmaceutically acceptable auxiliary include a pharmaceutically acceptable carrier, diluent and/or excipient. By "pharmaceutically acceptable" it is meant that the auxiliary, carrier, diluent or excipient must be compatible with the other ingredients of the formulation and not deleterious to the recipient thereof. In general, any pharmaceutically suitable additive which does not interfere with the function of the active compounds can be used. A pharmaceutical composition according to the invention is preferably suitable for human use. Examples of suitable carriers comprise a solution, lactose, starch, cellulose derivatives and the like, or mixtures thereof. In a preferred embodiment said suitable carrier is a solution, for example saline. For making dosage units, e.g. tablets, the use of conventional additives such as fillers, colorants, polymeric binders and the like, is contemplated. Examples of excipients which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. Compositions for intravenous administration may for example be solutions comprising the antibodies of the invention in sterile isotonic aqueous buffer. The intravenous compositions may include for instance solubilizing agents, stabilizing agents and/or a local anesthetic to ease the pain at the site of the injection.

In one embodiment, a pharmaceutical composition according to the invention is formulated from systemic administration, preferably for parenteral administration, including but not limited to intravenous, intramuscular and subcutaneous administration, or for oral administration, including but not limited to tablets, capsules, liquids, emulsions, suspensions.

A pharmaceutical composition according to the invention is preferably suitable for topical administration, for topical (local) treatment of bleeding. A pharmaceutical composition is therefore preferably formulated for topical administration, preferably as a gel, cream, ointment, spray, mouth wash, eye drops, dressing, compress, plaster, band-aid or patch. Such topical formulations are particularly suitable for use in treatment of a wound and/or local (major) bleeding.

Further provided is a kit of parts comprising:
a substituted cyclodextrin or pharmaceutically acceptable salt or ester thereof according to the invention, and
a recombinant or isolated coagulation factor.

The term "isolated recombinant coagulation factor" refers to a coagulation that is recombinantly produced or isolated from blood or plasma. Preferred, but not limiting, coagulation factors are factor V, factor VII, factor VIII, factor IX, factor X, factor XI, factor XIII, alpha2-antiplasmin, von Willebrand factor. Particularly preferred are factor VIII and factor IX. Preferably, a coagulation factor present in a kit of parts according to the invention is recombinant coagulation factor.

Such kit of parts is particularly suitable to provide a combination therapy for treatment of patients that are deficient in a coagulation factor, such as patients suffering from hemophilia A, hemophilia B, Von Willebrand disease or hemophilia C. The use of such kit of parts has the advantage that less isolated or recombinant coagulation factor is needed for treatment of such patients.

In a preferred embodiment, a kit of parts according to the invention comprises factor VIII as the recombinant or isolated coagulation factor and a substituted cyclodextrin selected from the group of cyclodextrins of formula (II) wherein:
p is 0, q is 8, m is 5 and R is COOH,
p is 0, q is 8, m is 4 and R is COOH,
p is 0, q is 8, m is 6 and R is COOH,
p is 0, q is 8, m is 4 and R is OH,
p is 0, q is 7, m is 7 and R is COOH,
p is 0, q is 7, m is 3 and R is OH,
p is 0, q is 6, m is 5 and R is COOH,
p is 6, q is 1, m is 6 and R is COOH,
p is 6, q is 1 m is 4 and R is OH or
p is 7, q is 1, m is 4 and R is OH,
or a pharmaceutically acceptable salt or ester thereof.

In another preferred embodiment, a kit of parts according to the invention comprises factor IX as the recombinant or isolated coagulation factor and a substituted cyclodextrin selected from the group of cyclodextrins of formula (II) wherein:
p is 0, q is 8, m is 5 and R is COOH,
p is 0, q is 8, m is 6 and R is COOH,
p is 0, q is 8, m is 4 and R is OH,
p is 0, q is 7, m is 7 and R is COOH,
p is 0, q is 7, m is 3 and R is OH,
p is 6, q is 1, m is 6 and R is COOH,
p is 6, q is 1 m is 4 and R is OH or
p is 7, q is 1, m is 4 and R is OH,
or a pharmaceutically acceptable salt or ester thereof.

In another preferred embodiment, a kit of parts according to the invention comprises factor X1 as the recombinant or isolated coagulation factor and a substituted cyclodextrin is a cyclodextrin of formula (II) wherein p is 0, q is 8, m is 5 and R is COOH or a pharmaceutically acceptable salt or ester thereof.

In one embodiment of the invention, a kit of parts is provided comprising one or more containers filled with a substituted cyclodextrin or pharmaceutically acceptable salt or ester thereof according to the invention and a recombinant or isolated coagulation factor. Associated with such containers can be various written materials such as instructions for use, or a notice in the form prescribed by a governmental agency regulating the manufacture, use or sale of pharmaceuticals products, which notice reflects approval by the agency of manufacture, use, or sale for human or veterinary administration. Preferably, a kit of parts according to the invention comprises instructions for use.

As used herein, the term "coagulation" refers to the process of polymerization of fibrin monomers, resulting in the formation of a blood clot, whereby blood or plasma changes from a liquid to a gel phase. As used herein, the term "use as procoagulant" refers to initiating or accelerating the process of blood clot formation. Any methods known in the art can be used for determining procoagulant effect of a substituted cyclodextrin as described herein, e.g. measuring thrombin generation and/or the length of time before blood clot formation in plasma or blood samples. A particularly suitable method is described in the Examples herein for measuring thrombin generation. In brief, normal plasma is spiked with cyclodextrin and optionally with an anticoagulant. Coagulation is triggered by recalcification in the presence of, e.g. recombinant human, tissue factor and fluorogenic substrate Z-Gly-Gly-Arg-AMC. Fluorescence can be monitored and followed by calculation of lag time for thrombin formation, peak thrombin, velocity index and area under the curve.

Also provided is the use of a substituted cyclodextrin comprising at least one substituent —S—($C_n$alkylene)-R, wherein n is an integer from 3 to 10, preferably 3 to 7, and R is selected from the group consisting of —COOH, —OH, and —COO(1-4C)alkyl, or a pharmaceutically acceptable salt thereof as a procoagulant. Also provided is a method for procoagulation comprising administering to a subject in need thereof, a therapeutically effective amount of a substituted cyclodextrin comprising at least one substituent —S—($C_n$alkylene)-R, wherein n is an integer from 3 to 10 and R is selected from the group consisting of —COOH, —OH, and —COO(1-4C)alkyl, or a pharmaceutically acceptable salt thereof. Also provided is a method for inducing or stimulating coagulation in a subject in need thereof comprising administering to the subject a therapeutically effective amount of a substituted cyclodextrin comprising at least one substituent —S—($C_n$alkylene)-R, wherein n is an integer from 3 to 10 and R is selected from the group consisting of —COOH, —OH, and —COO(1-4C)alkyl, or a pharmaceutically acceptable salt thereof.

The cyclodextrins described herein are particularly suitable for reversing the anticoagulant effect of an anticoagulant, i.e. as an antidote for anticoagulants. As demonstrated in the Examples, the substituted cyclodextrins were capable of reversing the anticoagulant activity of all anticoagulants tested. Provided is therefore a substituted cyclodextrin according to the invention or pharmaceutically acceptable salt or ester thereof for use in a method for reversing an anticoagulant effect of an anticoagulant in a subject. Also provided is a method for reversing an anticoagulant effect of an anticoagulant in a subject in need thereof, the method comprising administering to the subject, which subject has been administered said anticoagulant, a therapeutically effective amount of a substituted cyclodextrin according to the invention or pharmaceutically acceptable salt or ester thereof. Further provided is substituted cyclodextrin according to the invention or pharmaceutically acceptable salt or ester thereof for the preparation of a medicament for reversing an anticoagulant effect of an anticoagulant in a subject.

The term "anticoagulant" as used herein refers to an agent or compound capable of preventing or delaying blood clot formation in vitro and/or in vivo.

As used herein, the term "reversing an anticoagulation effect of an anticoagulant" refers to decreasing the ability of the anticoagulant to prevent or delay blood clot formation. Hence, the anticoagulation effect of the anticoagulant is at least partially reversed. In particular, the term refers to a shortening of the time to initiation of blood clot formation or to an increase in strength of the blood clot in the presence of a substituted cyclodextrin as described herein and an anticoagulant as compared to the time to initiation to blood clot formation or strength of blood clot in the presence of the anticoagulant but in the absence of the substituted cyclodextrin. Any methods known in the art can be used for determining procoagulant effect of a substituted cyclodextrin as described herein, e.g. measuring thrombin generation, blood clot strength and/or the length of time before clot formation in plasma or blood samples or in an in vivo bleeding model. A suitable thrombin formation assay is described in the Examples and above. A suitable in vive bleeding assay is also described in the Examples. In brief, the saphenous veins in the hind limb of anesthetized mice are transected by piercing with a needle followed by an incision. Blood is gently wicked away until haemostasis occurs. The clot is then removed and blood is again wicked away until haemostasis, which is repeated for 30 minutes. Parameters that can be assessed are the number of times that haemostasis occurs in 30 minutes and the time required for each haemostasis.

The anticoagulant can be any anticoagulant known in the art, since the cyclodextrins according to the invention have demonstrable activity against all tested anticoagulants. In a preferred embodiment, the anticoagulant is selected from the group consisting of:
- a direct thrombin inhibitor, such as dabigatran, hirudin, bivalirudin, lepirudin or argatroban,
- a direct factor Xa inhibitor, such as rivaroxaban, apixaban, edoxaban, betrixaban, darexaban, letaxaban or eribaxaban,
- a pentasaccharide, such as fondaparinux or idraparinux,
- a low molecular weight heparins, such as nadroparin, tinzaparin, dalteparin, enoxaparin, bemiparin, reviparin, parnaparin or certoparin,
- unfractionated heparin,
- a vitamin K antagonist, such as acenocoumarol, phenprocoumon, warfarin, atromentin or phenindione, and
- an antiplatelet drug, such as an irreversible cyclooxygenase inhibitors (such as aspirin or a derivative thereof or triflusal), an ADP receptor inhibitor (such as clopidogrel, prasugrel, ticagrelor, ticlopedine, cangrelor or elinogrel), a phosphodiesterase inhibitor (such as cilostazol), a PAR-1 antagonist (such as voraxapar), a GPIIB/IIIa inhibitor (such as abciximab, eptifibatide, tirofiban, roxifiban or orbofiban), an adenosine reuptake inhibitor (such as dipyridamole), a thromboxane inhibitor (such as ifetroban or picotamide) or a thromboxane receptor antagonist (such as terutroban or picotamide).

It is noted that this list is non-exhaustive, many other anticoagulants belonging to the listed categories of anticoagulants are known to a person skilled in the art. Their anticoagulant effects can also be reversed using the substituted cyclodextrins of the invention. In a specific embodiment of the invention, the anticoagulant is selected from the group consisting of dabigatran, rivaroxaban, apixaban, edoxaban, fondaparinux, nadroparin, tinzaparin, unfractionated heparin, hirudin, bivalirudin and a vitamin K antagonist. In one preferred embodiment, the anticoagulant is selected from the group consisting of dabigatran, rivaroxaban, apixaban and edoxaban.

In a preferred embodiment, the substituted cyclodextrin used according to the invention for reversing an anticoagulant effect of an anticoagulant in a subject is selected from the group consisting of OKL-1105, OKL-1106, OKL-1107, OKL-1108, OKL-1109, OKL-1110, OKL-1111, OKL-1146, OKL-1171, OKL-1172, OKL-1174, OKL-1178, OKL-1180, OKL-1181, OKL-1186, OKL-1187, OKL-1188, OKL-1189, OKL-1190, OKL-1191, the structures of which are indicated in table 1, and combinations thereof, more preferably selected from the group consisting of OKL-1105, OKL-1106, OKL-1107, OKL-1108, OKL-1110, OKL-1111, OKL-1146, OKL-1171, OKL-1172, OKL-1174, OKL-1178, OKL-1180, OKL-1181, OKL-1186, OKL-1187, OKL-1188, OKL-1189, OKL-1190, OKL-1191 and combinations thereof. In a particularly preferred embodiment, the substituted cyclodextrin used according to the invention for reversing an anticoagulant effect of an anticoagulant in a subject is OKL-1111, a per-substituted γ-cyclodextrin of formula (II), wherein the substituent is —S—(CH$_2$)$_5$—COOH or a pharmaceutically acceptable salt or ester thereof, or OKL-1187, a per-substituted α-cyclodextrin of formula (II), wherein the substituent is —S—(CH$_2$)$_5$—COOH or a pharmaceutically acceptable salt or ester thereof.

Whether or not the effect of a particular anticoagulant can be reversed with a particular substituted cyclodextrin of the invention can be readily assessed by a skilled person, for instance by performing a coagulation assay as described in the Examples herein. In such assay, normal human plasma containing the anticoagulant is incubated with and without the substituted cyclodextrin and one or more of the parameters as described herein (lag time for thrombin formation, peak thrombin, velocity index and area under the curve) are determined to assess whether the substituted cyclodextrin is able to reverse the anticoagulant effect in the specific plasma sample.

The Examples further show that the cyclodextrins of the invention have a procoagulant effect in plasma of patients that are deficient in one of the coagulation factors. The cyclodextrins of the invention are therefore further particularly suitable for antagonizing blood coagulation disorders, i.e. as prohemostatic agents. Provided is therefore a substituted cyclodextrin according to the invention or a pharmaceutically acceptable salt or ester thereof for use in a method for the treatment or prevention of a blood coagulation disorder. Also provided is a method for the treatment or prevention of a blood coagulation disorder, comprising administering to a subject in need thereof a therapeutically effective amount of a substituted cyclodextrin according to the invention or a pharmaceutically acceptable salt or ester thereof. Also provided is a substituted cyclodextrin according to the invention or a pharmaceutically acceptable salt or ester thereof for the preparation of a medicament for the treatment or prevention of a blood coagulation disorder.

As used herein, the term "blood coagulation disorder" refers to a disease which causes an anomaly in the hemostatic and/or coagulation system. Such disorder is typically characterized by a tendency to bleeding. Well known examples of blood coagulation disorders include hemophilia A, which is characterized by a deficiency of coagulation factor VIII (FVIII), hemophilia B, which is characterized by a deficiency of coagulation factor IX (FIX) and hemophilia C, which is characterized by a deficiency of coagulation factor XI (FXI). Whether or not a particular blood coagulation disorder is treatable with a particular substituted cyclodextrin of the invention is can be readily assessed by a skilled person, for instance by performing a coagulation assay as described in the Examples herein. In such assay, plasma of one or more patients suffering from the blood coagulation disorder is incubated with and without the substituted cyclodextrin and one or more of the parameters as described herein (lag time for thrombin formation, peak thrombin, velocity index and area under the curve) are determined to assess whether the substituted cyclodextrin has a procoagulant effect in the specific plasma sample. Preferred, but non-limiting, examples of blood coagulation disorders are congenital or acquired hemophilia A, hemophilia B, hemophilia C, von Willebrand disease, coagulation factor deficiency, such as factor V, factor VII, and/or factor X deficiency, factor XIII or alpha2-antiplasmin deficiency, hereditary or drug-induced thrombocytopenia, including immune thrombocytopenia purpura, thrombotic thrombocytopenic purpura, fetal or neonatal alloimmune thrombocytopenia and post-transfusion thrombocytopenic purpura, Wiskott-Aldrich Syndrome, Glanzmann's thrombasthenia, Bernard-Soulier Syndrome, idiopathic dense-granule disorder, Hermansky-Pudlak syndrome, Chediak-Higashi syndrome, gray platelet syndrome. Paris-Trousseau/Jacobsen's syndrome, disseminated intravascular coagulation and vitamin K deficiency, including vitamin K deficiency of the newborn. In a preferred embodiment of the invention, the blood coagulation disorder is selected from the group consisting of said disorders. In a further preferred embodiment, said disorder is deficiency of a coagulation factor deficiency, in particular deficiency of a coagulation factor selected from the group consisting of factor V, factor VII, factor VIII, factor IX, factor X, factor XI, factor XIII and alpha2-antiplasmin. Particularly preferred disorders that is treated or prevented in accordance with the invention is selected from the group consisting of hemophilia A, hemophilia B and hemophilia C.

In a preferred embodiment, the substituted cyclodextrin used according to the invention for treatment or prevention of a blood coagulation disorder, preferably hemophilia A, hemophilia B or hemophilia C, is selected from the group consisting of OKL-1111, OKL-1171, OKL-1172, OKL-1174, OKL-1180, OKL-1181, OKL-1187, OKL-1188, OKL-1189, OKL-1191, preferably selected from the group consisting of OKL-1111, OKL-1172, OKL-1180, OKL-1187, OKL-1188, OKL-1189 and OKL-1191, preferably selected from the group consisting of OKL-1111, OKL-1180 and OKL-1187, the structures of which are indicated in table 1, and combinations thereof. In a further preferred embodiment, the substituted cyclodextrin used according to the invention for treatment or prevention of a blood coagulation disorder, preferably hemophilia A, hemophilia B or hemophilia C, is a substituted cyclodextrin of formula (I), wherein m is an integer from 5 to 10, more preferably from 5 to 7, more preferably 5, p is 0 and q is 7 or 8. In a particularly preferred embodiment, the substituted cyclodextrin used according to the invention for treatment or prevention of a blood coagulation disorder, preferably hemophilia A, hemophilia B or hemophilia C, is selected from the group consisting of OKL-1111, OKL-1172, OKL-1180, OKL-1187, OKL-1188, OKL-1189 en OKL1191, or mixtures thereof, preferably OKL-1111, a per-substituted γ-cyclodextrin of formula (IT), wherein the substituent is —S—(CH$_2$)$_5$—COOH or a pharmaceutically acceptable salt or ester thereof.

In a preferred embodiment the blood coagulation disorder is hemophilia A and the substituted cyclodextrin is a cyclodextrin of formula (II) wherein:
p is 0, q is 8, m is 5 and R is COOH,
p is 0, q is 8, m is 4 and R is COOH,
p is 0, q is 8, m is 6 and R is COOH,
p is 0, q is 8, m is 4 and R is OH,
p is 0, q is 7, m is 7 and R is COOH,
p is 0, q is 7, m is 3 and R is OH,
p is 0, q is 6, m is 5 and R is COOH,
p is 6, q is 1, m is 6 and R is COOH,
p is 6, q is 1 m is 4 and H is OH or
p is 7, q is 1, m is 4 and R is OH,
or a pharmaceutically acceptable salt or ester of any of these substituted cyclodextrins.

In another preferred embodiment the blood coagulation disorder is hemophilia B and the substituted cyclodextrin is a cyclodextrin of formula (II) wherein:
p is 0, q is 8, m is 5 and R is COOH,
p is 0, q is 8, m is 6 and R is COOH,
p is 0, q is 8, m is 4 and R is OH, p is 0, q is 7, m is 7 and R is COOH,
p is 0, q is 7, m is 3 and R is OH,
p is 6, q is 1, m is 6 and R is COOH,
p is 6, q is 1 m is 4 and H is OH or
p is 7, q is 1, m is 4 and R is OH,
or a pharmaceutically acceptable salt or ester of any of these substituted cyclodextrins.

In another preferred embodiment the blood coagulation disorder is hemophilia C and the substituted cyclodextrin is a cyclodextrin of formula (II) wherein p is 0, q is 8, m is 5 and R is COOH or a pharmaceutically acceptable salt or ester thereof.

The Examples further show that the cyclodextrins of the invention have a procoagulant effect in normal plasma both in the presence and absence of an anticoagulant. Hence, the cyclodextrins of the invention are also particularly suitable for reducing or preventing bleeding in a subject, i.e. as prohemostatic agents in a bleeding situation, irrespective of the cause of bleeding. Further provided is therefore a substituted cyclodextrin according to the invention or a pharmaceutically acceptable salt or ester thereof for use in a method for reducing or preventing bleeding in a subject. Also provided is a method for reducing or preventing bleeding in a subject in need thereof, the method comprising administering to the subject a therapeutically effective amount of a substituted cyclodextrin according to the invention or a pharmaceutically acceptable salt or ester thereof. Also provided is a substituted cyclodextrin according to the invention or a pharmaceutically acceptable salt or ester thereof for the preparation of a medicament for reducing or preventing bleeding in a subject.

Preferably, said subject has been treated with an anticoagulant, is undergoing surgery, is undergoing dental treatment, is suffering from trauma, is suffering from induced or spontaneous major bleeding, such as intracranial or gastrointestinal bleeding, and/or is suffering from or at risk of hereditary or drug-induced thrombocytopenia.

The anticoagulant can be any anticoagulant known in the art, since the cyclodextrins according to the invention have demonstrable activity against all tested anticoagulants. In a preferred embodiment, the anticoagulant is selected from the group consisting of:
- a direct thrombin inhibitor, such as dabigatran, hirudin, bivalirudin, lepirudin or argatroban,
- a direct factor Xa inhibitor, such as rivaroxaban, apixaban, edoxaban, betrixaban, darexaban, letaxaban or eribaxaban,
- a pentasaccharide, such as fondaparinux or idraparinux.
- a low molecular weight heparin, such as nadroparin, tinzaparin, dalteparin, enoxaparin, bemiparin, reviparin, parnaparin or certoparin,
- unfractionated heparin,
- a vitamin K antagonist, such as acenocoumarol, phenprocoumon, warfarin, atromentin or phenindione, and
- an antiplatelet drug, such as an irreversible cyclooxygenase inhibitors (such as aspirin or a derivative thereof or triflusal), an ADP receptor inhibitor (such as clopidogrel, prasugrel, ticagrelor, ticlopedine, cangrelor or elinogrel), a phosphodiesterase inhibitor (such as cilostazol), a PAR-1 antagonist (such as voraxapar), a GPIIB/IIIa inhibitor (such as abciximab, eptifibatide, tirofiban, roxifiban or orbofiban), an adenosine reuptake inhibitor (such as dipyridamole), a thromboxane inhibitor (such as ifetroban or picotamide) or a thromboxane receptor antagonist (such as terutroban or picotamide).

It is noted that this list is non-exhaustive, many other anticoagulants belonging to the listed categories of anticoagulants of which the effects can be reversed with the methods or used of the invention are known to a person skilled in the art. In a specific embodiment of the invention, the anticoagulant is selected from the group consisting of dabigatran, rivaroxaban, apixaban, edoxaban, fondaparinux, nadroparin, tinzaparin, unfractionated heparin, hirudin, bivalirudin and a vitamin K antagonist.

In a preferred embodiment, the substituted cyclodextrin used according to the invention for reducing or preventing bleeding in a subject is selected from the group consisting of a cyclodextrin of formula (II) wherein:
p is 0, q is 7, m is 3 and R is COOH;
p is 7, q is 1, m is 3 and R is COOH;
p is 0, q is 8, m is 3 and R is COOH;
p is 6, q is 1, m is 5 and R is COOH;
p is 0, q is 7, m is 5 and R is COOH;
p is 7, q is 1, m is 5 and R is COOH;
p is 0, q is 8, m is 5 and R is COOH;
p is 0, q is 8, m is 3 and R is OH;
p is 0, q is 8, m is 4 and R is COOH;
p is 0, q is 8, m is 6 and H is COOH;
p is 0, q is 8, m is 4 and R is OH;
p is 0, q is 7, m is 4 and R is COOH;
p is 0, q is 7, m is 6 and R is COOH;
p is 0, q is 7, m is 7 and R is COOH;
p is 0, q is 7, m is 3 and R is OH;
p is 5, q is 1, m is 5 and R is COOH;
p is 0, q is 6, m is 5 and H is COOH;
p is 6, q is 1, m is 6 and R is COOH;
p is 6, q is 1, m is 4 and R is OH;
p is 7, q is 1, m is 6 and R is COOH; or
p is 7, q is 1, m is 4 and R is OH,
or a pharmaceutically acceptable salt or ester thereof, more preferably selected from the group consisting of OKL-1105, OKL-1106, OKL-1107, OKL-1108, OKL-1109, OKL-1110, OKL-1111, OKL-1146, OKL-1171, OKL-1172, OKL-1174, OKL-1178, OKL-1180, OKL-1181, OKL-1186, OKL-1187, OKL-1188, OKL-1189, OKL-1190, OKL-1191 or a pharmaceutically acceptable salt or ester thereof and combinations thereof, more preferably selected from the group consisting of OKL-1105, OKL-1106, OKL-1107, OKL-1110, OKL-1111, OKL-1146, OKL-1172, OKL-1174, OKL-1180, OKL-1181, OKL-1187, OKL-1188, OKL-1189, OKL-1191 or a pharmaceutically acceptable salt or ester thereof and combinations thereof, more preferably selected from the group consisting of OKL-1106, OKL-1107, OKL-1111, OKL-1146, OKL-1172, OKL-1174, OKL-1180, OKL-1187, OKL-1188, OKL-1189, OKL-1191 or a pharmaceutically acceptable salt or ester thereof and combinations thereof, more preferably selected from the group consisting of OKL-1106, OKL-1111, OKL-1174 OKL-1187, OKL-1188, OKL-1189, OKL-1191 or a pharmaceutically acceptable salt or ester thereof and combinations thereof. In a further preferred embodiment, the substituted cyclodextrin used according to the invention for reducing or preventing bleeding in a subject is a substituted cyclodextrin of formula (II), wherein m is an integer from 5 to 10, more preferably from 5 to 7, more preferably 5, p is 0 and q is 7 or 8. In a particularly preferred embodiment, the substituted cyclodextrin used according to the invention for reducing or preventing bleeding in a subject is OKL-1111, a per-substituted γ-cyclodextrin of formula (II), wherein the substituent is —S—$(CH_2)_5$—COOH or a pharmaceutically acceptable salt or ester thereof, or OKL-1187, a per-substituted α-cyclodextrin of formula (II), wherein the substituent is —S—(CH$_2$)$_5$—COOH or a pharmaceutically acceptable salt or ester thereof.

The term "therapeutically effective amount" as used herein refers to the amount of the pharmaceutical composition, which provides a therapeutic benefit in the prevention, treatment, or management, of the disease being treated.

As used herein, the term "subject" encompasses humans and animals, preferably mammals. Preferably, a subject is a mammal, more preferably a human. In a particular embodiment, a subject is a patient that has been treated with an anticoagulant, is suffering from a blood coagulation disorder, is undergoing surgery, is undergoing dental treatment, is suffering from trauma, is suffering from induced or spontaneous major bleeding, such as intracranial or gastro-intestinal bleeding, and/or is suffering from or at risk of hereditary or drug-induced thrombocytopenia.

As used herein, the term "prevention" refers to preventing or delaying the onset of a disease and/or the appearance of clinical symptoms of the disease in a subject that does not yet experience clinical symptoms of the disease. The term "treatment" refers to inhibiting the disease, i.e., halting or reducing its development or at least one clinical symptom thereof, and to relieving symptoms of the disease.

The substituted cyclodextrins described herein can be prepared using any method known in the art for the preparation of cyclodextrins. Particularly suitable methods for the preparation of substituted cyclodextrins, in particular substituted α-cyclodextrins, substituted β-cyclodextrins and substituted γ-cyclodextrins, starting from commercially available intermediate cyclodextrins and their purification are described in the Examples.

Features may be described herein as part of the same or separate aspects or embodiments of the present invention for the purpose of clarity and a concise description. It will be appreciated by the skilled person that the scope of the invention may include embodiments having combinations of all or some of the features described herein as part of the same or separate embodiments.

The invention will be explained in more detail in the following, non-limiting examples.

EXAMPLES

Example 1

Materials and Methods
Synthesis of Cyclodextrins
General Procedure for the Synthesis of Decorated β-Cyclodextrins with Thiols.

For the synthesis of mono-decorated β-cyclodextrin derivatives, a solution of 6-monotosyl-β-cyclodextrin (500 mg, 0.388 mmol, 1.0 equiv.) in DMSO (3 mL) was degassed. The solution was added dropwise to a degassed solution of the appropriate thiol (H—S—R: 4.67 mmol, 12 equiv) and NaOH (460 mg, 11.5 mmol, 30 equiv) in DMSO/H$_2$O (4 mL/2 mL). The suspension was stirred overnight at 50° C. The reaction mixture was allowed to cool to room temperature. Methanol (8 mL) was added. The white precipitate was filtered and washed with methanol. The precipitate was dissolved in H$_2$O (5 mL) and the pH was adjusted to 7 with aqueous 3 M HCl. The solution was poured into MeOH (8-16 mL) or acetone. The precipitate was filtered, washed with methanol or acetone and dried under reduced pressure.

The synthesis of per-decorated β-cyclodextrin derivatives with a sulfur tether was performed using commercial heptakis-(6-bromo-6-deoxy)-β-cyclodextrin as starting material. The reactions with the appropriate thiol (H—S—R) and NaOH were performed successfully with NaH as base in DMF with stirring overnight at room temperature.

Figure 31:
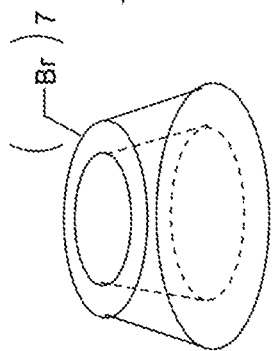
FIG. 31: A first reaction scheme described in Example 1 for the sulphur tethering of beta-cyclodextrins.
Figure 31:
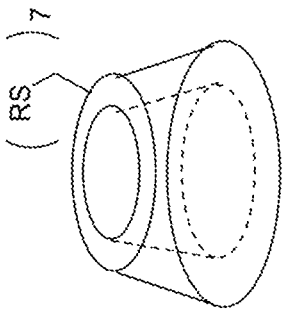

FIG. 31 shows the reaction for per-decorated β-cyclodextrin derivatives.

General Procedure for the Synthesis of Decorated γ-Cyclodextrins with Thiols.

For the synthesis of per-decorated γ-cyclodextrin derivatives a solution of Octakis-6-bromo-6-deoxy-γ-cyclodextrin (1.8 g, 1 mmol, 1.0 equiv.) in DMSO (9 mL) was degassed. The solution was added dropwise to a degassed solution of the appropriate thiol (12.5 mmol, 12.5 equiv) and NaOH (1.1 g, 27.5 mmol, 27 equiv) in DMSO/$H_2O$ (12 mL/6 mL). The suspension was stirred overnight at 50° C. The reaction mixture was allowed to cool to room temperature. Methanol (80 mL) was added. The white precipitate was filtered and washed with methanol. The precipitate was dissolved in $H_2O$ (50 mL) and the pH was adjusted to 7 with aqueous 3 M HCl. The solution was poured into EtOH (100 mL) or acetone. The precipitate was filtered, washed with methanol or acetone and dried under reduced pressure.

For the synthesis of mono-decorated γ-cyclodextrin derivatives, monotosylated γ-cyclodextrines were functionalized in a similar fashion as described for the mono-decorated beta-cyclodextrins.

Figure 32:
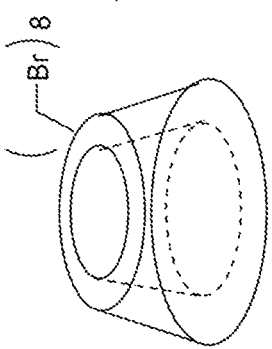
FIG. 32: A second reaction scheme described in Example 1 for the sulphur tethering of gamma-cyclodextrins is shown.
Figure 32:
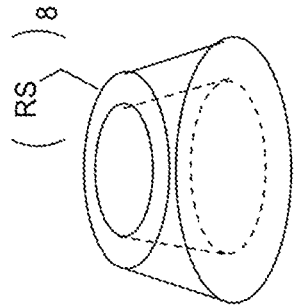

Analogous to the beta-cyclodextrins, the γ-cyclodextrins were functionalized (see FIG. 32 for the per-substituted γ-cyclodextrins). The compounds were synthesized using NaOH and DMSO as solvent, providing difficult isolations but eventually addition of EtOAc led to good precipitation.

Purification

In general, the functionalized cyclodextrins were isolated by precipitation from a suitable solvent, followed by several washings with solvents to remove excess of reagents and side-products. Often this procedure provided materials that were considered pure for the application based on either $^1$H NMR (often broad peaks or especially in the case of mono-substitution rather complex spectra were observed) or HPLC-MS or the combination of both. In a number of cases the reaction towards the decorated cyclodextrin had to be repeated to prepare a new batch in order to isolate pure product. In addition, other methods to purify cyclodextrins were made, including normal phase chromatography, reversed-phase chromatography and preparative-HPLC.

Synthesis of Decorated Alpha Cyclodextrins

Alpha-mono-S—C6-acid (OKL-1186) was prepared according to the general procedure described above using 6-Mercaptohexanoic acid (131 μl, 140 mg, 0.943 mmol), NaOH (38 mg, 0.0925 mmol) and 6-monodeoxy-6-monoiodo-α-cyclodextrin (200 mg, 0.185 mmol). Other alpha-mono-substituted cyclodextrins according to the invention can be prepared in the same way using the appropriate starting compounds.

Alpha-per-S—C6-acid (OKL-1187): Under a N2 atmosphere, NaH (70 mg, 1.70 mmol, 23.0 eq.) was suspended in DMF (5 mL). A solution of 6-mercaptohexanoic acid (134 mg, 0.897 mmol, 12.1 eq.) in DMF (2 mL) was added dropwise. After 10 minutes, hexakis-(6-bromo-6-deoxy)-α-cyclodextrin (102 mg, 0.0741 mmol, 1.0 eq.) was added and the reaction mixture was stirred at room temperature overnight. The reaction mixture was precipitated by addition of acetone (large excess), filtered and washed with acetone. The precipitate was dissolved in demi-water (5 mL) and the pH was adjusted to just below 7 with a 3 M HCl solution in demi-water. The resulting suspension was diluted with acetone, filtered, washed with acetone and dried in vacuo to give the product. Other alpha-per-substituted cyclodextrins according to the invention can be prepared in the same way using the appropriate starting compounds.

Figure 1:
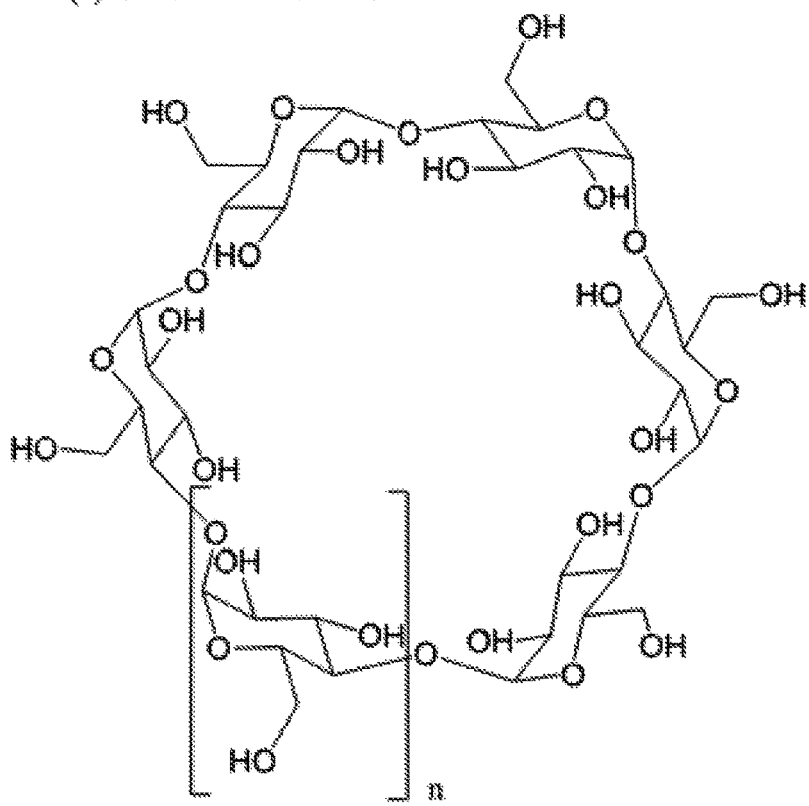
FIG. 1: Basic structure of α-, β- and γ-cyclodextrins. a. chemical structure; b. 3-D structure.
Figure 1:
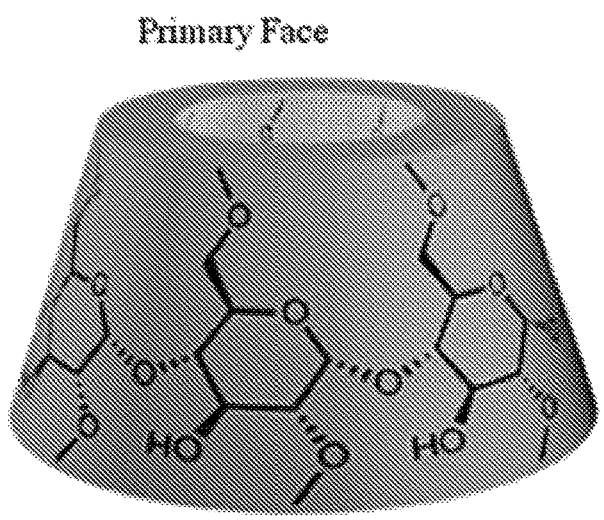
Figure 2:
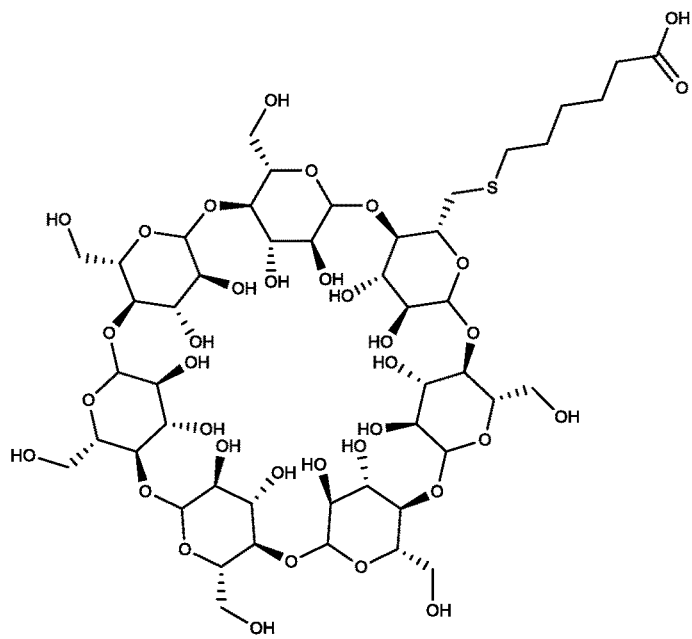
FIG. 2: Structures of OKL-1108 (A), OKL-1109 (B), OKL-1110 (C) and OKL-1111 (D).
Figure 2:
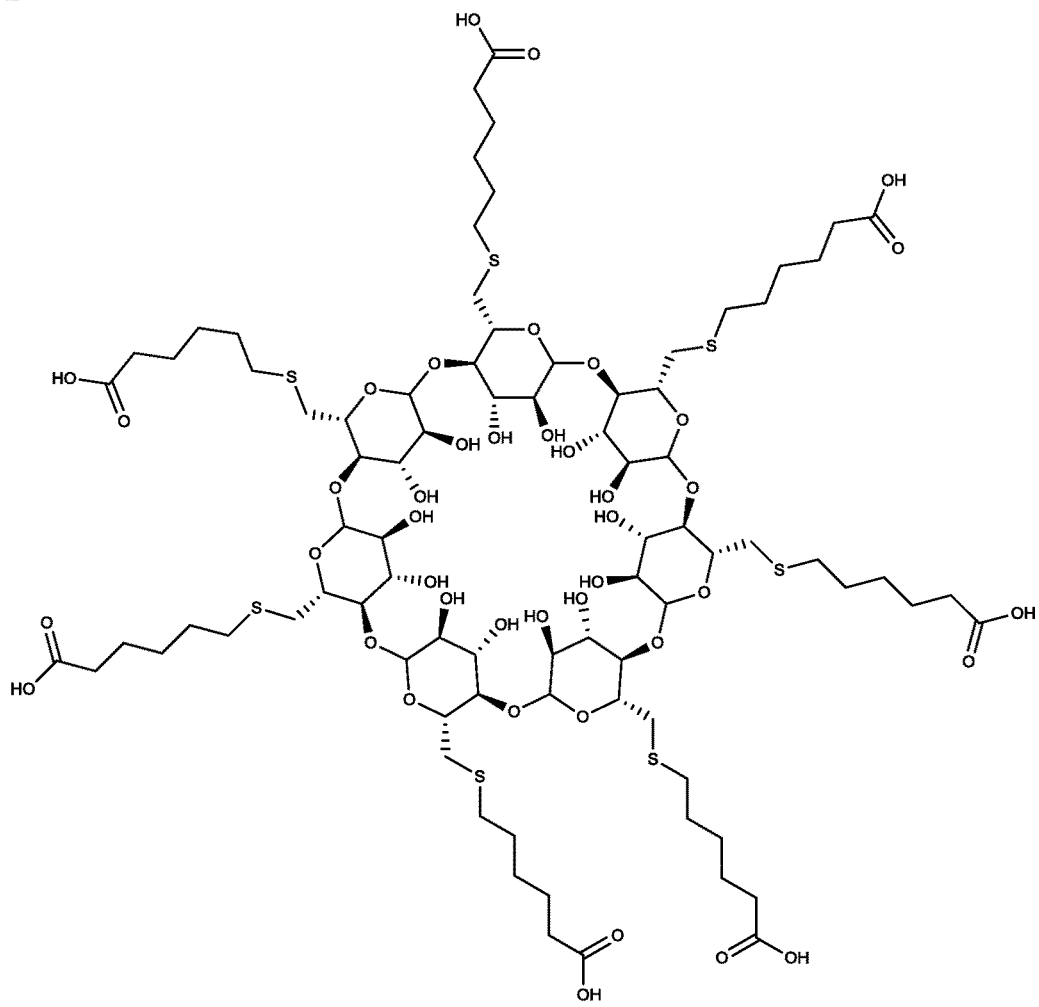
Figure 2:
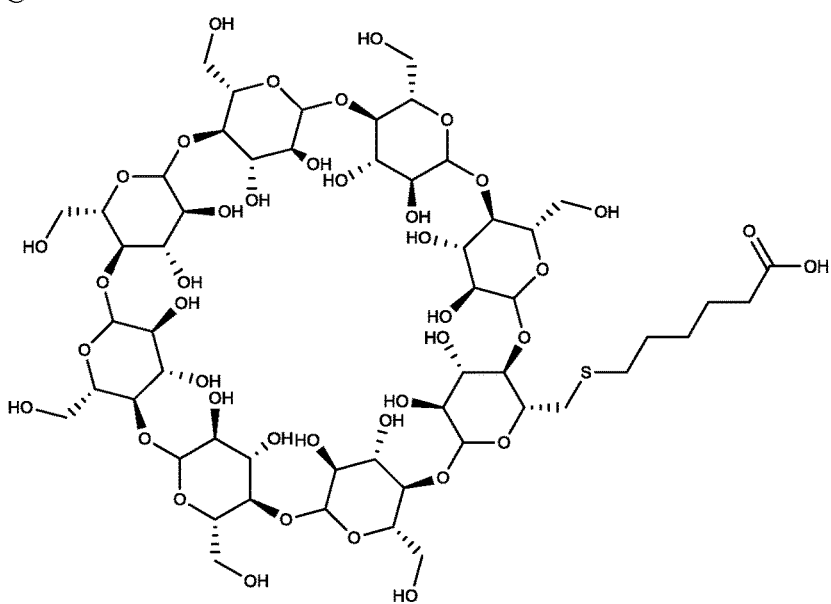
Figure 2:
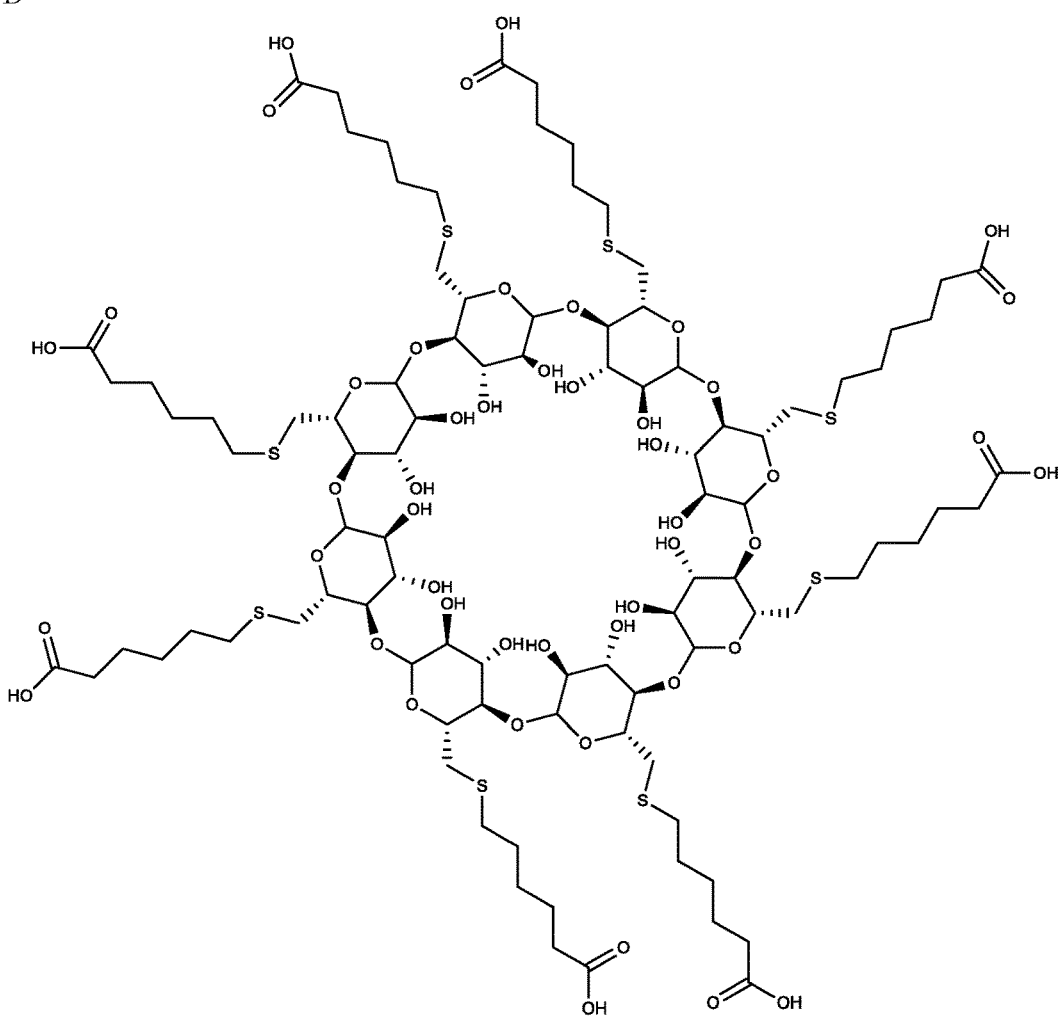

Tables 1 and 2 shows the cyclodextrins that have been prepared. FIG. 2 shows the structure of four exemplary mono- and per-substituted, beta- and gamma cyclodextrins (compounds OKL-1108, OKL-1109, OKL-1110 and OKL-1111).

TABLE 1

Cyclodextrins with procoagulant activity.

| compound | cyclodextrin type | substitution pattern | substituent |
|---|---|---|---|
| OKL-1105 | beta | per | —S—$(CH_2)_3$—COOH |
| OKL-1106 | gamma | mono | —S—$(CH_2)_3$—COOH |
| OKL-1107 | gamma | per | —S—$(CH_2)_3$—COOH |
| OKL-1108 | beta | mono | —S—$(CH_2)_5$—COOH |
| OKL-1109 | beta | per | —S—$(CH_2)_5$—COOH |
| OKL-1110 | gamma | mono | —S—$(CH_2)_5$—COOH |
| OKL-1111 | gamma | per | —S—$(CH_2)_5$—COOH |
| OKL-1146 | gamma | per | —S—$(CH_2)_3$—OH |
| OKL-1171 | gamma | per | —S—$(CH_2)_4$—COOH |
| OKL-1172 | gamma | per | —S—$(CH_2)_6$—COOH |
| OKL-1174 | gamma | per | —S—$(CH_2)_4$—OH |
| OKL-1178 | beta | per | —S—$(CH_2)_4$—COOH |
| OKL-1179 | beta | per | —S—$(CH_2)_6$—COOH |
| OKL-1180 | beta | per | —S—$(CH_2)_7$—COOH |
| OKL-1181 | beta | per | —S—$(CH_2)_3$—OH |
| OKL-1186 | alpha | mono | —S—$(CH_2)_5$—COOH |
| OKL-1187 | alpha | per | —S—$(CH_2)_5$—COOH |
| OKL-1188 | beta | mono | —S—$(CH_2)_6$—COOH |
| OKL-1189 | beta | mono | —S—$(CH_2)_4$—OH |
| OKL-1190 | gamma | mono | —S—$(CH_2)_6$—COOH |
| OKL-1191 | gamma | mono | —S—$(CH_2)_4$—OH |

TABLE 2

Comparative cyclodextrins.

| compound | cyclodextrin type | substitution pattern | substituent |
|---|---|---|---|
| OKL-1100 | beta | mono | —S—$(CH_2)_2$—COOH |
| OKL-1101 | beta | per | —S—$(CH_2)_2$—COOH |
| OKL-1102 | gamma | mono | —S—$(CH_2)_2$—COOH |
| OKL-1103 | gamma | per | —S—$(CH_2)_2$—COOH |
| OKL-1147 | gamma | per | —$NH_2$ |
| OKL-1170 | gamma | per | —S—$(CH_2)_2$—COOH |

Coagulation Assays

The Calibrated Automated Thrombogram® assays the generation of thrombin in clotting plasma using a microtiter plate reading fluorometer (Fluoroskan Ascent, ThermoLab systems, Helsinki, Finland) and Thrombinoscope® software (Thrombinoscope BV, Maastricht, The Netherlands). The assay was carried out as described by Hemker et al. (Pathofysiol. IIaemost. Thromb. 2003, 33, 4-15), and the Thrombinoscope® manual. Coagulation was triggered by recalcification in the presence of 1 or 5 pM recombinant human tissue factor (Innovin®, Siemens, Marburg, Germany), 4 μM phospholipids, and 417 μM fluorogenic substrate Z-Gly-Gly-Arg-AMC (Bachem, Bubendorf, Switzerland). Fluorescence was monitored using the Fluoroskan Ascent fluorometer (ThermoLabsystems, Helsinki, Finland), and the lag time, peak thrombin, velocity index and area under the curve (ETP) were calculated using the Thrombinoscope® software (Thrombinoscope BV).

In Vivo Bleeding Model

All animal protocols were approved by the Institutional Animal Care and Use Committee of the University of North Carolina. C57BL6/J mice were purchased from Charles Rivers Laboratories (Willmington, Mass.). Bleeding studies were done essentially as previously described Pastoft et al. (Haemophilia 2012; 18:782-8). Mice were anesthetized with isoflurane throughout all procedures. The hair on the ventral side of both hind limbs was removed. The animals were placed supine on a temperature and ECG monitoring board. The paws were gently restrained by looping soft polyethylene tubing around them and attaching the tubing to the ECG board. The skin on the left and right ventral hind limb was incised which exposes a length of the saphenous neurovascular bundle; the bundle was covered with normal saline to prevent drying. To assess haemostasis, the right saphenous vein was transected by piercing it with a 23-G needle followed by a longitudinal incision made in the distal portion of the vessel. Blood was gently wicked away until haemostasis occurred. The clot was then removed to restart bleeding and the blood was again wicked away until haemostasis occurs again. Clot disruption was repeated after every incidence of haemostasis for 30 minutes. Mice were fed chow that contained 0.1 mg rivaroxaban per g of chow. The mice were on this diet for 4 days to allow them to reach a steady state. Cyclodextrins were administered by a tail vein injection 5 minutes before the start of the bleeding assay. Two parameters were measured: 1) the number of times that haemostasis occurs in a 30 minute period, and 2) the time required for each haemostasis.

Results

Coagulation Assays in Normal Plasma

Thrombin generation analyses were performed in pooled normal plasma with and without the addition of anticoagulants. The results are summarized in table 3.

TABLE 3

Overview of procoagulant activity of tested cyclodextrins.

| Modification | α-mono | α-per | β-mono | β-per | γ-mono | γ-per |
|---|---|---|---|---|---|---|
| S—C2—COOH | | | 1100 No effect | 1101 No effect | 1102 No effect | 1103/1170 No effect |
| S—C3—COOH | | | | 1105 ** | 1106 **** | 1107 *** |
| S—C4—COOH | | | | 1178 * | | 1171 * |
| S—C5—COOH | 1186 * | 1187 ***** | 1108 * | 1109 * | 1110 ** | 1111 **** |
| S—C6—COOH | | | 1188 **** | 1179 ** | 1190 * | 1172 *** |
| S—C7—COOH | | | | 1180 *** | | |
| S—C2—OH | | | | | | |
| S—C3—OH | | | | 1181 ** | | 1146 *** |
| S—C4—OH | | | 1189 **** | | 1191 **** | 1174 **** |

The number of * shows the strength of procoagulant activity.
The increasing number of * indicates stronger procoagulant activity.
— "No effect" indicates no effect in coagulation assay.
Boxes without number: not determined.

Figure 14:
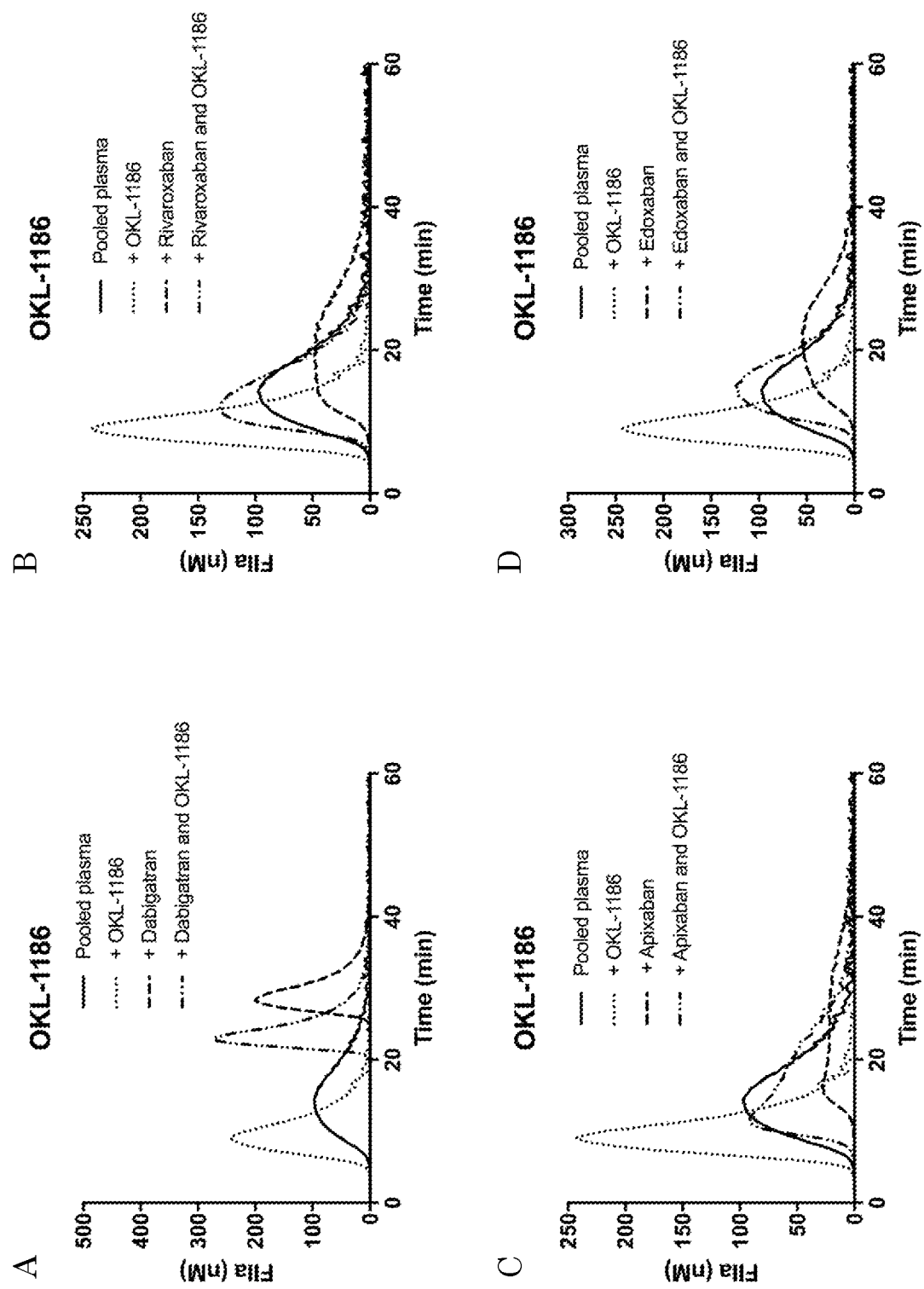

Alpha-Mono-Carboxyl Cyclodextrins:

OKL-1186 had a substantial procoagulant effect in normal plasma and antagonized the anticoagulant effect of dabigatran, rivaroxaban, apixaban and edoxaban (table 4 and FIG. 14).

Figure 15:
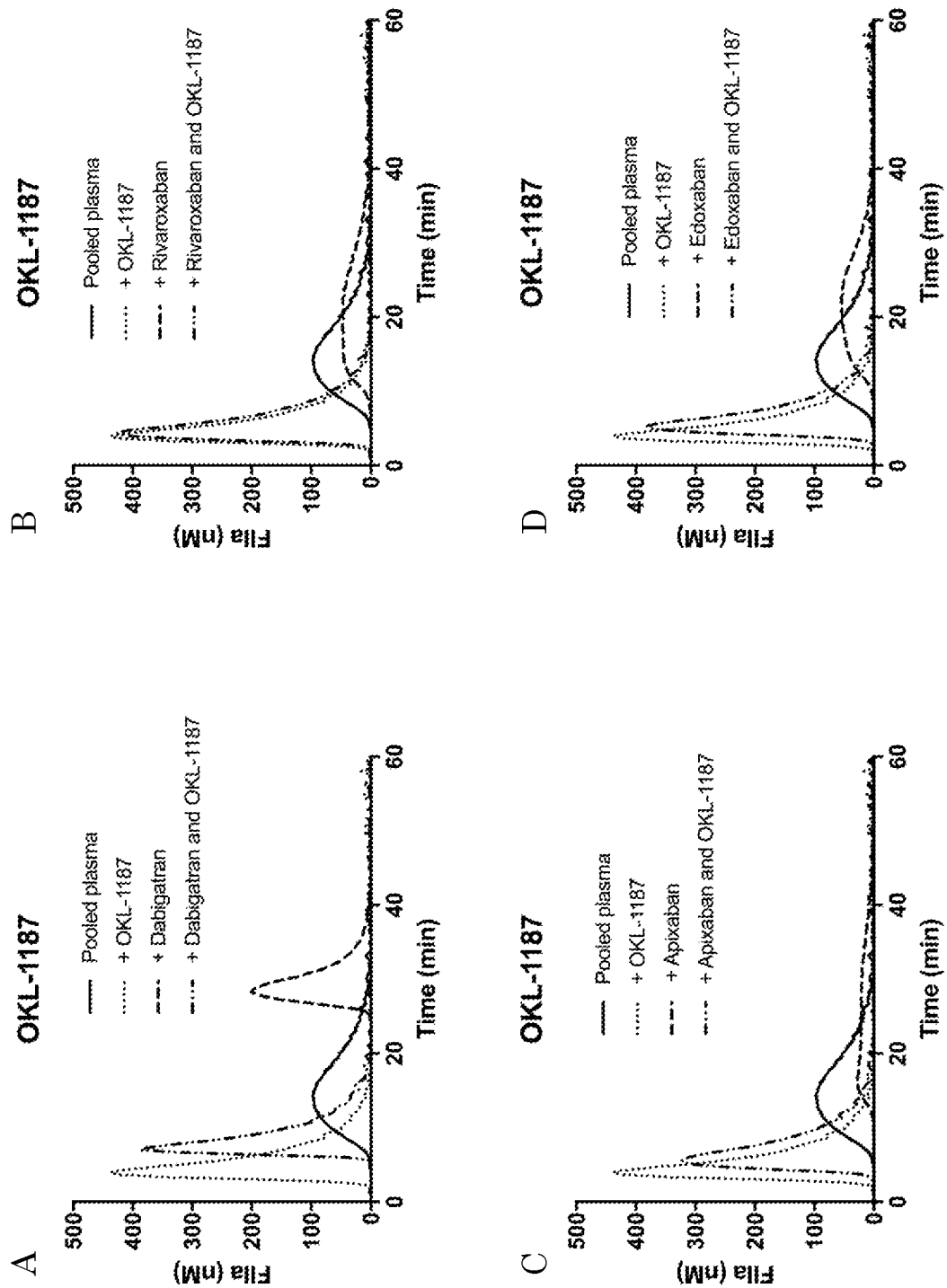

Alpha-Per-Carboxyl Cyclodextrins:

OKL-1187 showed a very strong procoagulant effect in normal plasma and strongly antagonized the anticoagulant effect of dabigatran, rivaroxaban, apixaban and edoxaban (table 4 and FIG. 15).

Figure 3:
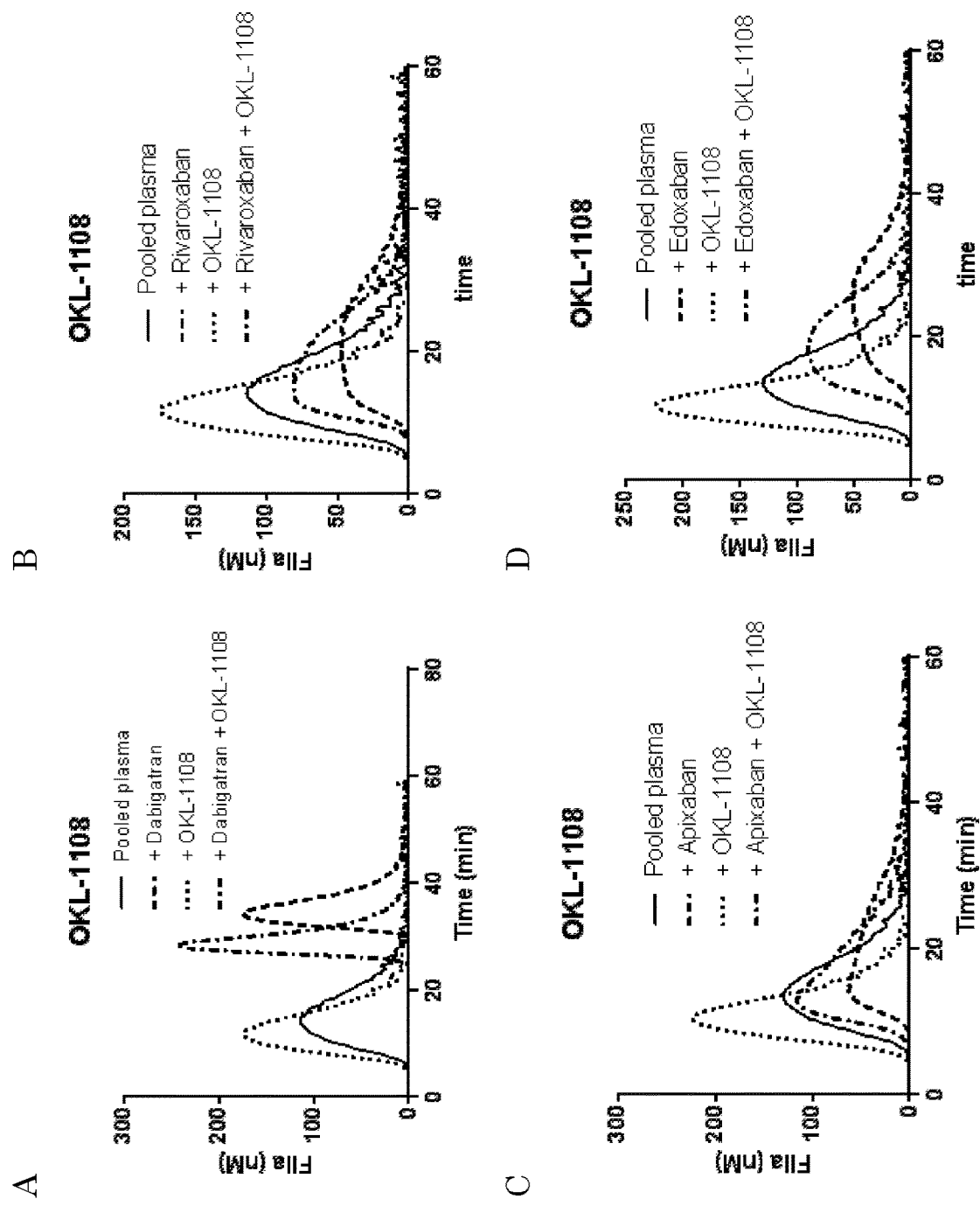
FIGS. 3-8, 12, 14-19 and 22-27: Pooled normal plasma was spiked with cyclodextrins (100 µM, unless otherwise indicated) and anticoagulants. The concentrations of the anticoagulants were 100 ng/ml for dabigatran (A), 100 ng/ml for rivaroxaban (B), 60 ng/ml for apixaban (C), 60 ng/ml for edoxaban (D). The plasmas were subjected to thrombin generation analysis as described in the Materials and Methods section with 1 pM tissue factor (TF) as initiator of coagulation.
Figure 16:
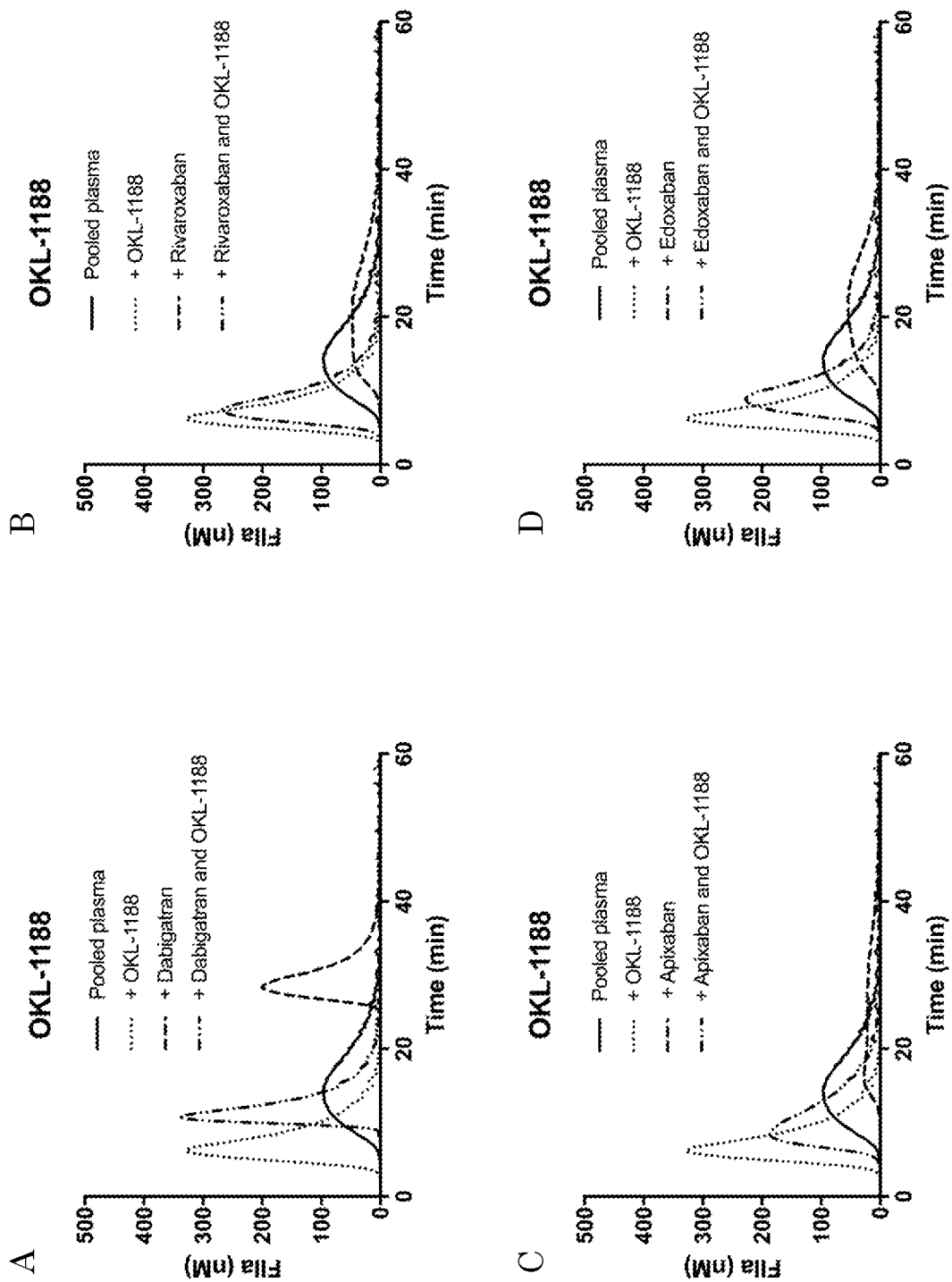

Beta-Mono-Carboxyl Cyclodextrins:

OKL-1108 had a substantial procoagulant effect in plasma and antagonized the anticoagulant effect of dabigatran, rivaroxaban, apixaban and edoxaban (table 4 and FIG. 3), OKL-1188 showed a strong procoagulant effect in normal plasma and antagonized the anticoagulant effect of dabigatran, rivaroxaban, apixaban and edoxaban (table 4 and FIG. 16).

Figure 4:
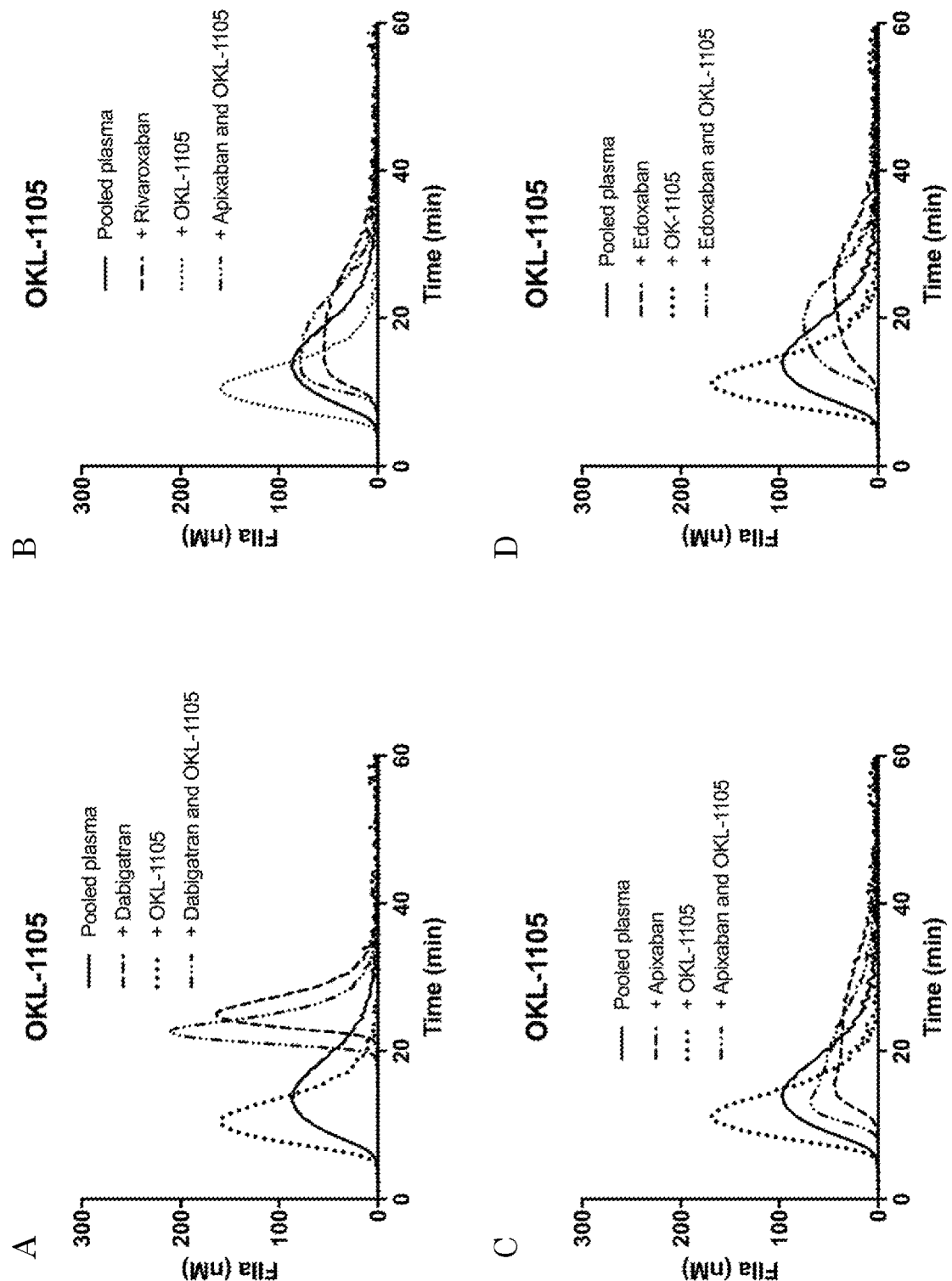
Figure 5:
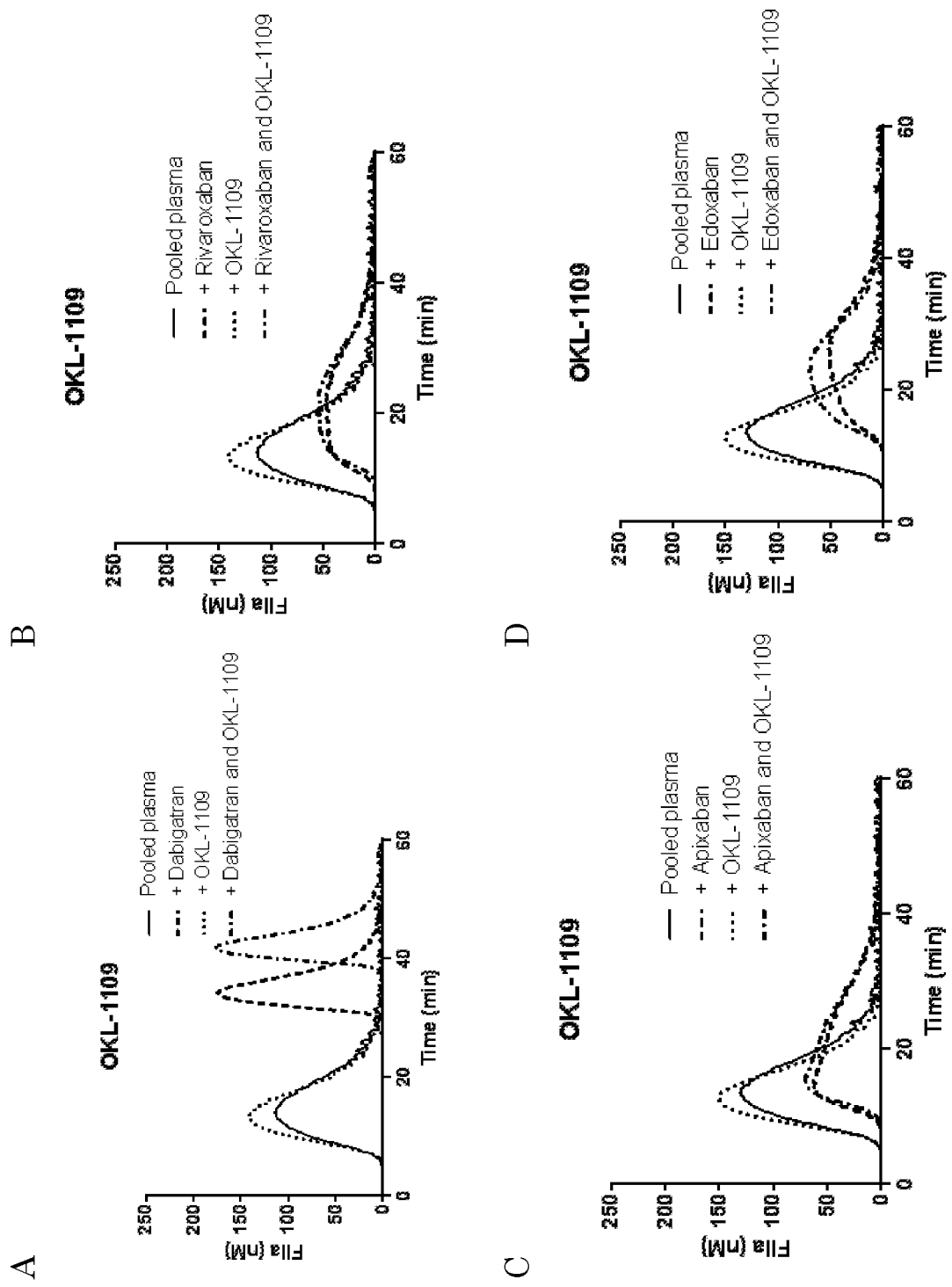
Figure 25:
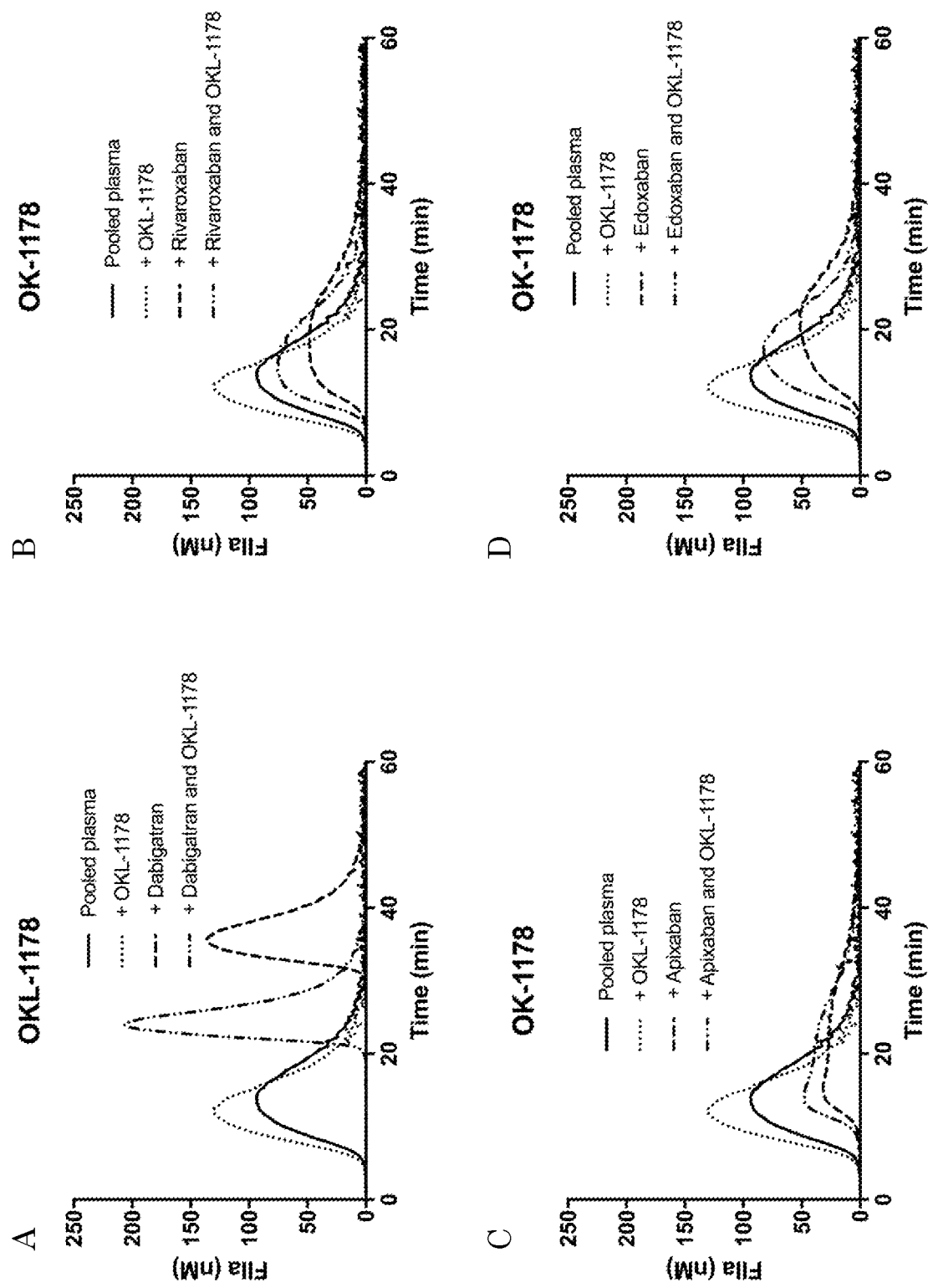
Figure 26:
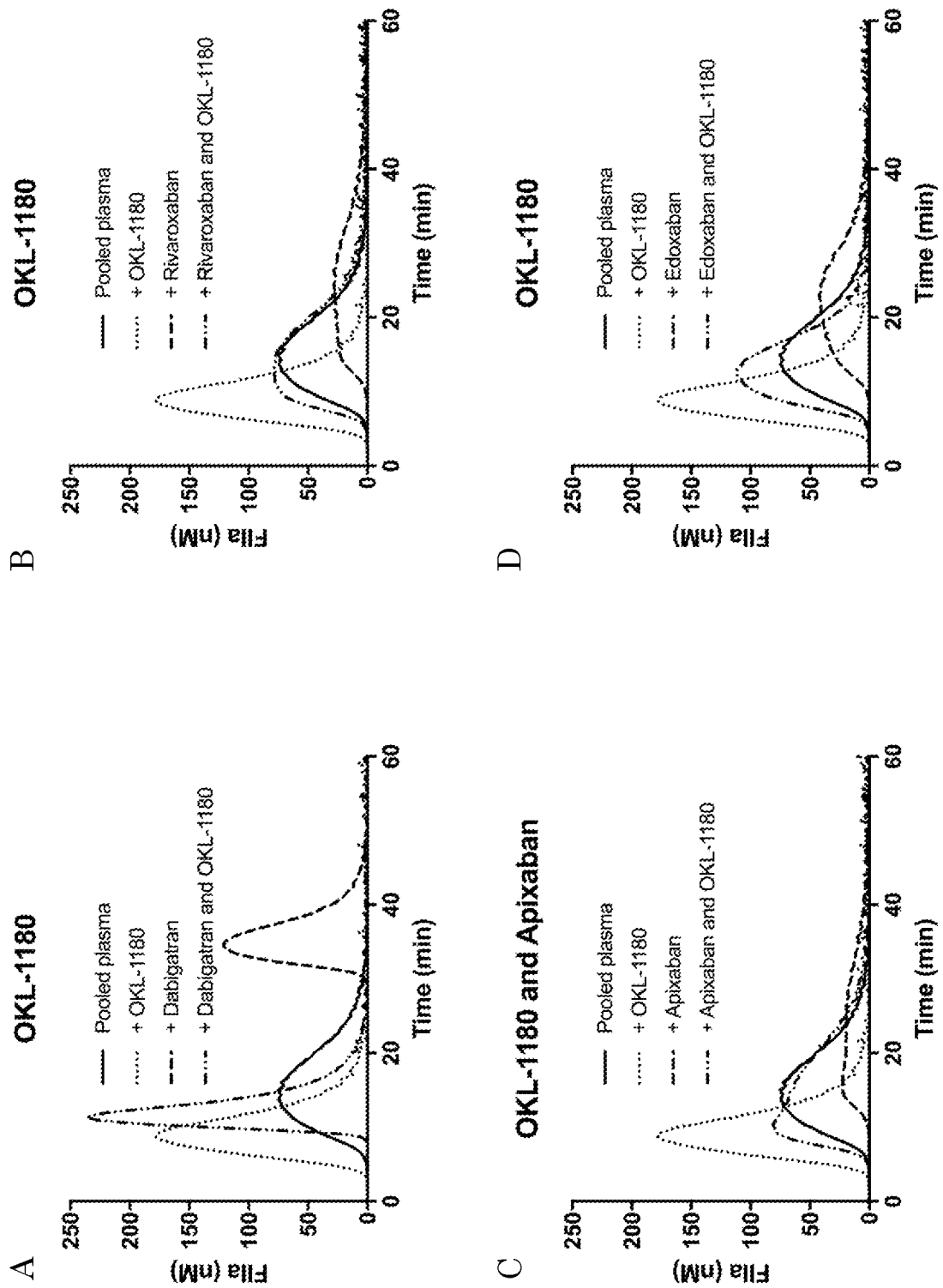

Beta-Per-Carboxyl Cyclodextrins:

Addition of OKL-1105 gave a significant procoagulant effect in plasma. In the presence of dabigatran, rivaroxaban, apixaban and edoxaban also procoagulant effects were observed. As such the anticoagulant effect of the NOACs was antagonized (table 4 and FIG. 4), OKL-1109 had small effects on thrombin generation in plasma. In the presence of dabigatran, rivaroxaban, apixaban and edoxaban there were marginal or no effects on thrombin generation (table 4 and FIG. 5), OKL-1178, OKL-1179 and OKL-1180 showed procoagulant activity in normal plasma at varying degrees (table 4 and FIGS. 25-26).

Gamma-Mono-Carboxylic Cyclodextrins

Figure 6:
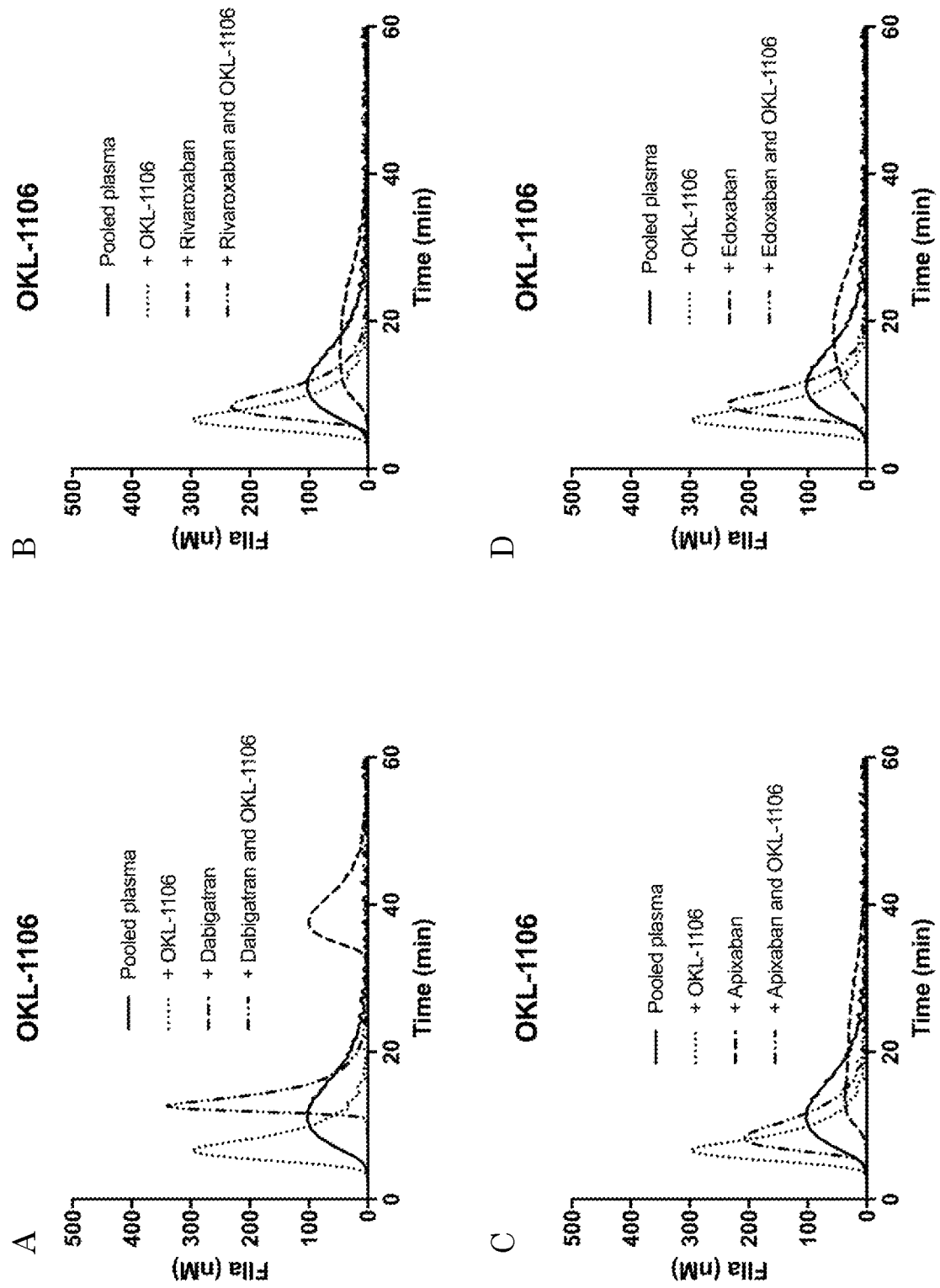
Figure 7:
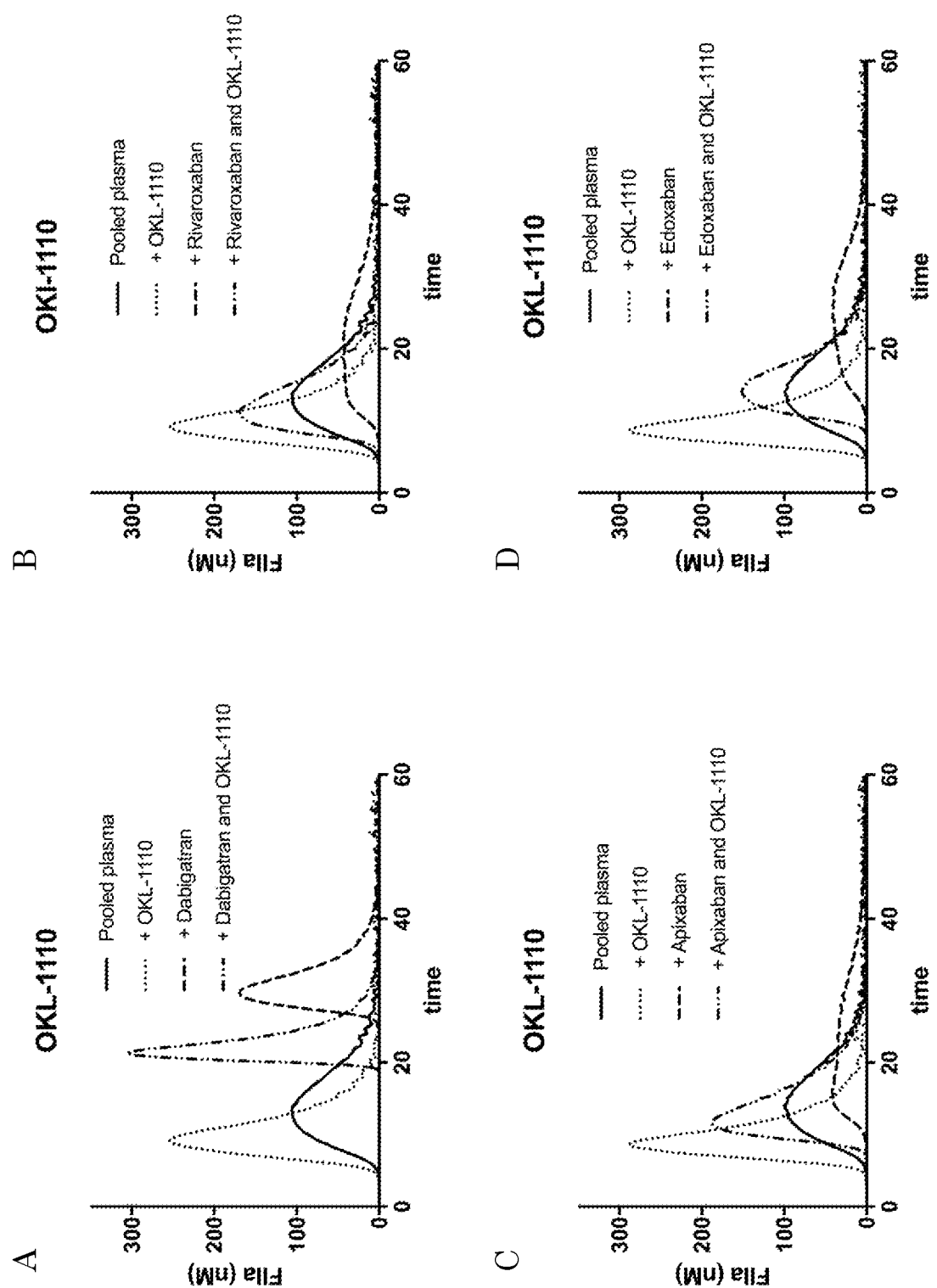
Figure 18:
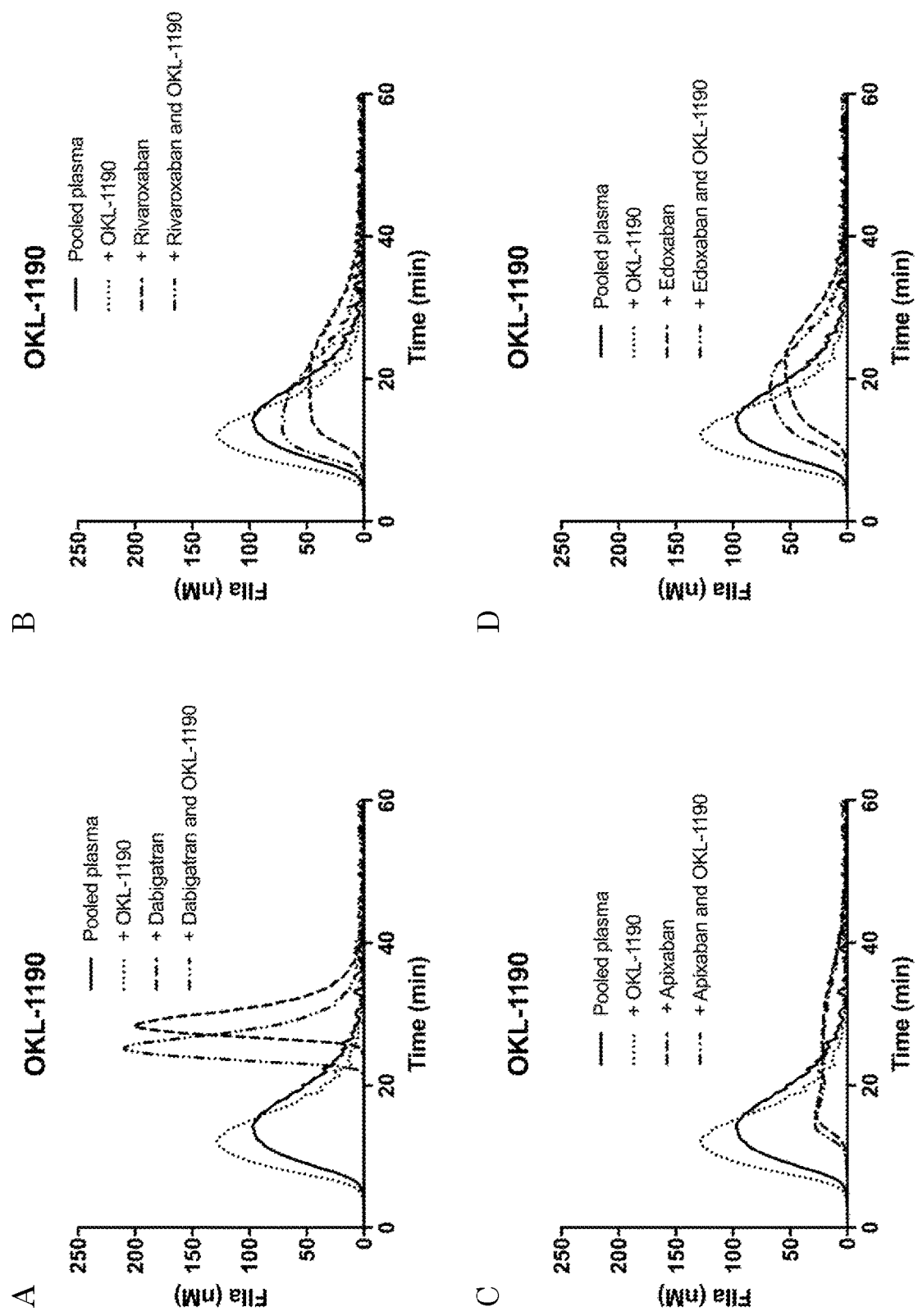

OKL-1106 induced a procoagulant effect in normal plasma and significantly antagonized the anticoagulant actions of dabigatran and rivaroxaban. Its effect on the anticoagulant actions of apixaban and edoxaban were less pronounced (table 4 and FIG. 6), OKL-1110 induced a very potent procoagulant effect in normal plasma and fully counteracted the anticoagulant effect of the Xa-antagonists rivaroxaban, edoxaban and apixaban. OK-1110 also strongly antagonized the anticoagulant effects of the direct thrombin inhibitor dabigatran (table 4 and FIG. 7), OKL-1190 had a procoagulant effect in normal plasma and also antagonized the anticoagulant effect of dabigatran, rivaroxaban, apixaban and edoxaban (table 4 and FIG. 18).

Gamma-Per-Carboxylic Cyclodextrins

Figure 8:
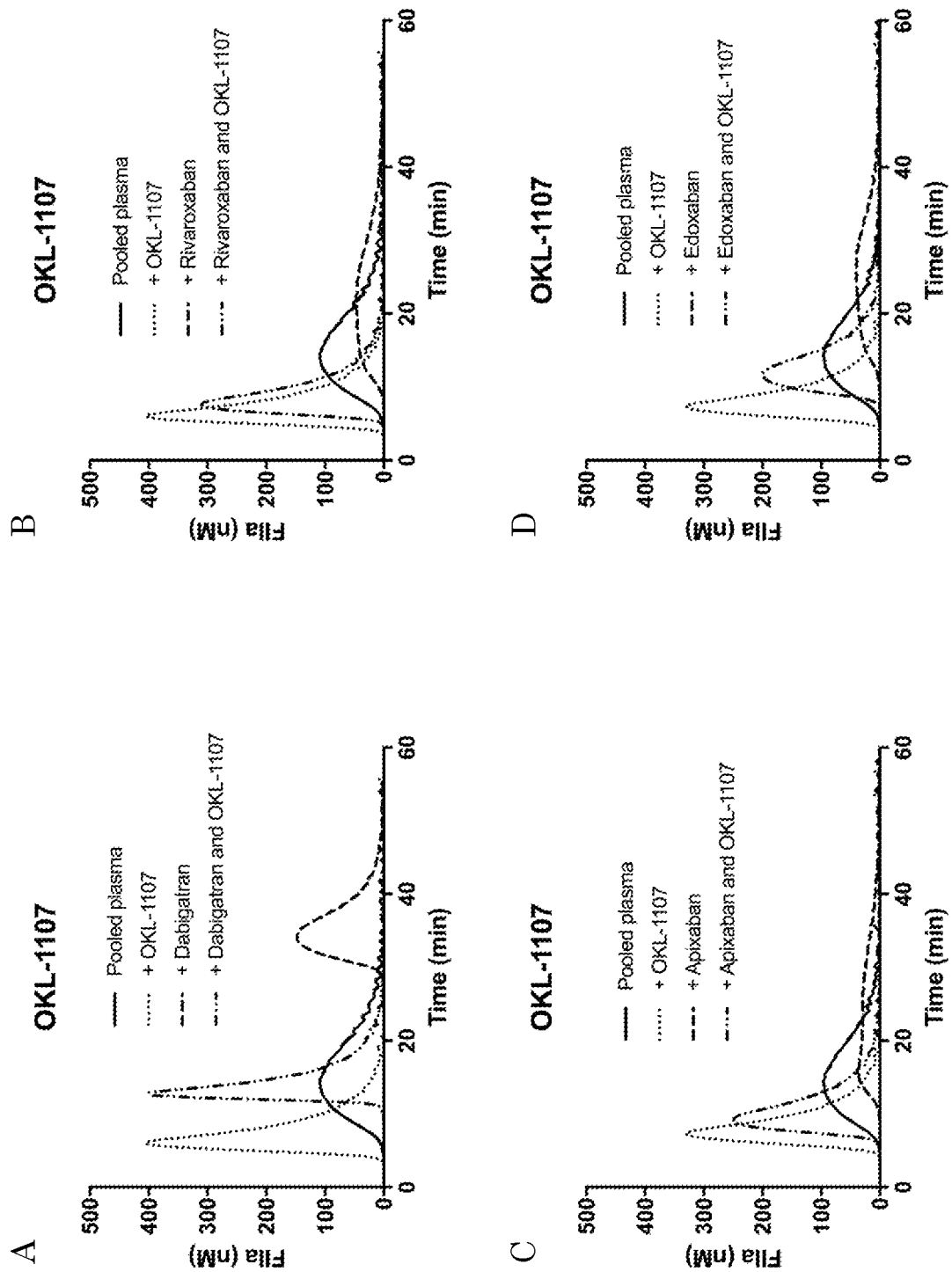
Figure 22:
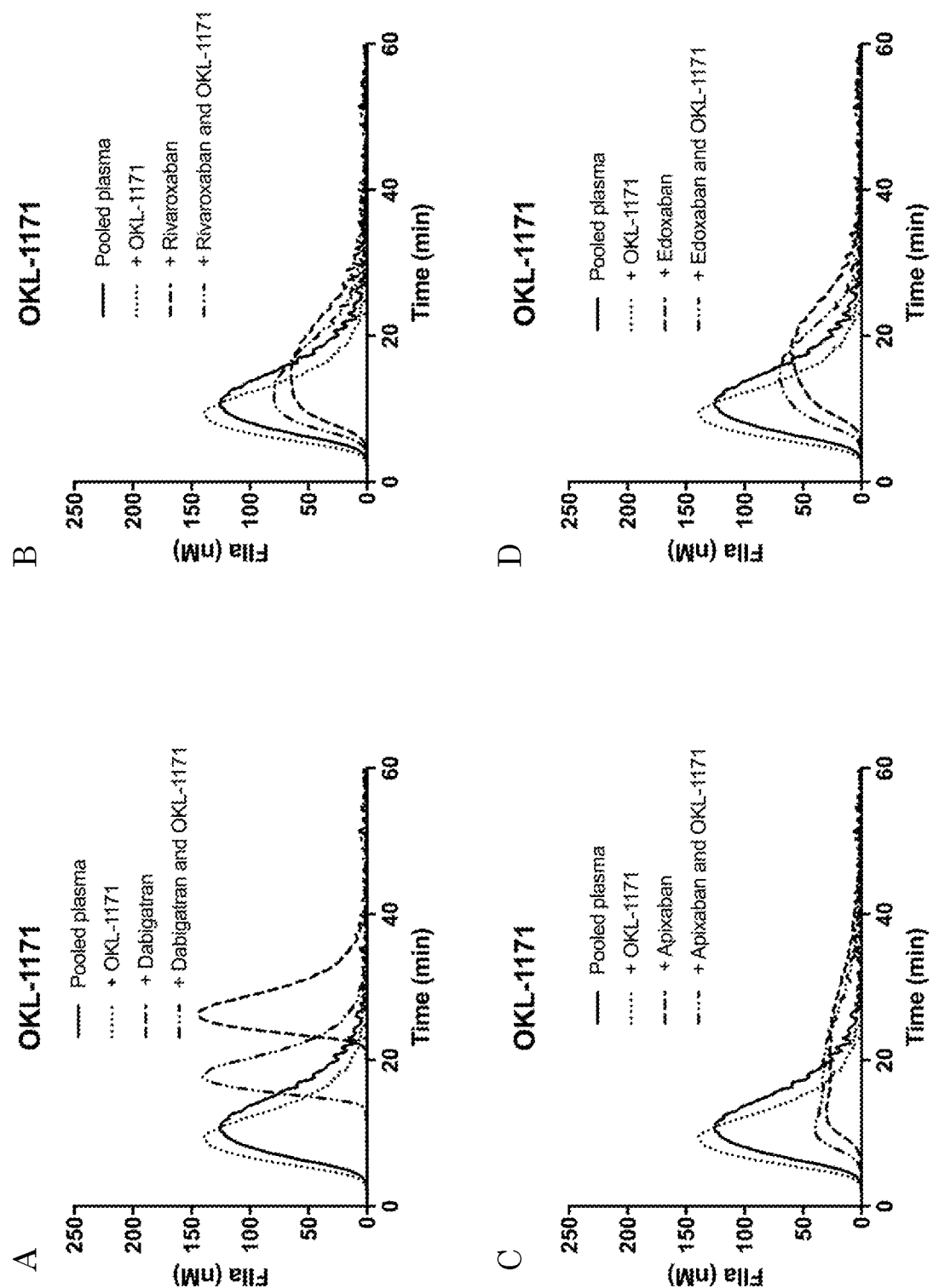
Figure 23:
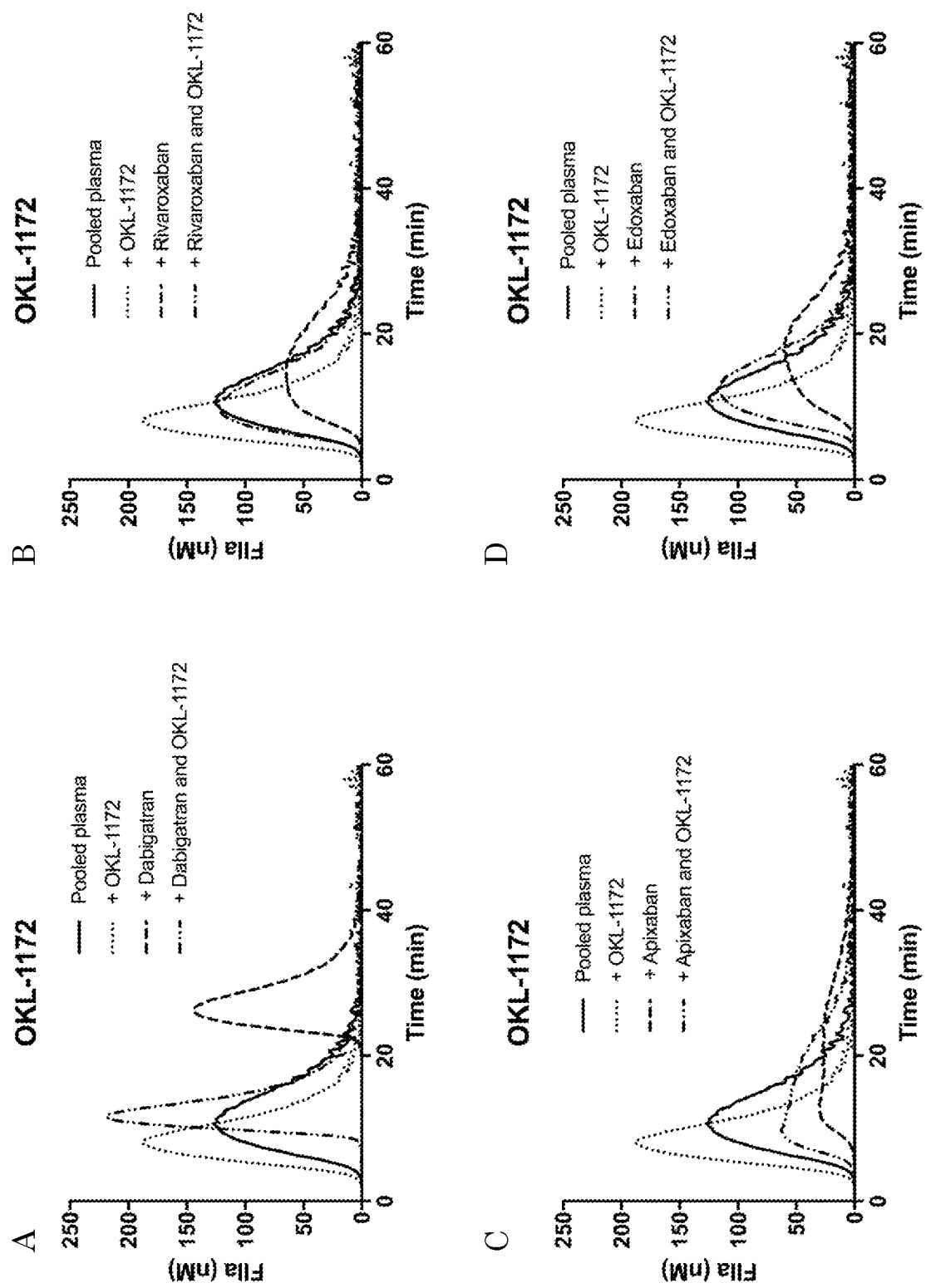

Addition of OKL-1107 gave strong procoagulant effects in plasma. Peak thrombin was largely increased and the lag time was considerably shorter. After addition of dabigatran, rivaroxaban, apixaban or edoxaban the effects of OKL-1107 remained, and thrombin generation was completely restored or even higher than in the non-anticoagulated plasma (table 4 and FIG. 8), OKL-1171 and OKL-1172 showed significant procoagulant activity in plasma (table 4 and FIGS. 22-23).

Figure 9:
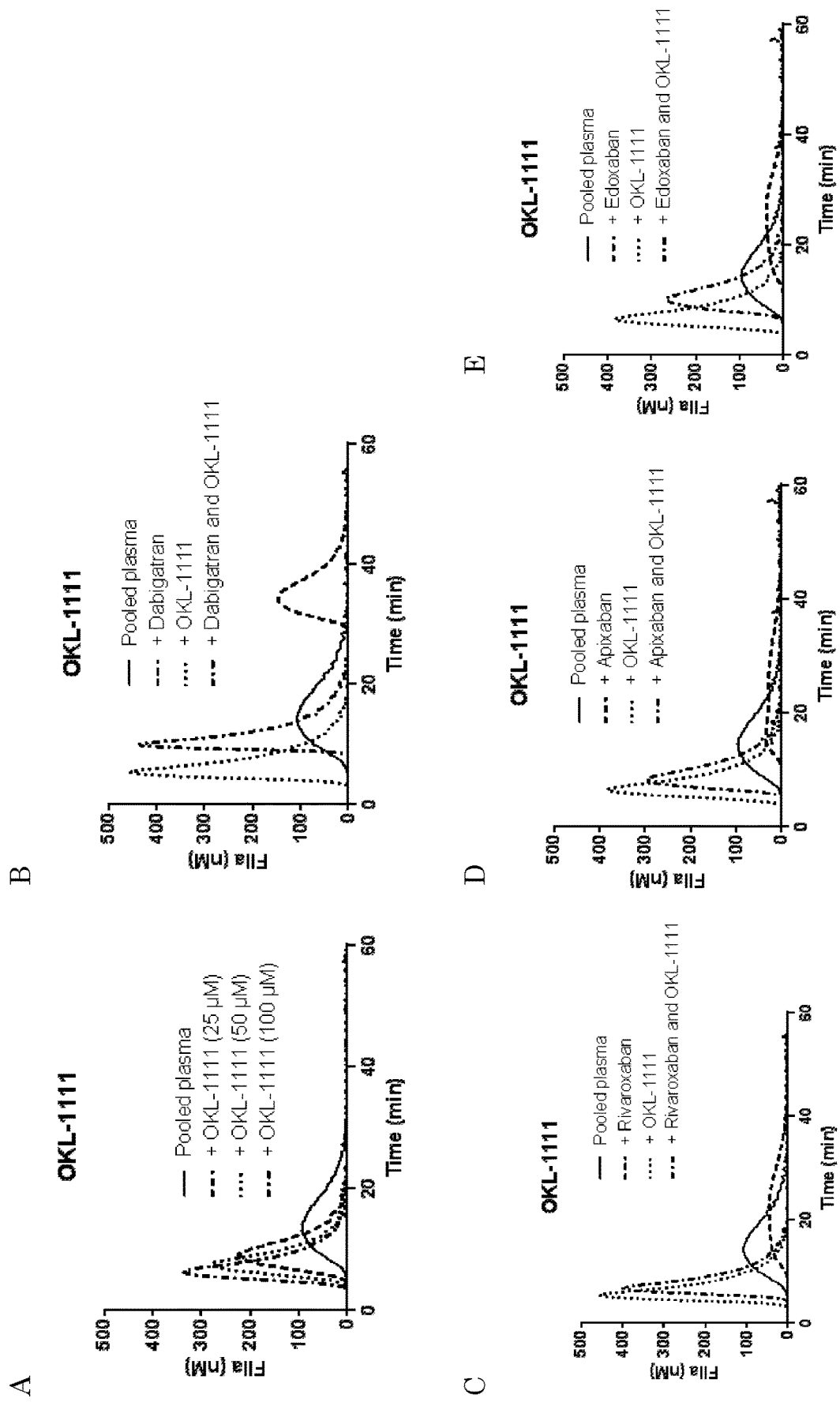
FIG. 9: Pooled normal plasma was spiked with OKL-1111 (100 µM, unless otherwise indicated (A)) and anticoagulants (B-E). The concentrations of the anticoagulants were 100 ng/ml for dabigatran (B), 100 ng/ml for rivaroxaban (C), 60 ng/ml for apixaban (D), 60 ng/ml for edoxaban (E). The plasmas were subjected to thrombin generation analysis as described in the Materials and Methods section with 1 pM tissue factor (TF) as initiator of coagulation.
Figure 10:
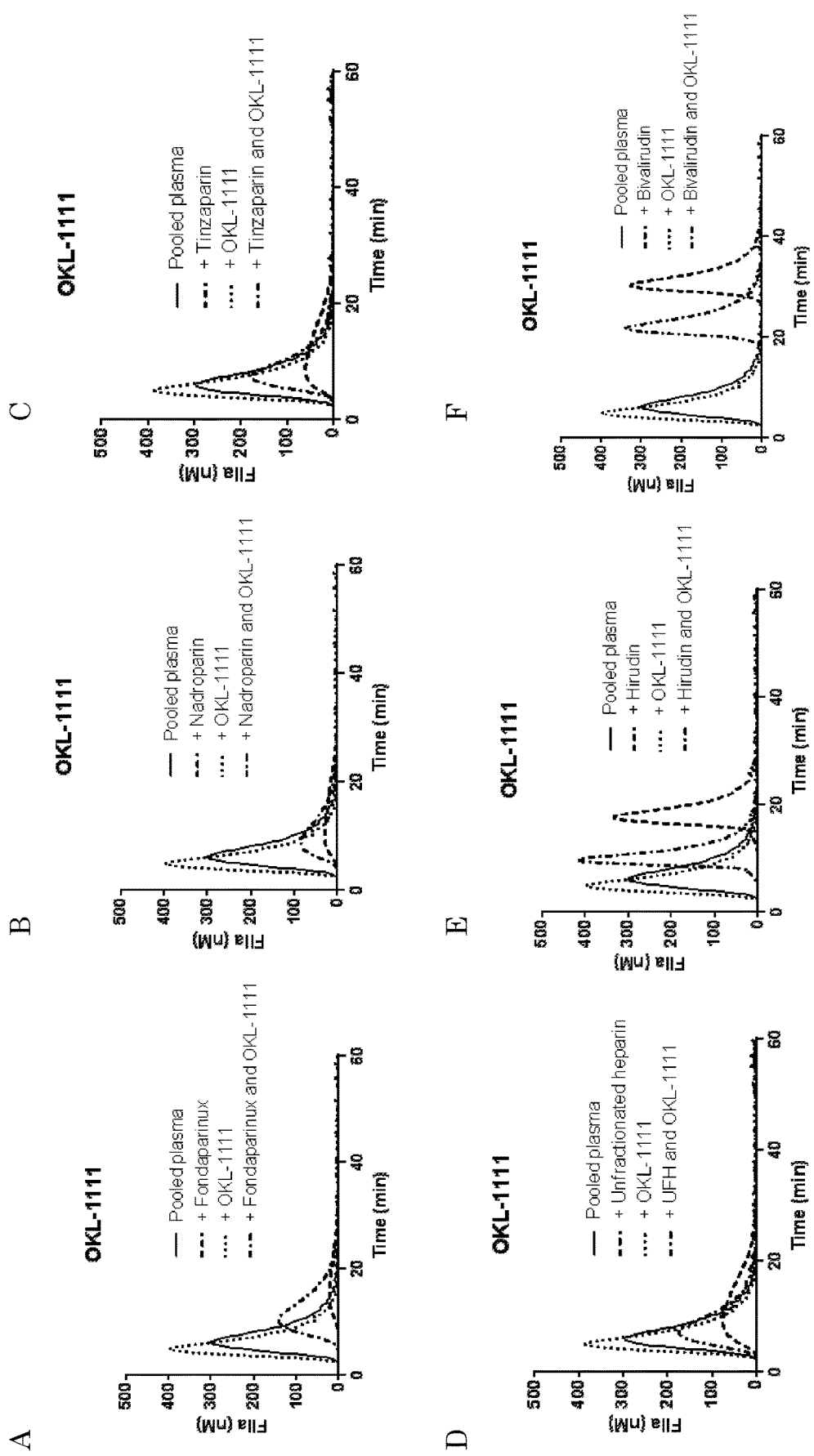
FIG. 10: Pooled normal plasma was spiked with OKL-1111 (100 µM) and anticoagulants (A-F). The concentrations of the anticoagulants were 2 µg/ml for fondaparinux (A), 0.4 U/ml for nadroparin (B), 0.1 U/ml for tinzaparin (C), 0.03 U/ml for unfractionated heparin (UFH) (D), 0.5 U/ml for hirudin (E) and 10 µg/ml for bivalirudin (F). The plasmas were subjected to thrombin generation analysis as described in the Materials and Methods section with 1 pM tissue factor (TF) as initiator of coagulation.
Figure 11:
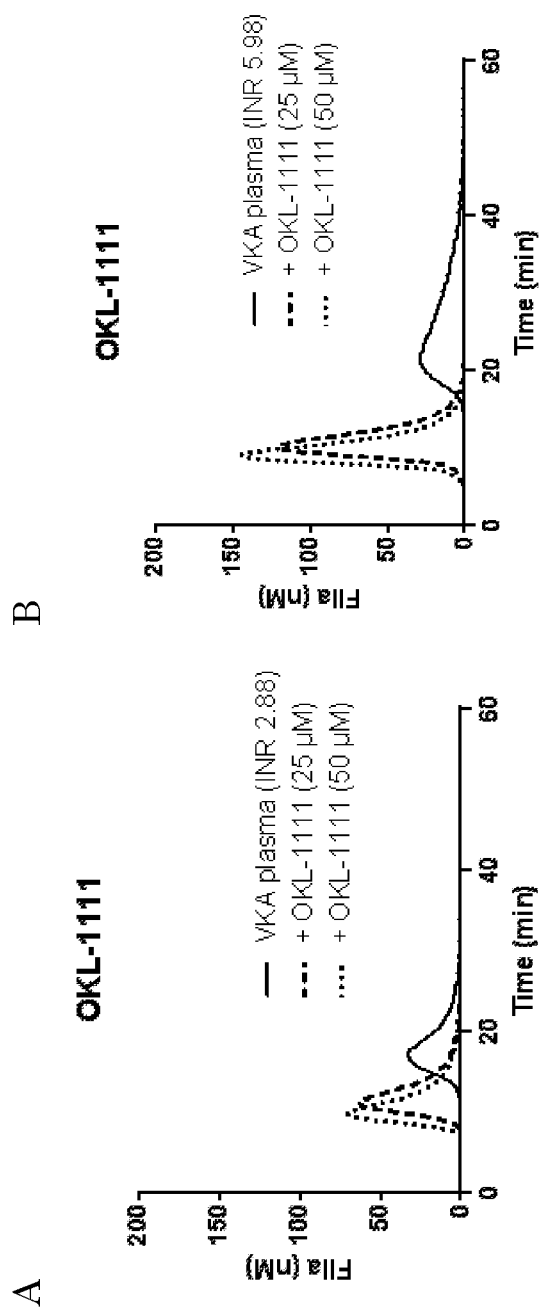
FIG. 11: Plasma was used from individuals taking vitamin K-antagonists (VKA plasma). Two different intensities of treatment (given as INR) were available, as depicted in (A) and (B). The plasmas were subjected to thrombin generation analysis as described in the Materials and Methods section with 1 pM tissue factor (TF) as initiator of coagulation.

Addition of OKL-1111 gave very strong procoagulant effects in plasma (table 4 and FIG. 9). Peak thrombin was largely increased and the lag time was considerably shorter than in the absence of CD. After addition of dabigatran, rivaroxaban, apixaban or edoxaban the effects of OKL-1111 were still highly procoagulant with restoration of thrombin generation to levels far above that of non-anticoagulated plasma (FIG. 10), OKL-1111 was also capable of restoring thrombin generation in plasma anticoagulated with unfractionated and low molecular weight heparin, pentasaccharide (arixtra), hirudin and bivalirudin (FIG. 10). Also, in plasma of patients using vitamin K antagonists, thrombin generation could be improved by the addition of OKL-1111 (FIG. 11).

Beta-Mono-Hydroxylic Cyclodextrins

Figure 17:
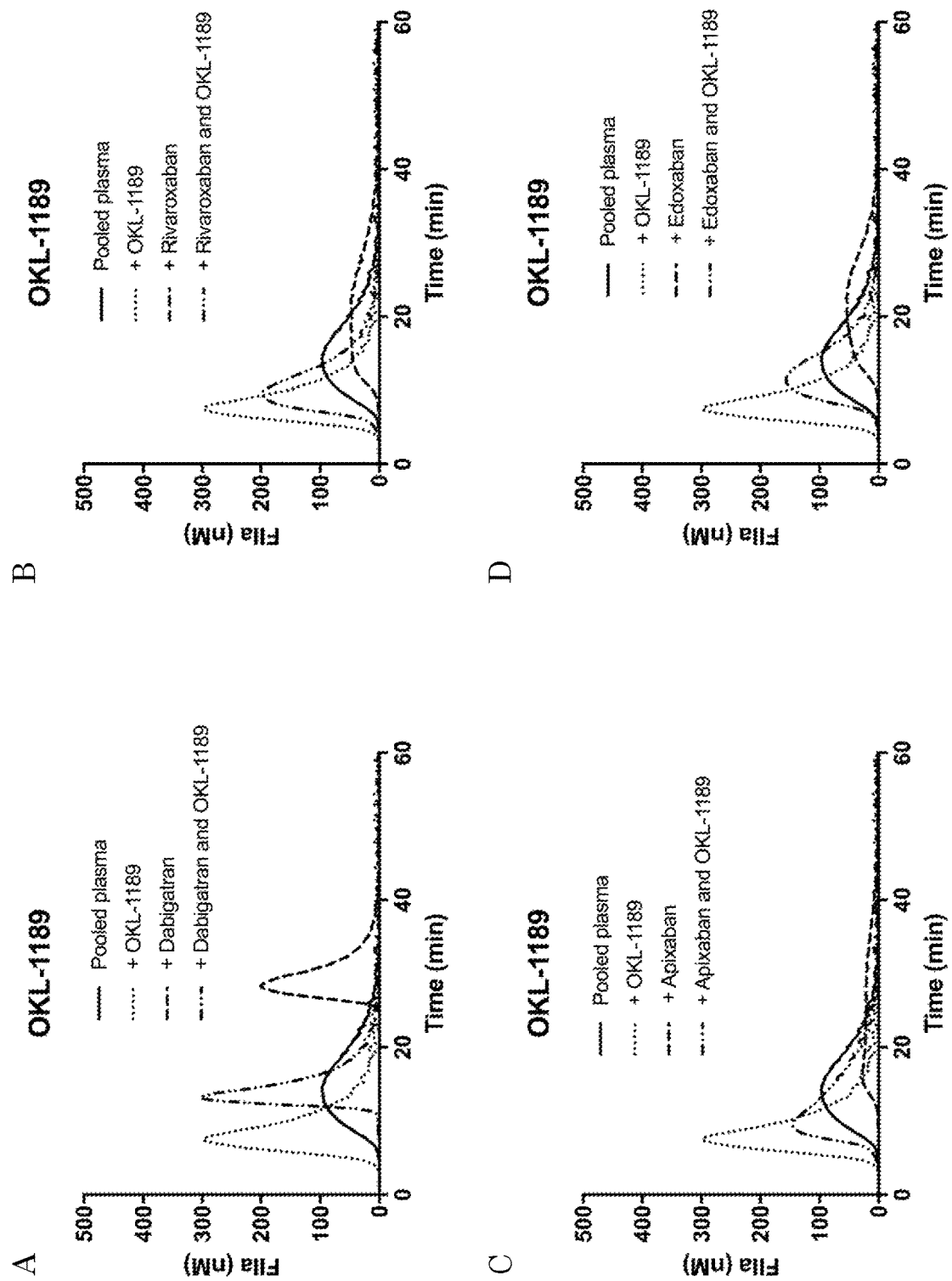

OKL-1189 showed strong procoagulant activity in normal plasma and strongly antagonized the anticoagulant effect of dabigatran, rivaroxaban, apixaban and edoxaban (table 4 and FIG. 17).

Beta-Per-Hydroxylic Cyclodextrins

Figure 27:
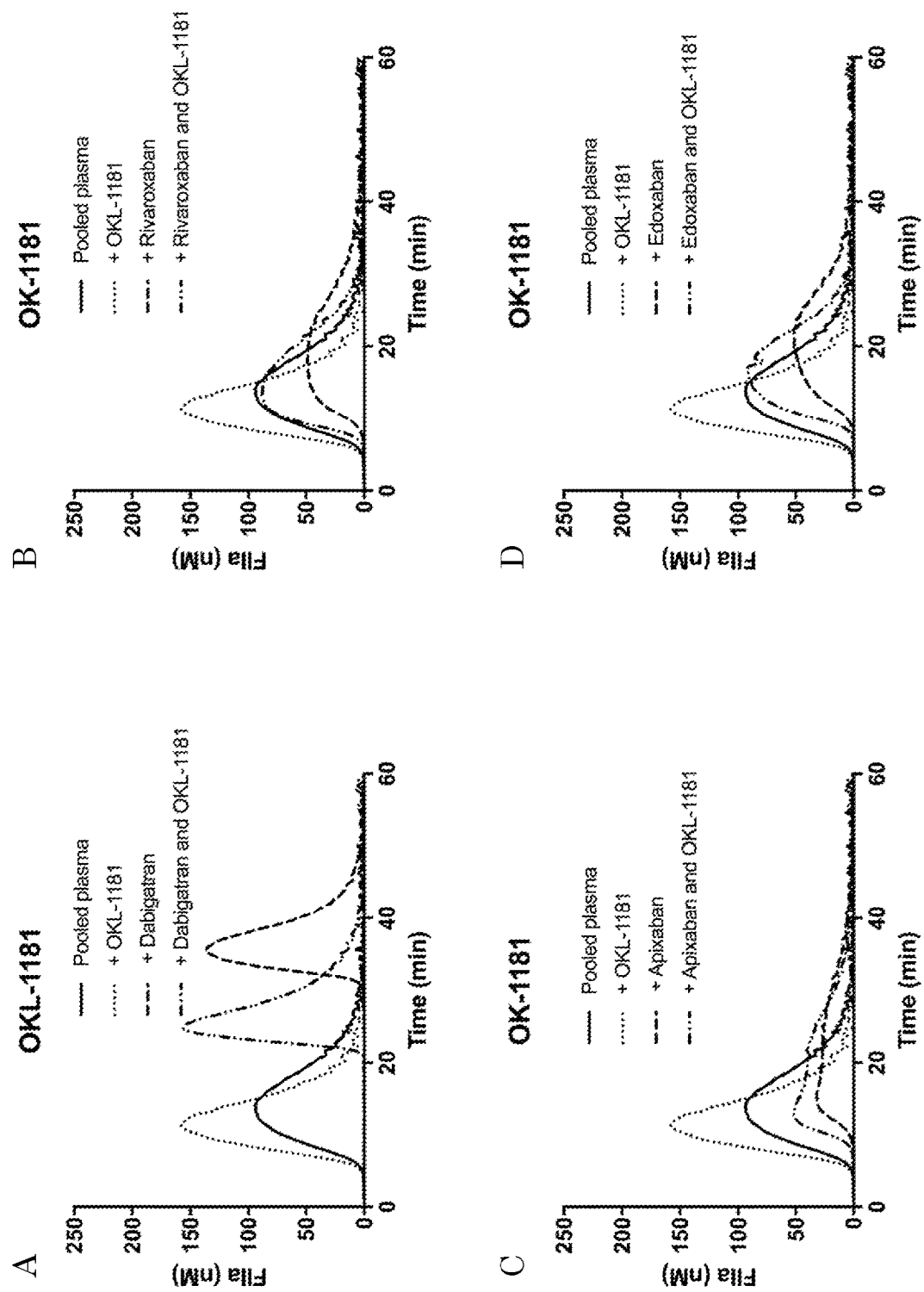

OK-1181 showed significant procoagulant activity in plasma (table 4 and FIG. 27).

Gamma-Mono-Hydroxylic Cyclodextrins

Figure 19:
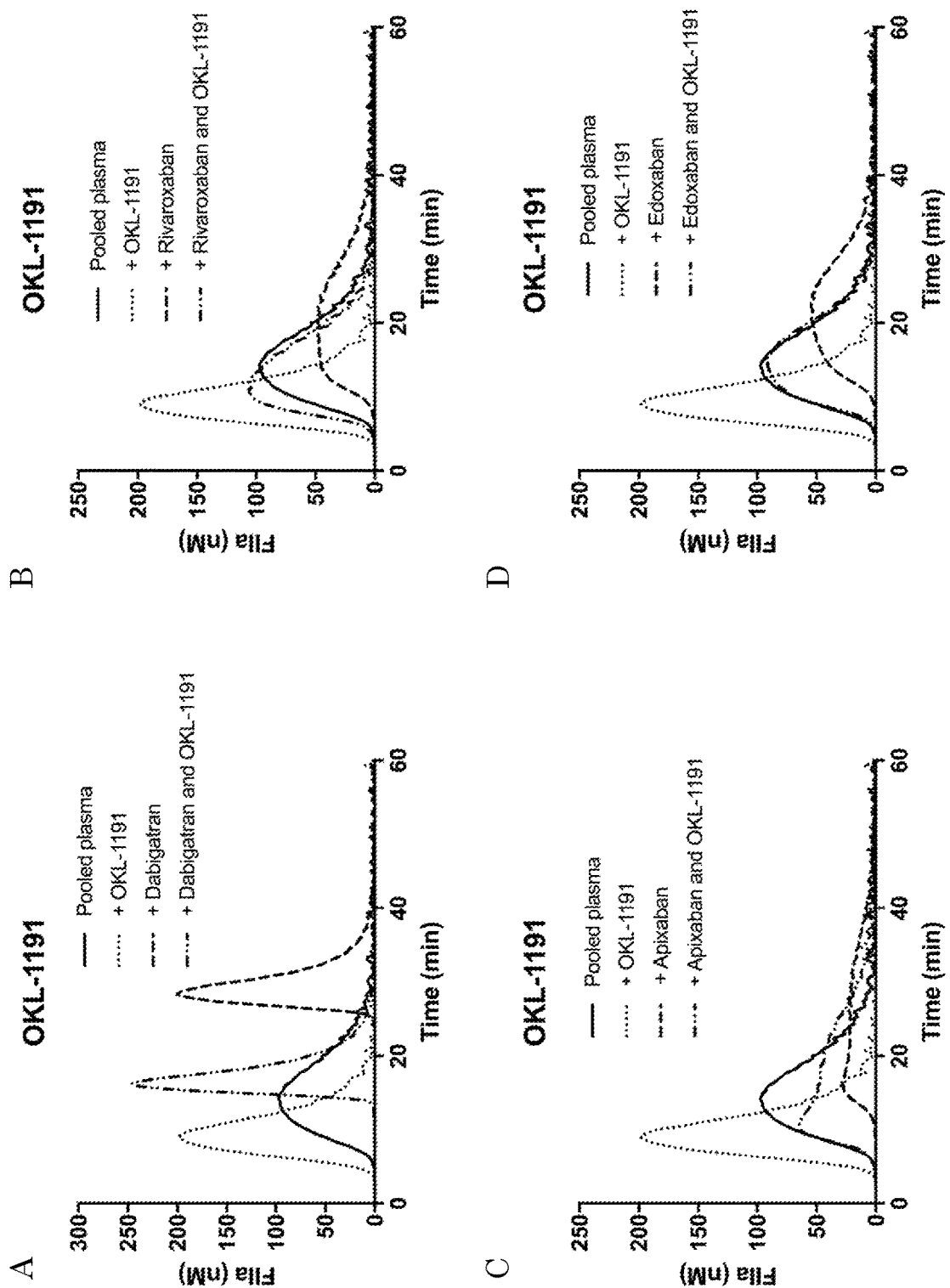

OKL-1191 Showed Strong Procoagulant Activity in Plasma and Also Antagonized the anticoagulant effect of dabigatran, rivaroxaban, apixaban and edoxaban (table 4 and FIG. 19).

Gamma-Per-Hydroxylic Cyclodextrins

Figure 12:
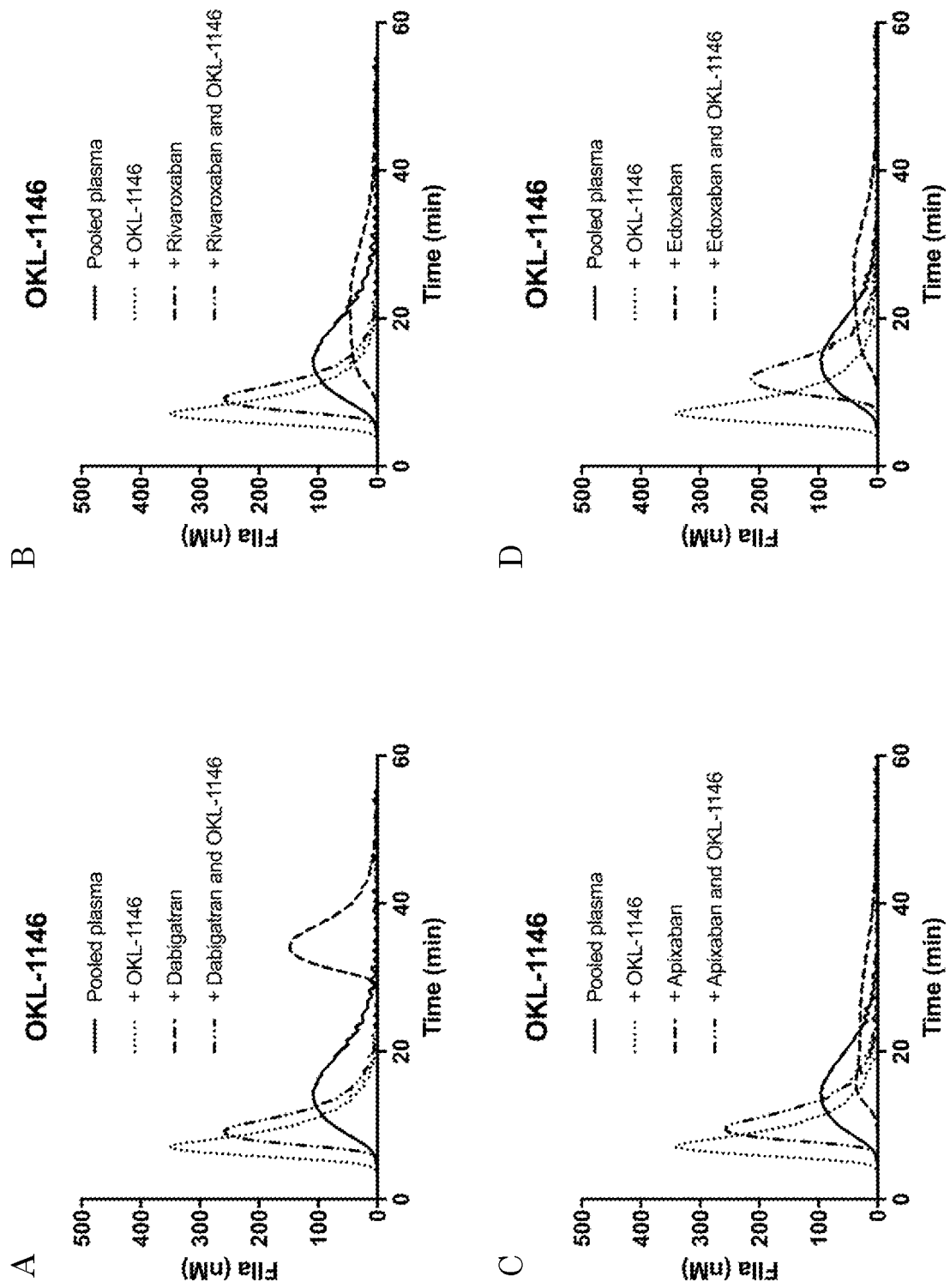
Figure 24:
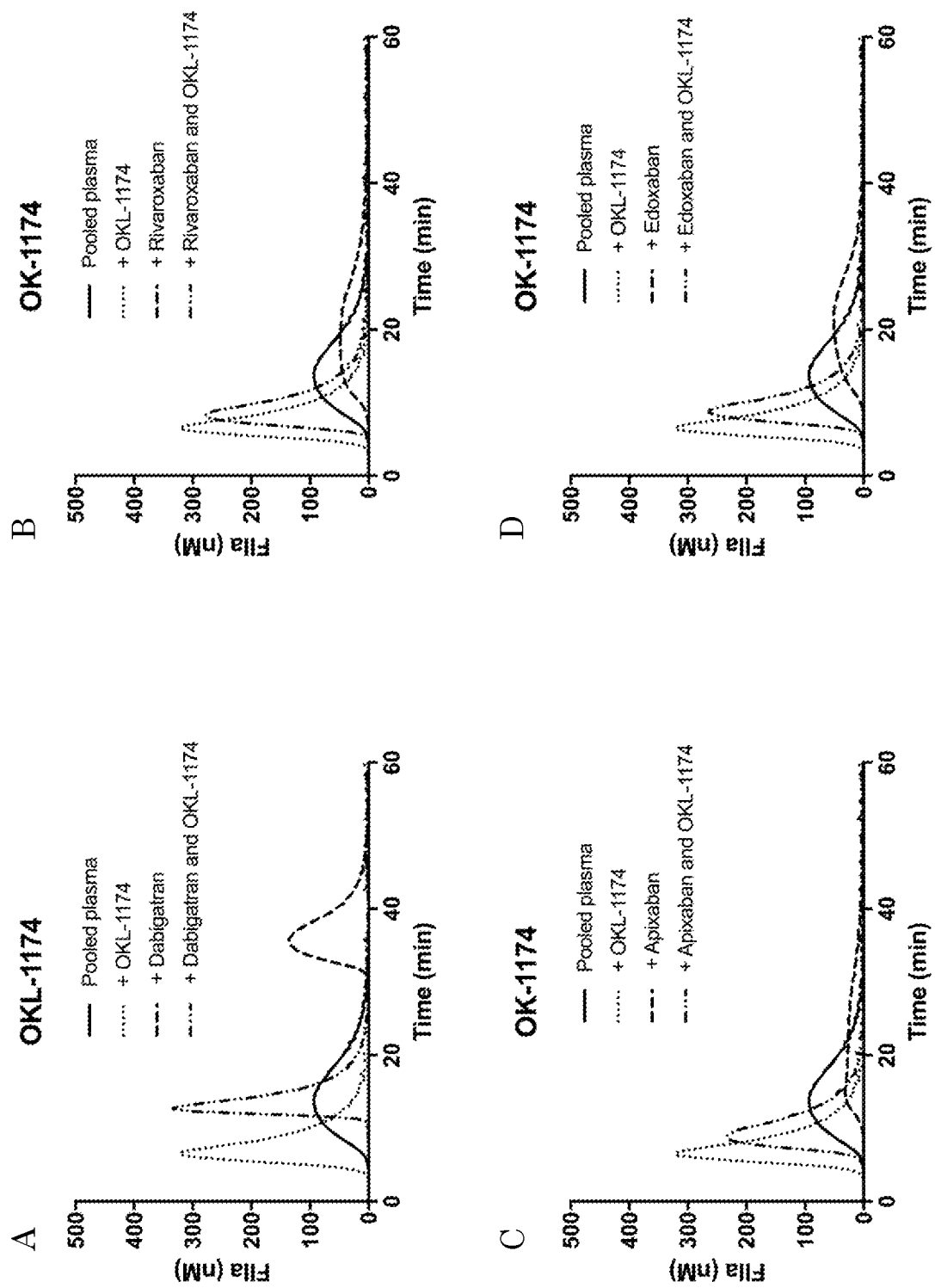

Addition of OKL-1146 gave very strong procoagulant effects in plasma (table 4 and FIG. 12). Peak thrombin was largely increased and the lag time was considerably shorter than in the absence of CD. After addition of dabigatran, rivaroxaban, apixaban or edoxaban the effects of OKL-1146 were still highly procoagulant with restoration of thrombin generation to levels far above that of non-anticoagulated plasma (FIG. 12). Similarly, OKL-1174 gave strong procoagulant effects in plasma, also in the presence of anticoagulants (FIG. 24).

Substituted Cyclodextrins Containing a C2 Substituent

Beta-mono-, beta-per-, gamma-mono- and gamma-per-hydroxylic substituted cyclodextrins OKL-1100, OKL-1101, OKL-1102 and OKL-1103/OKL-1170 did not show procoagulant activity in normal plasma, nor in plasma containing anticoagulants. These cyclodextrins were therefore not tested in deficient plasma.

Gamma-Per-Amine-Substituted Cyclodextrins

Figure 13:
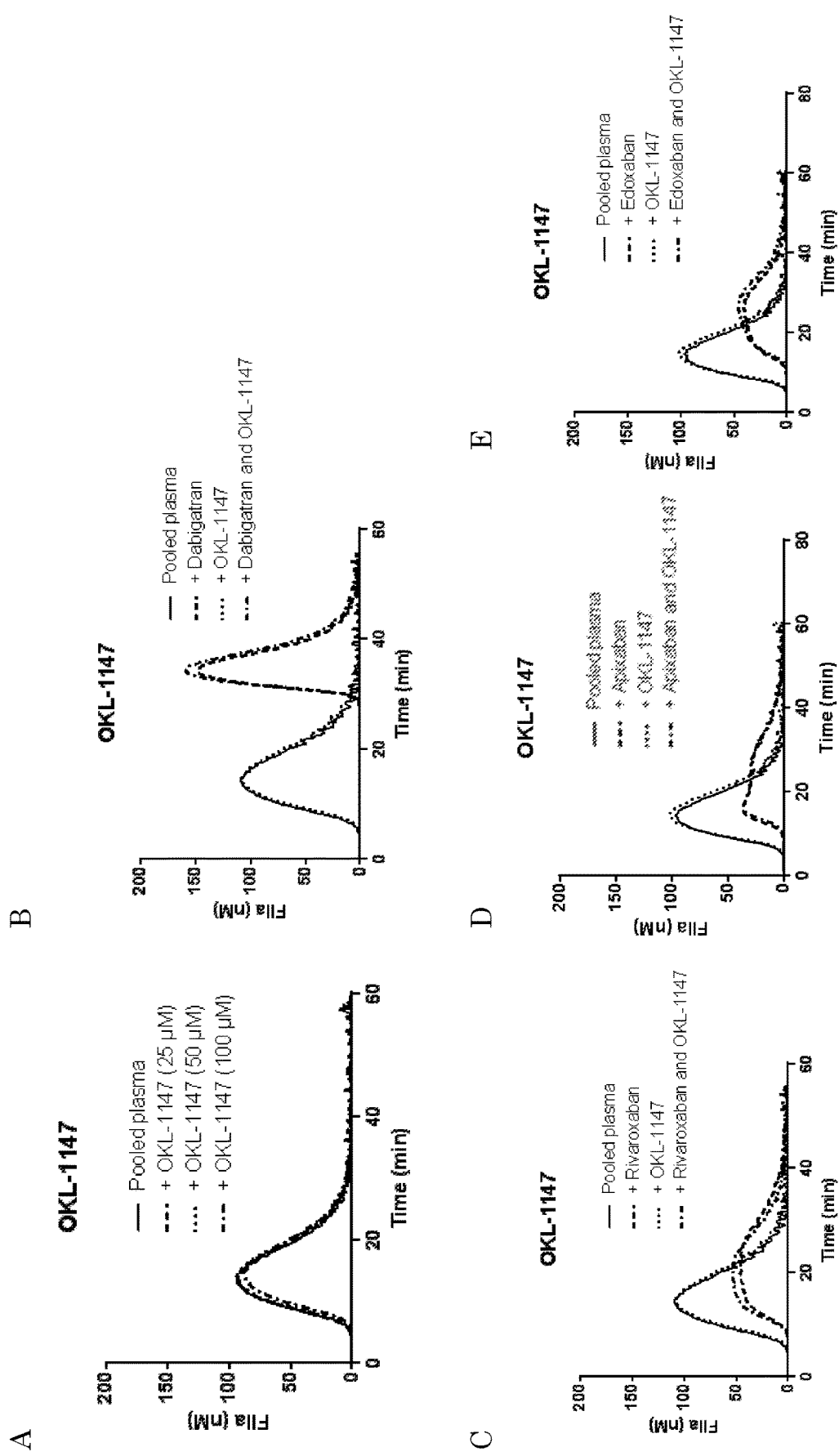
FIG. 13: Pooled normal plasma was spiked with OKL-1147 (100 µM, unless otherwise indicated (A)) and anticoagulants (B-E). The concentrations of the anticoagulants were 100 ng/ml for dabigatran (B), 100 ng/ml for rivaroxaban (C), 60 ng/ml for apixaban (D), 60 ng/ml for edoxaban (E). The plasmas were subjected to thrombin generation analysis as described in the Materials and Methods section with 1 pM tissue factor (TF) as initiator of coagulation.

In several experiments the amine-substituted γ-cyclodextrin OKL-1147 was used as a negative control for the γ-series cyclodextrins since it had no procoagulant effect in plasma, nor did it influence the anticoagulant effect of the NOACs (FIG. 13).

Coagulation Assays in Deficient Plasma

Figure 20:
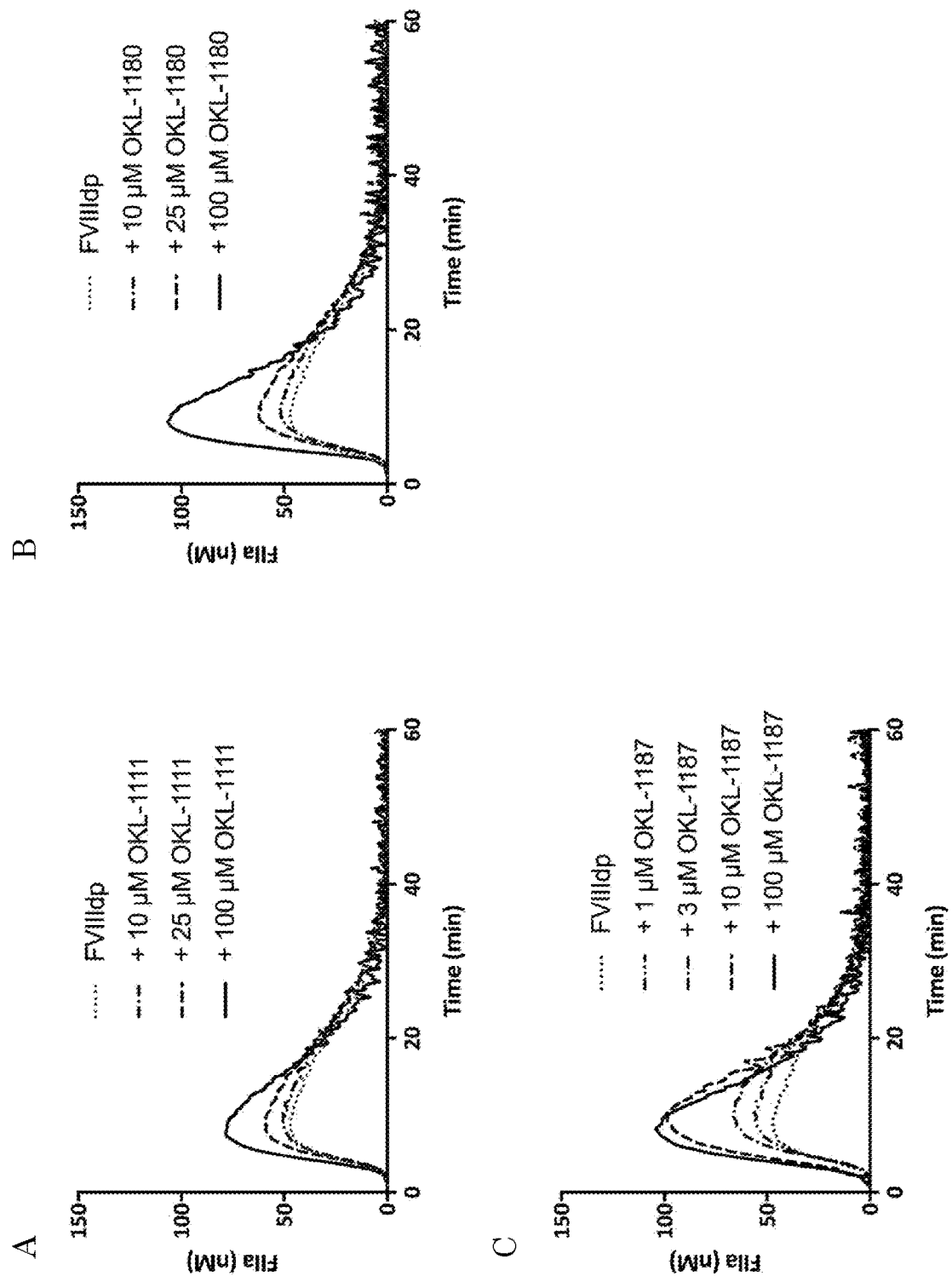
FIG. 20: Plasma deficient in coagulation factor VIII was spiked with cyclodextrin OKL-1111 (A), OKL-1180 (B), and OKL-1187 (C) at the indicated concentrations.

The procoagulant effect of the substituted cyclodextrins was also tested in plasma deficient in coagulation factor VIII and IX. The procoagulant effect of the cyclodextrins OKL-1107, OKL-1110, OKL-1111 has further been investigated in human plasma deficient in coagulation factor XI. The results are summarized in table 4 and representative graphs for OKL-1111, OKL-1180 and OKL-1187 are shown in FIG. 20.

OKL-1111 was able to stimulate coagulation significantly in factor in factor VII, IX and XI deficient plasma (table 4, FIG. 20), OKL-1171, OKL-1172, OKL-1174, OKL-1180, OKL-1181, OKL-1187, OKL-1188, OKL-1189 and OKL-1191 also showed procoagulant effects in factor VIII deficient plasma and OKL-1172, OKL-1174, OKL-1180, OKL-1181, OKL-1188, OKL-1189 and OKL-1191 showed procoagulant activity in factor IX deficient plasma (table 4).

TABLE 4

Effect of procoagulant CDs in Factor VIII or Factor IX depleted plasma.

| Compound | Normal plasma | FVIII dp | FIX dp |
|---|---|---|---|
| OKL-1105 | ** | — | — | *
| OKL-1106 | **** | — | — | **
| OKL-1107 | *** | — | — | ***
| OKL-1108 | * | — | — | ****
| OKL-1109 | * | — | — | *****
| OKL-1110 | ** | — | — | ******
| OKL-1111 | **** | ** | * |
| OKL-1146 | *** | — | — |
| OKL-1171 | * | * | — |
| OKL-1172 | *** | *** | *** |
| OKL-1174 | **** | * | * |
| OKL-1178 | * | — | — |
| OKL-1180 | *** | *** | *** |
| OKL-1181 | ** | * | * |
| OKL-1186 | * | — | — |
| OKL-1187 | ****** | ***** | — |
| OKL-1188 | **** | ** | *** |
| OKL-1189 | **** | ** | ** |

TABLE 4-continued

Effect of procoagulant CDs in Factor VIII or Factor IX depleted plasma.

| Compound | Normal plasma | FVIII dp | FIX dp |
|---|---|---|---|
| OKL-1190 | * | — | — |
| OKL-1191 | **** | * | ** |

The number of * shows the strength of orocoagulant activity.
The increasing number of * indicates stronger procoagulant activity.
— indicates no procoagulant activity in coagulation assay.

Coagulation Assays in Antibody Pre-Treated Plasma

Normal plasma was spiked with inhibitory antibodies against factor VIII (Sanquin, VK34, 14 μg/ml), factor IX (Sanquin, 5F5, 20 μg/ml) or factor XI (Sanquin, mix of #203 and #175, 75 μg/ml). The effect of OKL-1111 was tested in thrombin generation assay using 1 pM tissue factor (TF). This model is representative for hemophilia A, B and C patients that have developed inhibitory antibodies against plasma-derived or recombinant factor VIII or IX or XI they are treated with.

Figure 21:
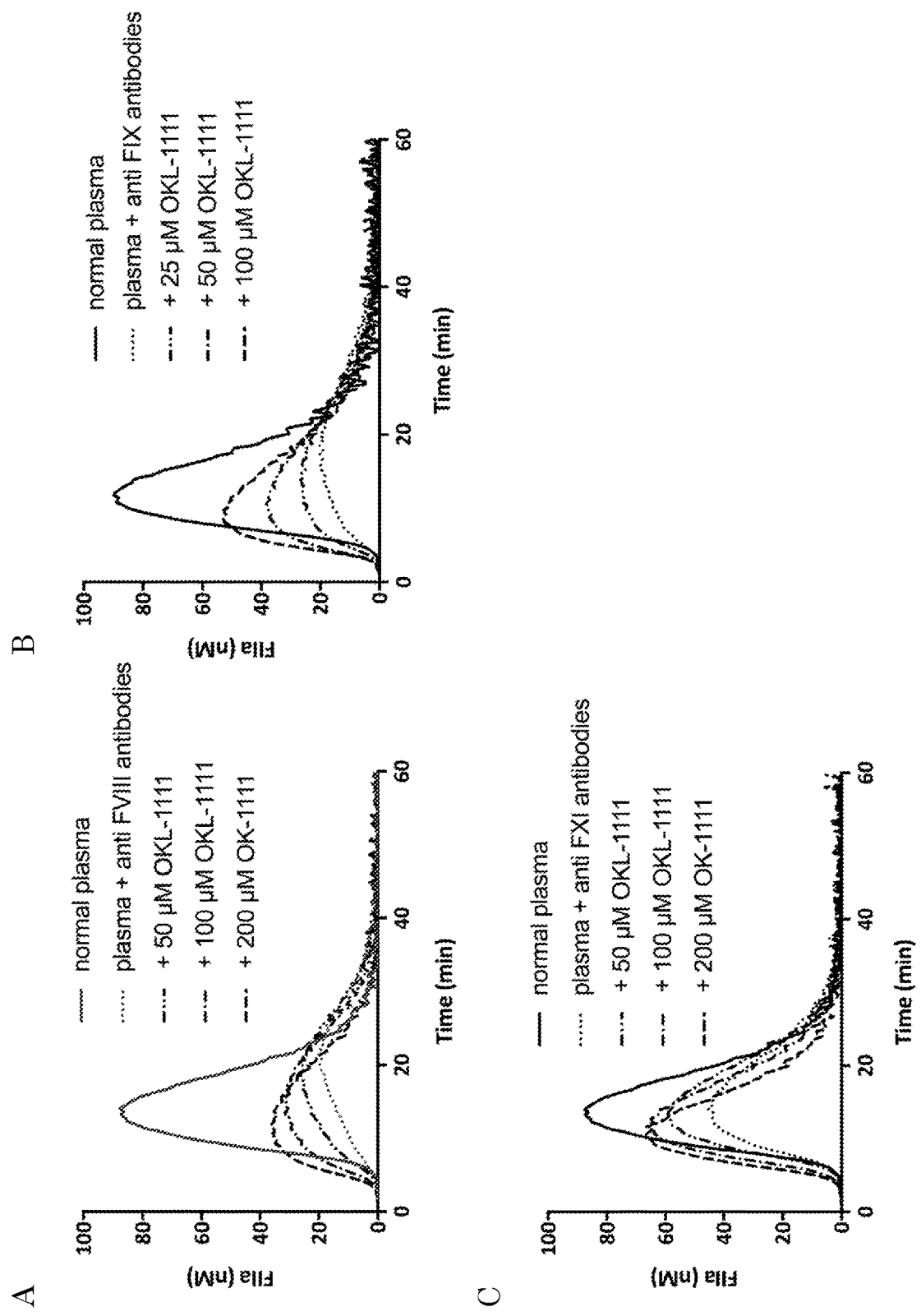
FIG. 21: Effect of OKL-1111 on normal plasma spiked with inhibitory antibodies against factor VIII (A); factor IX (B), and factor XI (C).

OKL-1111 concentration-dependently stimulated thrombin generation in normal human plasma pretreated with inhibitory antibodies against factor VIII, factor IX and factor XI (FIG. 21 A-C).

Coagulation Assays in Plasma of a Hemophilia a Patient

Figure 28:
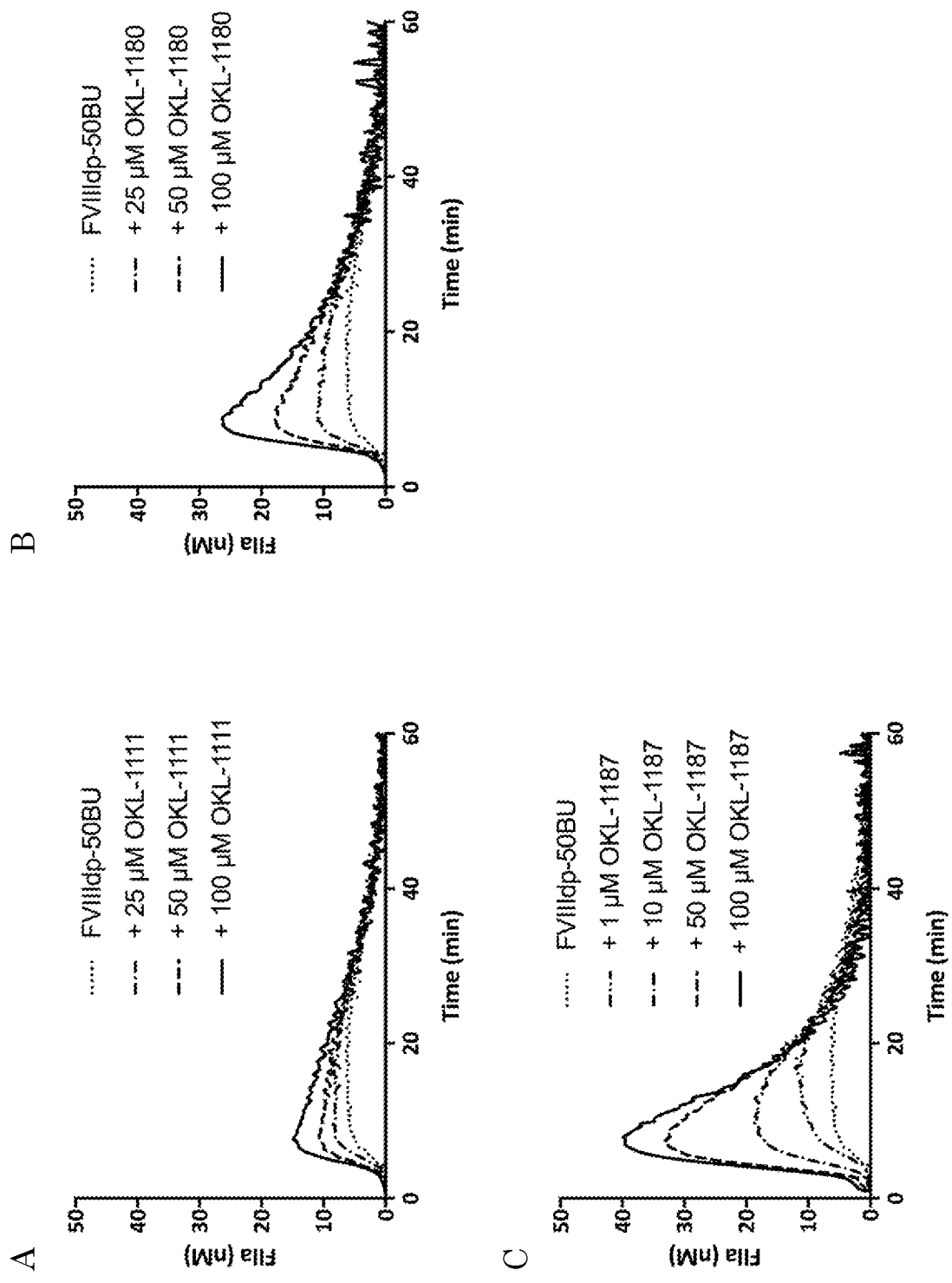
FIG. 28: Effect of OKL-1111 (A), OKL-1180 (B) and OKL-1187 (C) on coagulation in plasma of a hemophilia A patient with anti-factor VIII antibodies. BU=Bethesda Units.

The procoagulant effect of OKL-1111, OKL-1180 and OKL-1187 was also tested in plasma of a hemophilia A patient (George King Rio-Medical, USA). The patient had developed antibodies against factor VIII prior to plasma withdrawal. The plasma contained high levels of anti-FVIII antibodies (50 BU). All tested cyclodextrins concentration-dependently stimulated thrombin generation in this plasma containing anti-FVIII antibodies (FIG. 28).

In Vivo Bleeding Model

In order to investigate whether the procoagulant effect observed in the in vitro assays was also observed in vivo, OKL-1111 was administered to mice that were anticoagulated with rivaroxaban.

Figure 29:
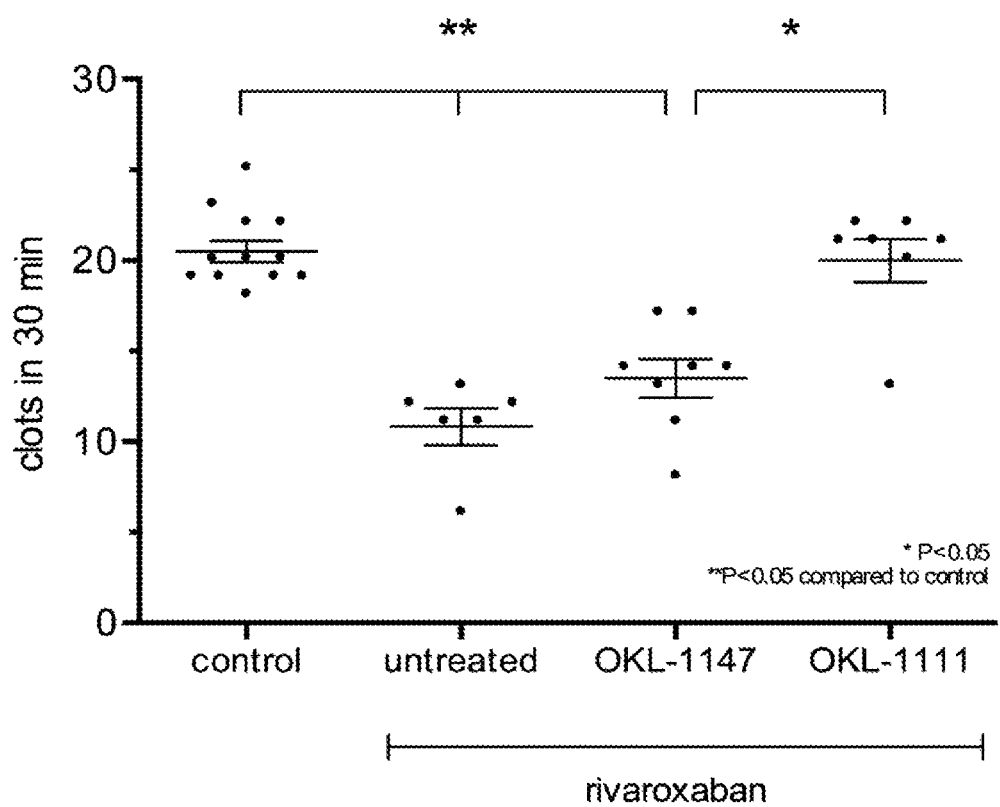
FIG. 29: In vivo analysis of procoagulant potential of OK-1111 and OKL-1147. Except for controls, animals were treated with rivaroxaban for 4 days and cyclodextrins were administered 5 min prior bleeding assay.

In a non-anticoagulated mouse a clot forms in a little over 1 minute after puncture of the blood vessel. As such, in a 30 minute time period about 20-25 clots will form. In mice fed with rivaroxaban, bleeding time was roughly doubled, so that animals only formed about 10-13 clots in 30 minutes. A dose of OKL-1111 expected to give 25 μM in plasma, gave a normalization of the clotting times. In contrast, OKL-1147 was without any significant effect in this respect (FIG. 29).

In order to test the efficacy of OKL-1111 and OKL-1187 in hemophilia in vivo, the vena saphena bleeding model was used as well. Hemophilia A mice were injected with a very low dose of factor VIII (2.5 IU/kg which is designed to give plasma levels of about 0.0625 TU/dL) with or without OKL-1111 or OKL-1187.

Figure 30:
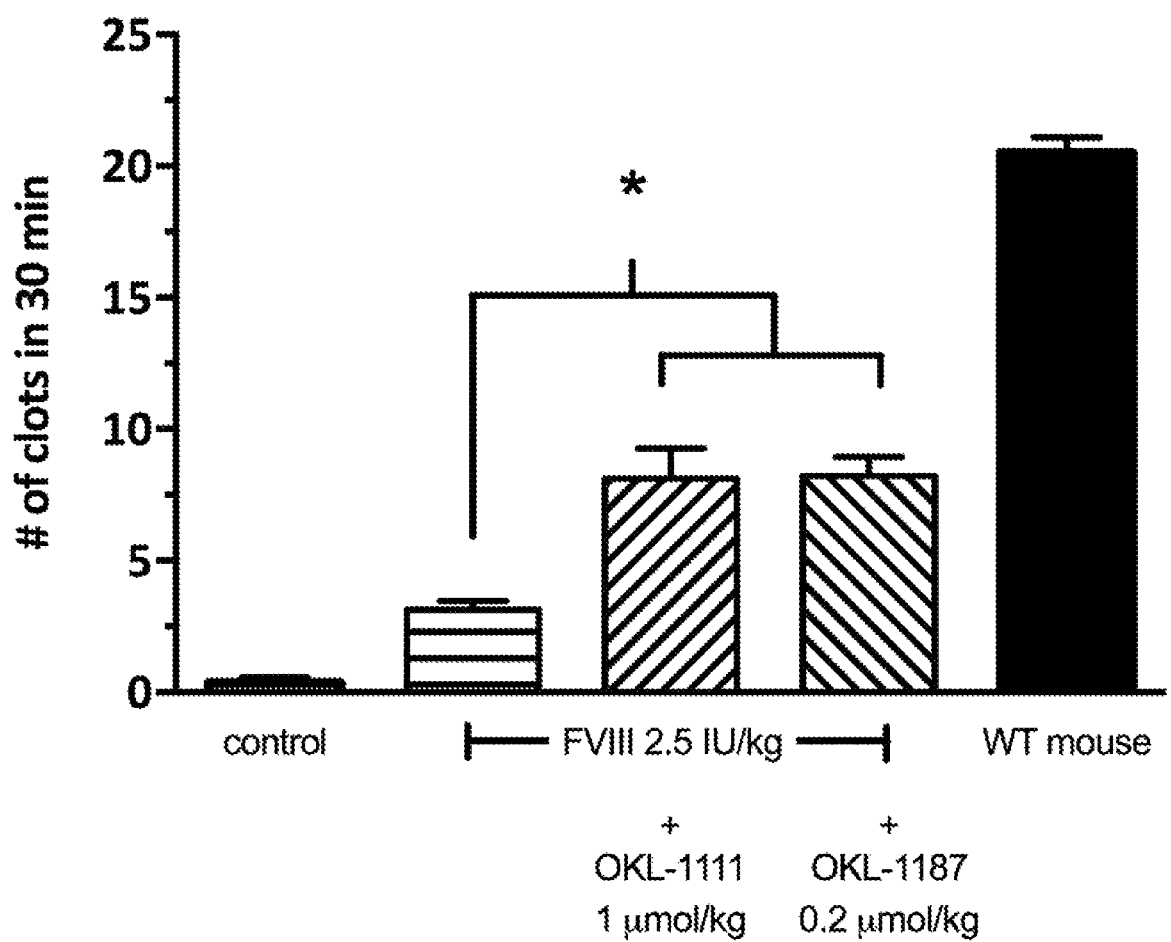
FIG. 30: Effect of OKL-1111 and OKL-1187 on coagulation in mouse hemophilia A assay.

Hemophilic mice (that completely lack factor VIII) do not or only form one clot in 30 minutes after puncture of the vena saphena, whereas in wild type mice this amounts to about 20 clots. In the presence of a low dose of factor VIII, the number of clots in hemophilic mice is increased to approximately 2-3 clots. At a dose of 1 μmol/kg, designed to give a plasma value of 25 μM, OKL-1111 increased hemostasis significantly higher compared to factor VIII alone. In the presence of OKL-1111, 7-9 clots are formed over a 30 minute period (FIG. 30). Similar results were obtained in the presence of 0.2 μmol/kg of OKL-1187.

The invention claimed is:

1. A method for treating a blood coagulation disorder, inducing or stimulating blood coagulation, reducing or preventing bleeding or reversing an anticoagulant effect of an anticoagulant in a subject in need thereof, comprising administering to the subject a therapeutically effective amount of a substituted cyclodextrin of formula (I):

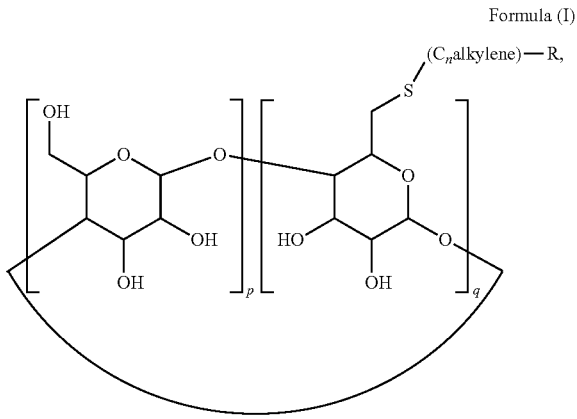

Formula (I)

wherein n is an integer from 3 to 7 and R is selected from the group consisting of —COOH, —OH and —COO(1-4C) alkyl, and wherein p+q is 6, 7 or 8, whereby p is 5 and q is 1 or p is 6 and q is 1, or p is 7 and q is 1, or p is 0 and q is 6, or p is 0 and q is 7, or p is 0 and q is 8, or a pharmaceutically acceptable salt or ester thereof.

2. The method according to claim 1, wherein S—($C_n$alkylene)-R is —S—$(CH_2)_m$—R, and m is an integer from 3 to 7.

3. The method according to claim 1, wherein R is selected from the group consisting of —COOH and —OH.

4. A pharmaceutical composition comprising at least one substituted cyclodextrin of formula (I):

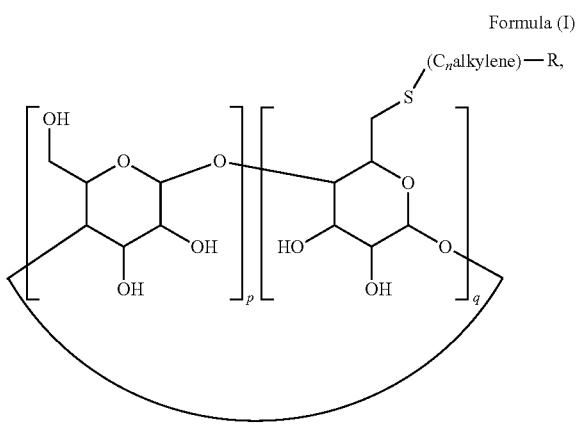

Formula (I)

wherein n is an integer from 3 to 7 and R is selected from the group consisting of —COOH, —OH and —COO(1-4C) alkyl, and wherein p+q is 6, 7 or 8, whereby p is 5 and q, is 1 or p is 6 and q is 1, or p is 7 and q is 1, or p is 0 and q is 6, or p is 0 and q is 7, or p is 0 and q is 8, or a pharmaceutically acceptable salt or ester thereof and at least one pharmaceutically acceptable auxiliary, wherein said pharmaceutical composition is formulated for topical administration as a gel, cream, ointment, dressing, compress, plaster, band-aid or patch.

5. A substituted cyclodextrin of formula (II):

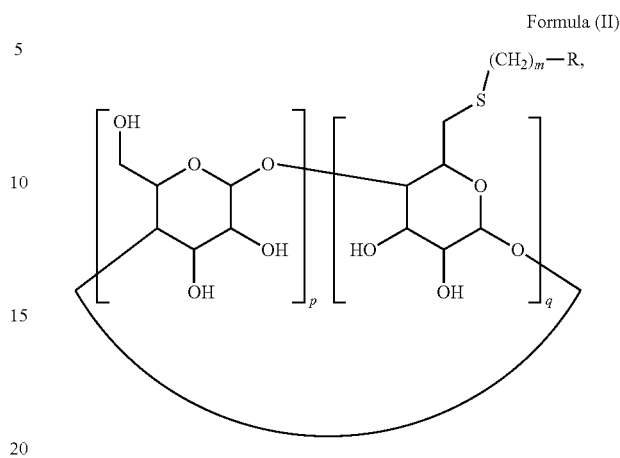

Formula (II)

wherein:
p is 6, q is 1, m is 5 and R is COOH;
p is 0, q is 7, m is 5 and R is COOH;
p is 7, q is 1, m is 5 and R is COOH;
p is 0, q is 7, m is 4 and R is COOH;
p is 0, q is 7, m is 6 and R is COOH;
p is 0, q is 7, m is 7 and R is COOH;
p is 5, q is 1, m is 5 and R is COOH;
p is 0, q is 6, m is 5 and R is COOH;
p is 6, q is 1, m is 6 and R is COOH;
p is 6, q is 1, m is 4 and R is OH;
p is 7, q is 1, m is 6 and R is COOH; or
p is 7, q is 1, m is 4 and R is OH,
or a pharmaceutically acceptable salt or ester of any of these cyclodextrins,
or a substituted cyclodextrin of formula (II) wherein p is 0, q is 8, m is 5 and R is COOH.

6. A substituted cyclodextrin according to claim 5, wherein:
p is 5, q is 1, m is 5 and R is COOH; or
p is 0, q is 6, m is 5 and R is COOH;
or a pharmaceutically acceptable salt or ester of any of these cyclodextrins.

7. A pharmaceutical composition comprising a substituted cyclodextrin or pharmaceutically acceptable salt or ester thereof according to claim 5, and at least one pharmaceutically acceptable auxiliary.

8. A kit comprising:
a substituted cyclodextrin of formula (I):

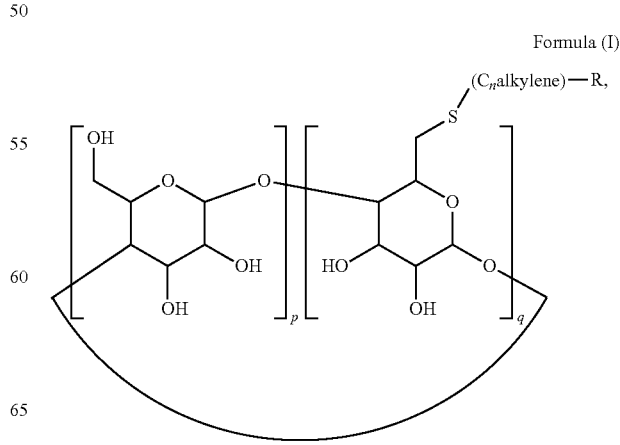

Formula (I)

wherein n is an integer from 3 to 7 and R is selected from the group consisting of —COOH, —OH and —COO(1-4C) alkyl, and wherein p+q is 6, 7 or 8, whereby p is 5 and q is 1, or p is 6 and q is 1, or p is 7 and q is 1, or p is 0 and q is 6, or p is 0 and q is 7, or p is 0 and q is 8, or pharmaceutically acceptable salt thereof, and
a recombinant or isolated coagulation factor.

9. A kit according to claim 8, wherein said recombinant or isolated coagulation factor is factor VIII and said substituted cyclodextrin is a cyclodextrin wherein S—($C_n$alkylene)-R is —S—$(CH_2)_m$—R, and wherein:
p is 0, q is 8, m is 5 and R is COOH,
p is 0, q is 8, m is 4 and R is COOH,
p is 0, q is 8, m is 6 and R is COOH,
p is 0, q is 8, m is 4 and R is OH,
p is 0, q is 7, m is 7 and R is COOH,
p is 0, q is 7, m is 3 and R is OH,
p is 0, q is 6, m is 5 and R is COOH,
p is 6, q is 1, m is 6 and R is COOH,
p is 6, q is 1 m is 4 and R is OH or
p is 7, q is 1, m is 4 and R is OH,
or a pharmaceutically acceptable salt or ester thereof.

10. A kit according to claim 8, wherein said recombinant or isolated coagulation factor is factor IX and said substituted cyclodextrin is a cyclodextrin wherein S—($C_n$alkylene)-R is —S—$(CH_2)_m$—R, and wherein:
p 0, q is 8, m is 5 and R is COOH,
p is 0, q is 8, m is 6 and R is COOH,
p is 0, q is 8, m is 4 and R is OH,
p is 0, q is 7, m is 7 and R is COOH,
p is 0, q is 7, m is 3 and R is OH,
p is 6, q is 1, m is 6 and R is COOH,
p is 6, q is 1 m is 4 and R is OH or
p is 7, q is 1, m is 4 and R is OH,
or a pharmaceutically acceptable salt or ester thereof.

11. A kit according to claim 8, wherein said recombinant or isolated coagulation factor is factor IX and said substituted cyclodextrin is a cyclodextrin wherein S—($C_n$alkylene)-R is —S—$(CH_2)_m$—R and wherein p is 0, q is 8, m is 5 and R is COOH, or a pharmaceutically acceptable salt or ester thereof.

12. The method according to claim 1 for reversing an anticoagulant effect of an anticoagulant in a subject in need thereof, wherein said subject has been treated with an anticoagulant, is undergoing surgery, is undergoing dental treatment, is suffering from trauma, is suffering from induced or spontaneous major bleeding, and/or is suffering from or at risk of hereditary or drug-induced thrombocytopenia.

13. The method according claim 1 for reversing an anticoagulant effect of an anticoagulant, wherein the anticoagulant is selected from the group consisting of:
a direct thrombin inhibitor,
a direct factor Xa inhibitor,
a pentasaccharide,
a low molecular weight heparin,
unfractionated heparin,
a vitamin K antagonist, and
an antiplatelet drug.

14. The method according to claim 1, wherein said disorder is selected from the group consisting of congenital or acquired hemophilia A, hemophilia B, hemophilia C, von Willebrand disease, factor V, factor VII, factor X and/or factor XI deficiency, factor XIII or alpha2-antiplasmin deficiency, hereditary or drug-induced thrombocytopenia, Wiskott-Aldrich Syndrome, Glanzmann's thrombasthenia, Bernard-Soulier Syndrome, idiopathic dense-granule disorder, Hermansky-Pudlak syndrome, Chediak-Higashi syndrome, gray platelet syndrome, Paris-Trousseau/Jacobsen's syndrome, disseminated intravascular coagulation and vitamin K deficiency.

15. The method according to claim 12, wherein said induced or spontaneous major bleeding is intracranial or gastro-intestinal bleeding.

16. The method according to claim 13 wherein;
said direct thrombin inhibitor is dabigatran, hirudin, bivalirudin, lepirudin and/or argatroban,
said direct factor Xa inhibitor is rivaroxaban, apixaban, edoxaban, betrixaban, darexaban, letaxaban and/or eribaxaban,
said pentasaccharide is fondaparinux and/or idraparinux,
said low molecular weight heparin is nadroparin, tinzaparin, dalteparin, enoxaparin, bemiparin, reviparin, parnaparin and/or certoparin,
said vitamin K antagonist is acenocoumarol, phenprocoumon, warfarin, atromentin and/or phenindione, and/or
said antiplatelet drug is an irreversible cyclooxygenase inhibitor, an ADP receptor inhibitor, a phosphodiesterase inhibitor, a PAR-1 antagonist, a GPIIB/IIIa inhibitor, an adenosine reuptake inhibitor, a thromboxane inhibitor or a thromboxane receptor antagonist.

17. The method according to claim 14 wherein;
said hereditary or drug-induced thrombocytopenis is immune thrombocytopenia purpura, thrombotic thrombocytopenic purpura, fetal or neonatal alloimmune thrombocytopenia and/or post-transfusion thrombocytopenic purpura, or
said vitamin K deficiency is vitamin K deficiency of the newborn.

18. The method according to claim 16 wherein;
said irreversible cyclooxygenase inhibitor is aspirin or a derivative thereof and/or triflusal,
said ADP receptor inhibitor is clopidogrel, prasugrel, ticagrelor, ticlopedine, cangrelor and/or elinogrel,
said phosphodiesterase inhibitor is cilostazol,
said PAR-1 antagonist is voraxapar,
said GPIIB/IIIa inhibitor is abciximab, eptifibatide, tirofiban, roxifiban and/or orbofiban,
said adenosine reuptake inhibitor is dipyridamole,
said thromboxane inhibitor is ifetroban and/or picotamide, and/or
said thromboxane receptor antagonist is terutroban and/or picotamide.

* * * * *